US007973078B2

(12) United States Patent
Kubota et al.

(10) Patent No.: US 7,973,078 B2
(45) Date of Patent: Jul. 5, 2011

(54) SULFONAMIDE COMPOUND OR SALT THEREOF

(75) Inventors: Hideki Kubota, Tokyo (JP); Susumu Toda, Tokyo (JP); Issei Tsukamoto, Tokyo (JP); Yuta Fukuda, Tokyo (JP); Ryutaro Wakayama, Tokyo (JP); Kazuki Ono, Tokyo (JP); Toru Watanabe, Tokyo (JP); Hidenori Azami, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 11 days.

(21) Appl. No.: 12/297,445

(22) PCT Filed: Aug. 9, 2007

(86) PCT No.: PCT/JP2007/065613
§ 371 (c)(1),
(2), (4) Date: Oct. 17, 2008

(87) PCT Pub. No.: WO2008/018544
PCT Pub. Date: Feb. 14, 2008

(65) Prior Publication Data
US 2009/0312328 A1      Dec. 17, 2009

(30) Foreign Application Priority Data

Aug. 10, 2006   (JP) ................................. 2006-218923

(51) Int. Cl.
*C07C 303/00* (2006.01)
*A01N 41/06* (2006.01)
(52) U.S. Cl. ............. 514/601; 514/602; 564/80; 564/84
(58) Field of Classification Search .................. None
See application file for complete search history.

(56) References Cited

U.S. PATENT DOCUMENTS

| 6,211,197 | B1 | 4/2001 | Belley et al. |
| 6,448,290 | B1 | 9/2002 | Ohuchida et al. |
| 6,790,866 | B2 | 9/2004 | Nagao et al. |
| 2001/0031766 | A1 | 10/2001 | Belley et al. |
| 2003/0060460 | A1 | 3/2003 | Ohuchida et al. |
| 2004/0082653 | A1 | 4/2004 | Nonaka et al. |
| 2004/0102524 | A1 | 5/2004 | Hughes |
| 2005/0020646 | A1 | 1/2005 | Newgreen et al. |
| 2005/0124672 | A1 | 6/2005 | Naganawa et al. |
| 2005/0245535 | A1 | 11/2005 | Hangeland et al. |
| 2006/0030713 | A1 | 2/2006 | Naganawa et al. |
| 2006/0100195 | A1 | 5/2006 | Maruyama et al. |
| 2006/0100219 | A1 | 5/2006 | Kauffmann-Hefner et al. |

FOREIGN PATENT DOCUMENTS

| EP | 1 447 096 | 8/2004 |
| EP | 1 642 594 A1 | 4/2006 |
| JP | 2002 526517 | 8/2002 |
| JP | 2004 520433 | 7/2004 |
| JP | 2005 206492 | 8/2005 |
| WO | 97 36583 | 10/1997 |
| WO | 98 27053 | 6/1998 |
| WO | 00 26197 | 5/2000 |
| WO | 00 50391 | 8/2000 |
| WO | 00 69465 | 11/2000 |
| WO | 01 02363 | 1/2001 |
| WO | 01 12186 | 2/2001 |
| WO | 02 20463 | 3/2002 |
| WO | WO 02/32864 A1 | 4/2002 |
| WO | 02 072145 | 9/2002 |
| WO | 02 072564 | 9/2002 |
| WO | 2004 033418 | 4/2004 |
| WO | 2005 000356 | 1/2005 |

OTHER PUBLICATIONS

Coli et al, Expert Opinion Invest. Drugs, 2007, 16(7) 999-1007.*
Prostatitis (2009), http://www.mayoclinic.com/health/prostatitis/DS00341/DSECTION=treatments-and-drugs.*
Giannitsas et al., Expert Opin. Ther. Patents (2009) 19, 107-117.*
Smith et al., caplus an 2000:608717.*
Abrams, Paul et al., "The Standardisation of Terminology of Lower Urinary Tract Function: Report from the Standardisation Sub-committee of the International Continence Society", Neurourology and Urodynamics, vol. 21, pp. 167-178, (2002).
Schuessler, B. "Comparison of the mode of action of prostaglandin $E_2$ ($PGE_2$) and sulprostone, a $PGE_2$-derivative, on the lower urinary tract in healthy women", UROL RES, vol. 18, No. 5, pp. 349-352, (1990).
Ishizuka, Osamu et al., "Prostaglandin $E_2$-Induced Bladder Hyperactivity in Normal, Conscious Rats: Involvement of Tachykinins", The Journal of Urology, vol. 153, No. 6, pp. 2034-2038, (1995).
"Prostaglandin $E_2$", Journal of the Japanese Urological Association, vol. 92, No. 2, PM 304, (2001). "Prostaglandin $E_2$", The $89^{th}$ Annual Meeting of the Japanese Urological Association, Kobe, PM 305, (2001).
Nakayama, Yoshito et al., "Role of Prostaglandin Receptor $EP_1$, in the Spinal Dorsal Horn in Carrageenan-induced Inflammatory Pain", Anesthesiology, vol. 97, No. 5, pp. 1254-1262, (2002).
Omote, Keiichi et al., "The Effects of Intrathecal Administration of an Antagonist for Prostaglandin E Receptor Subtype $EP_1$ on Mechanical and Thermal Hyperalgesia in a Rat Model of Postoperative Pain", Anesth Analg, vol. 95, No. 6, pp. 1708-1712, (2002).
Kawahara, Hiroyasu et al., "A Prostaglandin $E_2$ Receptor Subtype $EP_1$ Receptor Antagonist (ONO-8711) Reduces Hyperalgesia, Allodynia, and C-fos Gene Expression in Rats with Chronic Nerve Constriction", Anesth Analg, vol. 93, No. 4, pp. 1012-1017, (2001).
Sarkar, Sanchoy et al., "The Prostaglandin E2 Receptor-1 (EP-1) Mediates Acid-Induced Visceral Pain Hypersensitivity in Humans", Gastroenterology, vol. 124, No. 1, pp. 18-25, (2003).

(Continued)

Primary Examiner — Sun Jae Y Loewe
(74) Attorney, Agent, or Firm — Oblon, Spivak, McClelland, Maier & Neustadt, L.L.P.

(57) ABSTRACT

A compound that can be used as an agent for treating a disease associated with an EP1 receptor, in particular a lower urinary tract symptom. It was confirmed that a sulfonamide compound having an amide structure and characterized by a chemical structure in which a carbon atom in the amide bonds to the N atom in sulfonamide through lower alkylene, or a salt thereof, has a potent EP1 receptor antagonistic activity, accomplishing the present invention. Since the sulfonamide compound of the present invention or a pharmaceutically acceptable salt thereof has a potent EP1 receptor antagonistic activity, it is useful as an agent for treating a disease associated with an EP1 receptor, in particular, a lower urinary tract symptom.

20 Claims, No Drawings

OTHER PUBLICATIONS

McKeown, Stephen C. et al., "Identification of novel glycine sulfonamide antagonists for the $EP_1$ Receptor", Bioorganic & Medicinal Chemistry Letters, Elsevier, vol. 17, No. 6, pp. 1750-1754, (2007).

Hall, Adrian et al., "Identification and optimization of novel 1,3,4-oxadiazole $EP_1$ receptor antagonists", Bioorganic & Medicinal Chemistry Letters, Elsevier, vol. 17, No. 16, pp. 4450-4455, (2007).

Office Action issued Aug. 20, 2010, in Chinese Application 200780029730.2 (with English-languageTranslation).

A.J. Wein et al., Urology, vol. 60 (Supplement 5A), pp. 7-12 (2002).

K.T. McVary, The American Journal of Managed Care, vol. 12(5 suppl), pp. S122-S128 (2006).

AUA Practice Guidelines Committee, The Journal of Urology, vol. 170, pp. 530-547 (2003).

Dler Besarani et al., BJU International, vol. 94(9), pp. 1245-1247 (2004).

Z. Sikafi et al., British Journal of Urology, vol. 57, pp. 308-310 (1985).

M. Wyllie, BJU International, vol. 96, pp. 909-910 (2005).

C. Lowell Parsons., Expert Opin. Pharmacother., vol. 7(4), pp. 411-419 (2006).

G. M. Habermacher et al., Annu. Rev. Med., vol. 57, pp. 195-206 (2006).

Office Action issued Jan. 7, 2011, in Indonesia Patent Application No. W-00 2009 00334 (with English-language Translation).

Extended European Search Report issued Jan. 13, 2011 in EP 07 79 2264.

Database: Beilstein [Online], Beilstein Institute for Organic Chemistry, Frankfurt-Main, DE, XP-002614372, Database Accession No. 3473782, 1950, 1 page.

Database: Beilstein [Online], Beilstein Institute for Organic Chemistry, Frankfurt-Main, DE, vol. 29, XP-002614373, Database Accession No. 2769102, 1963, p. 519.

Database: Beilstein [Online], Beilstein Institute for Organic Chemistry, Frankfurt-Main, DE, vol. 32, XP-002614374, Database Accession No. 2786699, 2773408, 1962, 2 pages.

Database: Beilstein [Online], Beilstein Institute for Organic Chemistry, Frankfurt-Main, DE, vol. 30, XP-002614375, Database Accession No. 2782596, 2676969, 2764955, 1964, 3 pages.

Database: Beilstein [Online], Beilstein Institute for Organic Chemistry, Frankfurt-Main, DE, vol. 34, XP-002614376, Database Accession No. 2767615, 1964, p. 2408.

Anna Quattropani, et al., "Discovery and Development of a New Class of Potent, Selective, Orally Active Oxytocin Receptor Antagonists", J. Med. Chem., vol. 48, XP-002614377, 2005, pp. 7882-7905.

Database: Beilstein [Online], Beilstein Institute for Organic Chemistry, Frankfurt-Main, DE, vol. 29, XP-002614388, Database Accession No. 2817880, 1963, p. 1062.

* cited by examiner

SEQUENCE LISTING

```
<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Lys Thr Ile Ile Ala Leu Ser Tyr Ile Phe Cys Leu Val Phe Ala
1               5                   10                  15

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Tyr Lys Asp Asp Asp Asp Lys
1               5
```

SULFONAMIDE COMPOUND OR SALT THEREOF

CROSS REFERENCES TO RELATED APPLICATIONS

This application is a 371 of International Patent Application No. PCT/JP2007/065613, filed on Aug. 9, 2007, and claims priority to Japanese Patent Application No. 2006-218923, filed on Aug. 10, 2006.

TECHNICAL FIELD

The present invention relates to an EP1 receptor antagonist useful as a therapeutic agent for a lower urinary tract symptom. Furthermore, the present invention relates to a sulfonamide compound or a pharmaceutically acceptable salt thereof useful as an EP1 receptor antagonist.

BACKGROUND ART

Overactive bladder that is one of the diseases leading to a lower urinary tract symptom refers to a clinical condition showing an urinary urgency regardless of the presence or absence of incontinence, which is usually accompanied by a urinary frequency and nocturnal urinary frequency (Non-Patent Document 1). For a treatment of the disease, currently an anticholinergic agent is mainly used, and constant treatment results are given. However, it has been reported that the anticholinergic agent is difficult to be used for patients with prostatic hypertrophy or elderly patients because it is known to cause side-effects such as dry mouth, constipation and blurred vision, as well as a risk of urinary retention. In addition, there are patients showing no improvement with the anticholinergic agent. From the above facts, there is a great expectation about a drug with a new mechanism of action for overactive bladder.

Prostaglandin $E_2$ ($PGE_2$) is a bioactive substance, a precursor of which is arachidonic acid, and is known to participate in regulating functions of the body through 4 subtypes of G-protein coupled receptors, i.e., EP1, EP2, EP3, and EP4.

It has been known that intravesical instillation of $PGE_2$ results in strong urinary urgency and reduction in the bladder capacity in humans (Non-Patent Document 2), and that it results in reduction in the bladder capacity of a rat (Non-Patent Document 3). Accordingly, it has been suggested that there is a possibility that $PGE_2$ influences the function of lower urinary tract. Recently, there has been reported that administration of an EP1 receptor antagonist to a model rat with spinal cord injury is useful in improving the urination function (Non-Patent Document 4), and suggested that the abnormal urination function of a model mouse with urethral stricture is lost in EP1 receptor knock-out mice, and that intravesical instillation of $PGE_2$ shows hyperactivity of the abnormal urination function (Patent Document 1). From these, it is believed that the EP1 receptor antagonist is useful as a remedy for a lower urinary tract symptom.

Moreover, the EP1 receptor antagonist has such a mechanism that particular side effects caused by an anticholinergic agent are expected to be avoided, and an effect on patients whom showed no improvement with the anticholinergic agent is also expected. In addition, this agent is expected to improve certain symptoms further by acting on sensory nerves. Furthermore, this agent has been reported to exhibit an effect of improving clinical condition without lowering the urination efficiency in a model rat with spinal cord injury (Non-Patent Document 5), and thus it is expected to be administered safely to patients with prostatic hypertrophy or elderly patients.

In addition, it has been widely known that $PGE_2$ is produced locally due to inflammation or tissue damage, and enhances the inflammation reaction as well as participating in giving pain or fever. Recently, it has been known that an EP1 receptor antagonist shows efficacy in the model animals with pains of various types such as inflammatory pain (Non-Patent Document 6), postoperative pain (Non-Patent Document 7), and neuropathic pain (Non-Patent Document 8). There is also a report on the clinical effect of administering an EP1 receptor antagonist on visceral pain caused by hydrochloric acid (Non-Patent Document 9). From these, it is believed that the EP1 receptor antagonist is also useful as a remedy for various pains.

Moreover, it has been known that the EP1 receptor antagonist has an inhibitory effect on aberrant crypt foci of the colonic mucosa and on intestinal polyp formation (Patent Document 2), thus it is believed to be useful as a remedy for colon cancer, bladder cancer, prostate cancer, or the like.

As a sulfonamide compound having an EP1 receptor antagonistic activity, for example, compounds mentioned in Patent Documents 3 and 4 have been reported.

Patent Document 3 discloses a compound represented by the formula (A):

[Chem. 1]

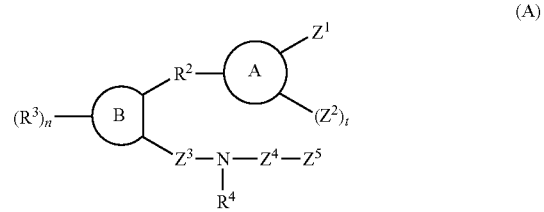

(wherein A and B each independently represents a C5 to 15 carbon ring or a 5- to 7-membered heterocycle, $Z^3$ represents a single bond or C1 to 4 alkylene, $Z^4$ represents $SO_2$ or CO, $R^2$ represents an amide bond, —O—C1 to 4 alkylene, or the like, $R^4$ represents (1) hydrogen, (2) C1 to 8 alkyl, C2 to 8 alkenyl, or C2 to 8 alkynyl, (3) C1 to 6 alkyl substituted with 1 or 2 substituents selected from the group consisting of $COOZ^8$, $CONZ^9Z^{10}$, $OZ^8$, and C1 to 4 alkoxy, (4) C3 to 7 cycloalkyl, or (5) C1 to 4 alkyl, C2 to 4 alkenyl, or C2 to 4 alkynyl, each of which substituted with phenyl or C3 to 7 cycloalkyl, and further, $Z^8$, $Z^9$, and $Z^{10}$ each independently represents hydrogen or C1 to 4 alkyl. For the other symbols, reference can be made to the publication.)

However, there is no specific disclosure of the active ingredient represented by the formula (I) that is an active ingredient of the present invention.

Further, Patent Document 4 discloses a compound represented by the formula (B).

[Chem. 2]

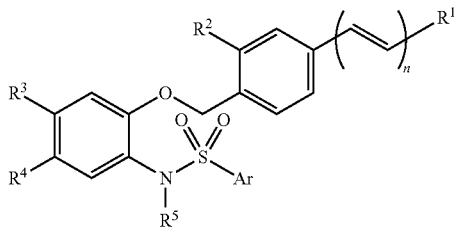

(B)

(wherein $R^5$ represents isopropyl, isobutyl, 2-methyl-2-propenyl, cyclopropyl methyl, methyl, ethyl, propyl, 2-propenyl, or 2-hydroxy-2-methyl propyl. As the other symbols, reference can be made to the publication.)

However, it has a basic structure different from that of the active ingredient represented by the formula (I) that is an active ingredient of the present invention, since $R^5$ has no amide structure.

In addition, as the sulfonamide compound, for example, compounds mentioned in Patent Documents 5 to 8 have been reported.

Patent Document 5 discloses that a compound represented by the formula (C) including a wide variety of compounds has an inhibitory activity against the production of an amyloid β protein, and is useful for treating or preventing Alzheimer's disease, or the like.

[Chem. 3]

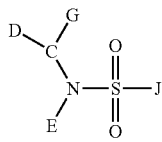

(C)

(for the symbols in the formula, see the publication)

However, there is no description on an EP1 receptor antagonistic activity of the compound, and also no specific disclosure of the compound (II) of the present invention.

Moreover, Patent Document 6 discloses that a compound represented by the formula (D) including a wide variety of compounds has farnesoid-X receptor (FXR) antagonistic activity, and is useful for treating diseases related to cholesterol abnormality, obesity, diabetes, or the like.

[Chem. 4]

$B^1$-$L^1$-$A^1$-$L^2$-$B^2$ (D)

(for the symbols in the formula, see the publication)

However, there is no description on an EP1 receptor antagonistic activity of the compound, and also no specific disclosure of the compound (II) of the present invention.

Furthermore, Patent Document 7 discloses that a compound represented by the formula (E) has orexin receptor antagonistic activity, and is useful for treating sleep disorders, stress-related disorders, or the like.

[Chem. 5]

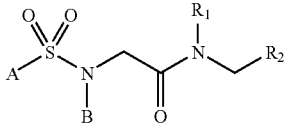

(E)

(for the symbols in the formula, see the publication)

However, there is no description on an EP1 receptor antagonistic activity of the compound, and also no specific disclosure of the compound (II) of the present invention.

Furthermore, Patent Document 8 discloses that a compound represented by the formula (F) has diacylglycerol acyl transferase (DGAT) inhibitory activity, and is useful for treating or preventing obesity, hyperlipidemia, diabetes, or the like.

[Chem. 6]

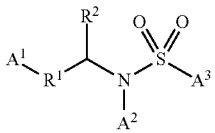

(F)

(for the symbols in the formula, see the publication)

However, there is no description on an EP1 receptor antagonistic activity of the compound, and also no specific disclosure of the compound (II) of the present invention.

In addition, methyl 4-({[N-[(4-fluorophenyl)sulfonyl]-N-(2-methoxyphenyl)glycyl]amino}methyl)benzoate (Registry Number: 851172-09-3; for example, Catalogue name: Aurora Screening Library, Order No. kend-0100022), and $N^2$-[(4-chlorophenyl)sulfonyl]-$N^2$-(2,5-difluorophenyl)-N-[4-(1,2,3-thiadiazol-4-yl)benzyl]-D-alaninamide (Patent Document 5, Example 635) having amyloid β protein-production inhibitory activity have been known.

However, there are no reports on the EP1 receptor antagonistic activity of these compounds.

[Non-Patent Document 1] "Neurourology and Urodynamics", (England), 2002, Vol. 21, p. 167-78
[Non-Patent Document 2] "Urological Research", (USA), 1990, Vol. 18, No. 5, p.
[Non-Patent Document 3] "The Journal of Urology", (USA), June 1995, Vol. 153, No. 6, p. 2034-8
[Non-Patent Document 4] "Journal of The Japanese Urological Association", February 2001, Vol. 92, No. 2, p. 304
[Non-Patent Document 5] "The 89th Annual Meeting of The Japanese Urological Association", Kobe, 2001, MP-305
[Non-Patent Document 6] "Anesthesiology", (USA), November 2002, Vol. 97, No. 5, p. 1254-62
[Non-Patent Document 7] "Anesthesia and Analgesia", (USA), December 2002, Vol. 95, No. 6, p. 1708-12
[Non-Patent Document 8] "Anesthesia and Analgesia", (USA), October 2001, Vol. 93, No. 4, p. 1012-7
[Non-Patent Document 9] "Gastroenterology", January 2003, Vol. 124, No. 1, p.
[Patent Document 1] US2005/0020646
[Patent Document 2] WO00/069465
[Patent Document 3] WO98/027053
[Patent Document 4] WO02/072564
[Patent Document 5] WO 00/050391

[Patent Document 6] WO 02/020463
[Patent Document 7] WO 04/033418
[Patent Document 8] Japanese Patent Application Publication No. 2005-206492

DISCLOSURE OF THE INVENTION

Problems to be Solved by the Invention

As described above, the conventional remedy for a lower urinary tract symptom are not satisfactory in the points of efficacy, safety, or the like, and thus there is a strong need of a very effective and safe remedy for a lower urinary tract symptom.

Means for Solving the Problems

As described above, an EP1 receptor antagonist is expected to be a very safe remedy for a lower urinary tract symptom with few side effects such as dry mouth and urinary retention. Therefore, the present inventors have studied extensively on a compound having an EP1 receptor antagonistic activity, aiming at providing a compound that is useful for the treatment of a lower urinary tract symptom, or the like. As a result, they have found that a compound represented by the formula (I) as an active ingredient of the present invention has a potent EP1 receptor antagonistic activity, thereby completing the present invention.

That is, the present invention relates to the followings.

[1] An EP1 receptor antagonist comprising, as an active ingredient, a sulfonamide compound represented by the formula (I) or a pharmaceutically acceptable salt thereof.

[Chem. 7]

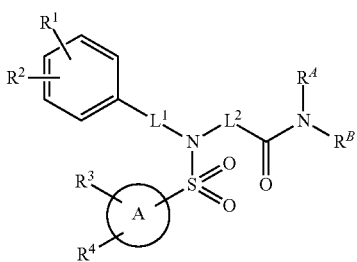

(I)

[wherein the symbols have the following meanings:
Ring A: a benzene ring, a cycloalkane ring, or an aromatic hetero ring,
$L^1$: a single bond or lower alkylene,
$L^2$: lower alkylene,
$R^1$ to $R^4$: the same as or different from each other, each representing $R^0$, halogen, halogeno-lower alkyl, —$OR^0$, —O-halogeno-lower alkyl, —$S(O)_n$-lower alkyl, —CN, —$NO_2$, nitrogen-containing heterocyclic group, cycloalkyl, —NH—CO-lower alkyl, —NH—CO—N($R^{00}$)$_2$, —NH—CO-nitrogen-containing heterocyclic group, —$CO_2R^0$, —CON($R^0$)$_2$, —CO-lower alkyl, -lower alkylene-$OR^0$, -lower alkylene-$CO_2R^0$, aryl which may be substituted, heteroaryl which may be substituted, —O-aryl which may be substituted, —O-benzyl, or —O-heteroaryl which may be substituted, or when $R^1$ and $R^2$, and $R^3$ and $R^4$ are each positioned on the adjacent carbon atoms of a benzene ring or a ring A, they may be taken together with a ring atom to which they bond to form a 5- to 7-membered cycloalkene ring, a benzene ring, or a hetero ring which may be substituted with a group selected from the following $G^1$ group, Group $G^1$: lower alkyl, oxo, —$OR^0$, -lower alkylene-$OR^0$, and —CO-lower alkyl, $R^0$: the same as or different from each other, each representing H or lower alkyl, $R^{00}$: H or lower alkyl which may be substituted with —$OR^0$, n: 0, 1, or 2, $R^A$:$R^0$, $R^B$:$R^0$, -lower alkylene-aryl which may be substituted, -lower alkylene-heteroaryl which may be substituted, -lower alkylene-O-aryl which may be substituted, or -lower alkylene-O-heteroaryl which may be substituted, or $R^A$ and $R^B$ may be taken together with a nitrogen atom to which they bonded to form a nitrogen-containing hetero ring. The same shall apply hereinafter.]

[2] The EP1 receptor antagonist as described in [1], wherein $R^A$ is H, and $R^B$ is -lower alkylene-aryl which may be substituted, -lower alkylene-heteroaryl which may be substituted, -lower alkylene-O-aryl which may be substituted, or -lower alkylene-O-heteroaryl which may be substituted.

[3] A sulfonamide compound represented by the formula (II) or a pharmaceutically acceptable salt thereof.

[Chem. 8]

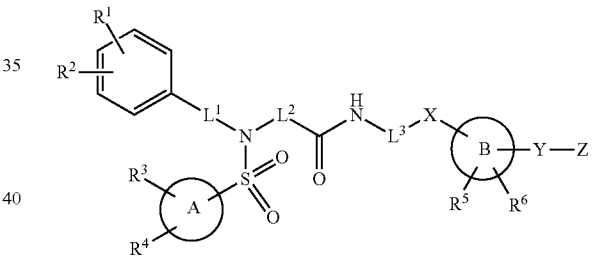

(II)

[wherein the symbols have the following meanings:
Ring A: a benzene ring, a cycloalkane ring, or an aromatic hetero ring,
$L^1$: a single bond or lower alkylene,
$L^2$: lower alkylene,
$R^1$ to $R^4$: the same as or different from each other, each representing $R^0$, halogen, halogeno-lower alkyl, —$OR^0$, —O-halogeno-lower alkyl, —$S(O)_n$-lower alkyl, —CN, —$NO_2$, nitrogen-containing heterocyclic group, cycloalkyl, —NH—CO-lower alkyl, —NH—CO—N($R^{00}$)$_2$, —NH—CO-nitrogen-containing heterocyclic group, —$CO_2R^0$, —CON($R^0$)$_2$, —CO-lower alkyl, -lower alkylene-$OR^0$, -lower alkylene-$CO_2R^0$, aryl which may be substituted, heteroaryl which may be substituted, —O-aryl which may be substituted, —O-benzyl, or —O-heteroaryl which may be substituted, or when $R^1$ and $R^2$, and $R^3$ and $R^4$ are each positioned on the adjacent carbon atoms of a benzene ring or a ring A, they may be taken together with a ring atom to which they bond to form a 5- to 7-membered cycloalkene ring, a benzene ring, or a hetero ring which may be substituted with a group selected from the following $G^1$ group, Group G¹: lower alkyl, oxo, —OR⁰, -lower alkylene-OR⁰, and —CO-lower alkyl, R⁰: the same as or different from each other, each representing H or lower alkyl, R⁰⁰: H or lower alkyl which may be substituted with —OR⁰, n: 0, 1, or 2, L³: lower alkylene, X: a single bond or —O—, Ring B: a benzene ring or an aromatic hetero ring, R⁵ and R⁶: the same as or different from each other, each representing R⁰, halogen, halogeno-lower alkyl, —OR⁰, —O-halogeno-lower alkyl, —CN, or —NO₂, Y: a single bond, lower alkylene, lower alkenylene, or —O-lower alkylene-, Z: —CO₂H or a biological equivalent, —CONR⁷R⁸, or a nitrogen-containing heterocyclic group which may be substituted with a group selected from the G¹ group, R⁷ and R⁸: the same as or different from each other, each representing H or lower alkyl which may be substituted with a group selected from the following G² group, and Group G²: —OR⁰, —N(R⁰)₂, —CO₂R⁰, and a nitrogen-containing heterocyclic group, provided that methyl 4-({[N-[(4-fluorophenyl)sulfonyl]-N-(2-methoxyphenyl)glycyl]amino}methyl)benzoate and N²-[(4-chlorophenyl)sulfonyl]-N²-(2,5-difluorophenyl)-N-[4-(1,2,3-thiadiazol-4-yl)benzyl]-D-alaninamide are excluded. The same shall apply hereinafter.]

[4] The compound or a pharmaceutically acceptable salt thereof as described in [3], wherein L¹ is a single bond.

[5] The compound or a pharmaceutically acceptable salt thereof as described in [4], wherein the ring A is a benzene ring.

[6] The compound or a pharmaceutically acceptable salt thereof as described in [5], wherein X is a single bond.

[7] The compound or a pharmaceutically acceptable salt thereof as described in [6], wherein L² and L³ are both methylene.

[8] The compound or a pharmaceutically acceptable salt thereof as described in [7], wherein Z is —CO₂H or a biological equivalent.

[9] A sulfonamide compound represented by the formula (II-A) or a pharmaceutically acceptable salt thereof.

[Chem. 9]

(II-A)

[wherein the symbols have the following meanings:

R¹⁰ to R¹²: the same as or different from each other, each representing halogen, lower alkyl, halogeno-lower alkyl, —OR⁰, —O-halogeno-lower alkyl, or —CN, R¹³:R⁰, halogen, halogeno-lower alkyl, —OR⁰, —O-halogeno-lower alkyl, or —CN, Ring B: a benzene ring or an aromatic hetero ring, R¹⁴:R⁰, halogen, or —OR⁰, R⁰: the same as or different from each other, each representing H or lower alkyl, Y¹: a single bond, lower alkylene, lower alkenylene, or —O-lower alkylene-, and Z¹: —CO₂H or a biological equivalent. The same shall apply hereinafter]

[10] The compound or a pharmaceutically acceptable salt thereof as described in [3], which is selected from the group consisting of 4-[({N-(3-chloro-2-methylphenyl)-N-[(4-methylphenyl)sulfonyl]glycyl}amino)methyl]benzoic acid, 3-[({N-(3-chloro-2-methylphenyl)-N-[(4-methylphenyl)sulfonyl]glycyl}amino)methyl]benzoic acid, 3-[({N-(3-chloro-2-methylphenyl)-N-[(4-chlorophenyl)sulfonyl]glycyl}amino)methyl]benzoic acid, 3-[({N-(3-chloro-2-methylphenyl)-N-[(4-methylphenyl)sulfonyl]glycyl}amino)methyl]phenoxyacetic acid, 4-[({N-(3-chloro-2-methylphenyl)-N-[(4-methylphenyl)sulfonyl]glycyl}amino)methyl]-N-(methylsulfonyl)benzamide, 3-[({N-(3-chloro-2-methylphenyl)-N-[(4-cyanophenyl)sulfonyl]glycyl}amino)methyl]benzoic acid, 3-{[(N-(3-chloro-2-methylphenyl)-N-{[4-(trifluoromethyl)phenyl]sulfonyl}glycyl)amino]methyl}benzoic acid, 4-[({N-(3-chloro-2-methylphenyl)-N-[(4-methylphenyl)sulfonyl]glycyl}amino)methyl]-2-methoxy-N-(methylsulfonyl)benzamide, 3-[({N-(2,3-dichlorophenyl)-N-[(4-methylphenyl)sulfonyl]glycyl}amino)methyl]benzoic acid, 3-[({N-(3-chloro-2-methoxyphenyl)-N-[(4-methylphenyl)sulfonyl]glycyl}amino)methyl]benzoic acid, 3-[({N-(3-bromo-2-methylphenyl)-N-[(4-methylphenyl)sulfonyl]glycyl}amino)methyl]benzoic acid, 3-[({N-(3-chloro-2-methylphenyl)-N-[(4-ethylphenyl)sulfonyl]glycyl}amino)methyl]benzoic acid, 3-[({N-(3-chloro-2-ethylphenyl)-N-[(4-methylphenyl)sulfonyl]glycyl}amino)methyl]benzoic acid, 3-[({N-(3-chloro-2-methylphenyl)-N-[(4-methylphenyl)sulfonyl]glycyl}amino)methyl]cinnamic acid, 3-{3-[({N-(3-chloro-2-methylphenyl)-N-[(4-methylphenyl)sulfonyl]glycyl}amino)methyl]phenyl}propionic acid, 5-[({N-(3-chloro-2-methylphenyl)-N-[(4-methylphenyl)sulfonyl]glycyl}amino)methyl]thiophene-3-carboxylic acid, 3-[({N-(3-chloro-2-ethylphenyl)-N-[(4-methylphenyl)sulfonyl]glycyl}amino)methyl]cinnamic acid, 3-{[(N-(3-chloro-2-methylphenyl)-N-{[4-(trifluoromethyl)phenyl]sulfonyl}glycyl)amino]methyl}cinnamic acid, 3-[({N-(3-chloro-2-methylphenyl)-N-[(4-chlorophenyl)sulfonyl]glycyl}amino)methyl]cinnamic acid, 3-(3-{[(N-(3-chloro-2-methylphenyl)-N-{[4-(trifluoromethyl)phenyl]sulfonyl}glycyl)amino]methyl}phenyl)propionic acid, 3-[({N-(3-chloro-2-methylphenyl)-N-[(2-fluoro-4-methylphenyl)sulfonyl]glycyl}amino)methyl]benzoic acid, 2-[({N-(3-chloro-2-methylphenyl)-N-[(4-methylphenyl)sulfonyl]glycyl}amino)methyl]-1,3-oxazole-4-carboxylic acid, 4-[({N-(3-chloro-2-methylphenyl)-N-[(4-methylphenyl)sulfonyl]glycyl}amino)methyl]thiophene-2-carboxylic acid, (2S)-2-{3-[({N-(3-chloro-2-methylphenyl)-N-[(4-methylphenyl)sulfonyl]glycyl}amino)methyl]phenoxy}propionic acid, and (2R)-2-{3-[({N-(3-chloro-2-methylphenyl)-N-[(4-methylphenyl)sulfonyl]glycyl}amino)methyl]phenoxy}propionic acid.

[11] A pharmaceutical composition comprising the compound or a pharmaceutically acceptable salt thereof described in [3] as an active ingredient.

[12] The pharmaceutical composition as described in [11], which is an EP1 receptor antagonist.

[13] The pharmaceutical composition as described in [11], which is a therapeutic agent for a lower urinary tract symptom.

[14] The pharmaceutical composition as described in [13], wherein the disease leading to a lower urinary tract symptom is overactive bladder, benign prostatic hyperplasia, bladder neck contracture, cystitis, or prostatitis.

[15] A use of the compound or a pharmaceutically acceptable salt thereof as described in [3], for the manufacture of an agent for treating a lower urinary tract symptom.

[16] The use as described in [15], wherein the disease leading to a lower urinary tract symptom is overactive bladder, benign prostatic hyperplasia, bladder neck contracture, cystitis, or prostatitis.

[17] A method for treating a lower urinary tract symptom, comprising administering a therapeutically effective amount of the compound or a pharmaceutically acceptable salt thereof as described in [3] to a patient.

[18] The method as described in [17], wherein the disease leading to a lower urinary tract symptom is overactive bladder, benign prostatic hyperplasia, bladder neck contracture, cystitis, or prostatitis.

The present invention further relates to the followings.

[19] An EP1 receptor antagonist comprising, an as an active ingredient, a sulfonamide derivative or a pharmaceutically acceptable salt thereof represented by the formula (I-A).

[Chem. 10]

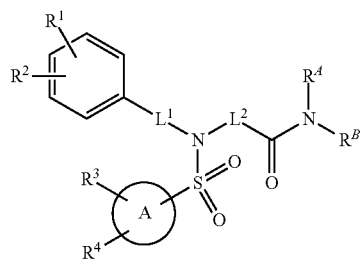

(I-A)

[wherein the symbols have the following meanings:

Ring A: a benzene ring, a cycloalkane ring, or an aromatic hetero ring, $L^1$: a single bond or lower alkylene, $L^2$: lower alkylene, $R^1$ to $R^4$: the same as or different from each other, each representing H, halogen, lower alkyl, halogeno-lower alkyl, —$OR^0$, —O-halogeno-lower alkyl, —CN, —$NO_2$, —$CO_2R^0$, —CO-lower alkyl, -lower alkylene-$OR^0$, -lower alkylene-$CO_2R^0$, aryl which may be substituted, heteroaryl which may be substituted, —O-aryl which may be substituted, —O-benzyl, or —O-heteroaryl which may be substituted, or if $R^1$ and $R^2$, and $R^3$ and $R^4$ are each adjacently positioned on a benzene ring or a ring A, they may be taken together with a carbon atom on the ring to which they are bonded, so as to form a 5- to 7-membered cycloalkene ring or a hetero ring which may be substituted with a group selected from the following $G^1$ group, Group $G^1$: lower alkyl and oxo, $R^0$: H or lower alkyl, $R^A$: H or lower alkyl, $R^B$: H, lower alkyl, -lower alkylene-aryl which may be substituted, -lower alkylene-heteroaryl which may be substituted, -lower alkylene-O-aryl which may be substituted, or -lower alkylene-O-heteroaryl which may be substituted, or $R^A$ and $R^B$ may be taken together with a nitrogen atom to which they bonded to form a nitrogen-containing hetero ring. The same shall apply hereinafter.]

[20] A sulfonamide derivative represented by the formula (II-B) or a pharmaceutically acceptable salt thereof.

[Chem. 11]

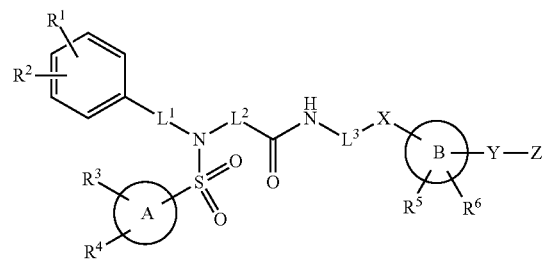

(II-B)

[wherein the symbols have the following meanings:

Ring A: a benzene ring, a cycloalkane ring, or an aromatic hetero ring, $L^1$: a single bond or lower alkylene, $L^2$: lower alkylene, $R^1$ to $R^4$: the same as or different from each other, each representing H, halogen, lower alkyl, halogeno-lower alkyl, —$OR^0$, —O-halogeno-lower alkyl, —CN, —$NO_2$, —$CO_2R^0$, —CO-lower alkyl, -lower alkylene-$OR^0$, -lower alkylene-$CO_2R^0$, aryl which may be substituted, heteroaryl which may be substituted, —O-aryl which may be substituted, —O-benzyl, or —O-heteroaryl which may be substituted, or if $R^1$ and $R^2$, and $R^3$ and $R^4$ are each adjacently positioned on a benzene ring or a ring A, they may be taken together with a carbon atom on the ring to which they are bonded, so as to form a 5- to 7-membered cycloalkene ring or a hetero ring which may be substituted with a group selected from the following $G^1$ group, Group $G^1$: lower alkyl and oxo, $R^0$: H or lower alkyl, $L^3$: lower alkylene, X: a single bond or —O—, B: a benzene ring or an aromatic hetero ring, $R^5$ and $R^6$: the same as or different from each other, each representing H, halogen, lower alkyl, halogeno-lower alkyl, —$OR^0$, —O-halogeno-lower alkyl, —CN, or —$NO_2$, Y: a single bond, lower alkylene, lower alkenylene, or —O-lower alkylene-, Z: —$CO_2R^0$, —$CONR^7R^8$, —CONH—$SO_2$—$R^9$, or a nitrogen-containing heterocyclic group which may be substituted with a group selected from the $G^1$ group, $R^7$ and $R^8$: the same as or different from each other, each representing H or lower alkyl which may be substituted with a group selected from the following $G^2$ group, Group $G^2$: —$OR^0$, —$N(R^0)_2$, and a nitrogen-containing heterocyclic group, and $R^9$: lower alkyl which may be substituted with a group selected from —$OR^0$ and —O—CO-lower alkyl, provided that methyl 4-({[N-[(4-fluorophenyl)sulfonyl]-N-(2-methoxyphenyl)glycyl]amino}methyl)benzoate and $N^2$-[(4-chlorophenyl)sulfonyl]-$N^2$-(2,5-difluorophenyl)-N-[4-(1,2,3-thiadiazol-4-yl)benzyl]-D-alaninamide are excluded. The same shall apply hereinafter.]

EFFECT OF THE INVENTION

The compound represented by the formula (I) which is an active ingredient of the present invention or a pharmaceutically acceptable salt thereof has a potent EP1 receptor antagonistic activity, and accordingly, it is useful as a remedy for diseases associated with an EP1 receptor, in particular, a lower urinary tract symptom.

BEST MODE FOR CARRYING OUT THE INVENTION

Hereinafter, the present invention will be described in more detail.

Since the compounds represented by the formula (II), the formula (II-A), the formula (I-A), and the formula (II-B) are included in the compound represented by the formula (I) that is an active ingredient of the present invention, these compounds may be sometimes collectively referred to as the "compound of the present invention".

In the specification, the term "lower" means a linear or branched hydrocarbon chain having 1 to 6 carbon atoms (hereinafter simply referred to as $C_{1-6}$), unless otherwise specifically mentioned.

The "lower alkyl" means $C_{1-6}$ alkyl. Specifically, examples thereof include methyl, ethyl, n-propyl, isopropyl, n-butyl, isobutyl, sec-butyl, tert-butyl, n-pentyl, and n-hexyl. It is preferably alkyl having 1 to 3 carbon atoms, and more preferably methyl, ethyl, or isopropyl.

The "lower alkylene" means a divalent group in which one hydrogen at any position of $C_{1-6}$ alkyl is removed. Specifically, examples thereof include methylene, ethylene, methylmethylene, dimethylmethylene, and trimethylene. Preferred is methylene, ethylene, or trimethylene, and more preferred is methylene or ethylene.

The "lower alkenylene" means $C_{2-6}$ lower alkylene having double bonds at any position. Specifically, examples thereof include vinylene, propenylene, 1-butenylene, and 2-butenylene. Preferred is vinylene.

The "cycloalkane ring" means a $C_{3-10}$ saturated hydrocarbon ring, or it may form a bridged ring. Specifically, examples thereof include cyclopropane, cyclobutane, cyclopentane, cyclohexane, cycloheptane, cyclooctane, adamantane, and norbornane. Preferred is cyclopentane or cyclohexane. The "cycloalkyl" means a ring group consisting of the cycloalkane ring.

The "5- to 7-membered cycloalkene ring" means a $C_{5-7}$ hydrocarbon ring having one double bond. Specifically, examples thereof include cyclopentene, cyclohexene, and cycloheptene. Preferred is cyclopentene or cyclohexene, and more preferred is cyclopentene.

The "halogen" means F, Cl, Br, and I. Preferred is F, Cl, or Br.

The "halogeno-lower alkyl" means the "lower alkyl" as defined above in which any one or more hydrogen atoms are substituted with the same or different one or more "halogen" as defined above. Specifically, examples thereof include fluoromethyl, difluoromethyl, trifluoromethyl, 2,2,2-trifluoroethyl, and pentafluoroethyl. Preferred is trifluoromethyl.

The "aryl" is a $C_{6-14}$ mono-, bi-, and tricyclic aromatic hydrocarbon ring group, and examples thereof include a ring group that is condensed with a $C_{5-7}$ cycloalkene ring group. However, if the $C_{5-7}$ cycloalkene ring is condensed, a bonding arm is positioned on the aromatic ring. Specifically, examples thereof include phenyl, naphthyl, indanyl, tetrahydronaphthyl, and fluorenyl. Preferred is phenyl.

The "hetero ring" is a 4- to 12-membered, mono- or bicyclic saturated or unsaturated ring containing 1 to 4 hetero atoms selected from O, S and N. Examples of the unsaturated ring include an aromatic hetero ring. Furthermore, the ring atom, S or N, may be oxidized to form an oxide or a dioxide. Specifically, examples of the monocyclic ring include azetidine, pyrrolidine, piperidine, piperazine, morpholine, thiomorpholine, azepane, diazepane, oxetane, tetrahydrofuran, tetrahydropyran, 1,3-dioxole, 2,3-dihydro-1,4-dioxine, pyrazolidine, furan, thiophene, pyrrole, imidazole, pyrazole, thiazole, oxazole, isothiazole, isoxazole, triazole, tetrazole, thiadiazole, oxadiazole, pyridine, pyrazine, pyrimidine, pyridazine, triazine, and 2,3-dihydro-1,3-oxazole, and examples of the bicyclic ring include 1,3-benzodioxole, 2,3-dihydro-1,4-benzodioxine, indole, benzofuran, benzothiophene, benzoxazole, benzisoxazole, benzothiazole, benzisothiazole, benzimidazole, indazole, benzotriazole, quinoline, isoquinoline, 1,2,3,4-tetrahydroquinoline, 1,2,3,4-tetrahydroisoquinoline, quinoxaline, quinazoline, and phthalazine. Preferred is a monocyclic hetero ring. The "heterocyclic group" means a ring group consisting of the above-mentioned hetero ring.

The "aromatic hetero ring" means, among the above-mentioned "hetero rings", a ring selected from i) a monocyclic, 5- or 6-membered aromatic hetero ring containing 1 to 4 hetero atoms selected from O, S and N, ii) a bicyclic hetero ring in which the aromatic hetero ring in the above-described i) is condensed (provided that the two aromatic hetero rings to be condensed may be the same as or different from each other), and iii) a bicyclic hetero ring in which the aromatic hetero ring in the above-described i) and a benzene ring or 5- to 7-membered cycloalkane is fused. Specifically, examples thereof include i) pyridine, pyrazine, pyrimidine, pyridazine, triazine, pyrrole, furan, thiophene, imidazole, pyrazole, triazole, tetrazole, oxazole, isoxazole, oxadiazole, thiazole, isothiazole, and thiadiazole, ii) naphthylidine, imidazopyridine, pyrrolopyrimidine, thienopyridine, and thienopyrroline, and iii) benzimidazole, benzofuran, benzothiophene, benzothiadiazole, benzothiazole, benzisothiazole, benzoxazole, benzisoxazole, quinoline, isoquinoline, 5,6,7,8-tetrahydroquinoline, 5,6,7,8-tetrahydroisoquinoline, quinazoline, quinoxaline, phthalazine, indole, isoindole, tetrahydrobenzimidazole, chromane, and indazole. Preferred is the above-described the i) or iii), and more preferred is i) the monocyclic, 5 or 6-membered aromatic hetero ring. The "heteroaryl" means a ring group consisting of the above-mentioned aromatic hetero ring.

The "nitrogen-containing hetero ring" means a hetero ring containing at least one N as a ring-constituting element in the "hetero ring". Specifically, examples thereof include pyrrolidine, piperidine, piperazine, morpholine, thiomorpholine, azepane, diazepane, 1,2,3,4-tetrahydroquinoline, 1,2,3,4-tetrahydroisoquinoline, pyridine, pyrazine, pyrimidine, pyridazine, triazine, pyrrole, imidazole, pyrazole, triazole, tetrazole, oxazole, isoxazole, oxadiazole, thiazole, isothiazole, thiadiazole, benzimidazole, benzothiadiazole, benzothiazole, benzisothiazole, benzoxazole, benzisoxazole, quinoline, isoquinoline, 5,6,7,8-tetrahydroquinoline, 5,6,7,8- tetrahydroisoquinoline, quinazoline, quinoxaline, phthalazine, indole, isoindole, tetrahydrobenzimidazole, and indazole. The "nitrogen-containing heterocyclic group" means a ring group consisting of the above-mentioned nitrogen-containing hetero ring.

The "—$CO_2H$ or a biological equivalent" is a carboxylic acid, or the atom or moiety having an electrically or sterically equivalent configuration and having a common biological property thereto. These include a so-called carboxylic acid bioisostere that is usually used by a skilled person in the art, a protected carboxyl group, and a prodrug of a carboxylic acid, including, for example, a carboxylic acid, a carboxylic acid ester, hydroxamic acid (—CO—NH—OH), acylcyanamide (—CO—NH—CN), acylsulfonamide (—CO—NH—$SO_2$—R or —$SO_2$—NH—CO—R), or tetrazole, 5-oxo-1,2,4-oxadiazole, 3-hydroxyisoxazole, 5-oxo-1,2,4-thiadiazole, 3-hydroxy-1,2,5-thiadiazole, and 3-hydroxy-γ-pyrone. Preferred is carboxylic acid, acyl sulfonamide, tetrazole, or 5-oxo-1,2,4-oxadiazole, and more preferred is carboxylic acid or acyl sulfonamide.

In addition, examples of the R in acyl sulfonamide (—CO—NH—$SO_2$—R or —$SO_2$—NH—CO—R) include lower alkyl which may be substituted with a substituent selected from the group consisting of —OH, —O-lower alkyl, and —O—CO-lower alkyl.

The expression "may be substituted" means that "is not substituted", or "is substituted with the same or different 1 to 5 substituents, preferably 1 to 2 substituents".

Furthermore, in a case where a plurality of the groups exist as in $R^0$ in —$N(R^0)_2$, or the like, each group ($R^0$ in this case) may be the same as or different from each other.

Examples of the substituent that is acceptable for the "aryl" and the "heteroaryl" in the "aryl which may be substituted", the "heteroaryl which may be substituted", the "—O-aryl which may be substituted", and the "—O-heteroaryl which may be substituted" of $R^1$ to $R^4$ include a group selected from the following Group $G^3$.

Group $G^3$: halogen, lower alkyl, halogeno-lower alkyl, —$OR^0$, —O-halogeno-lower alkyl, —$NO_2$, and —CN.

Examples of the substituent that is acceptable for the "aryl" and the "heteroaryl" in the "-lower alkylene-aryl which may be substituted", the "-lower alkylene-heteroaryl which may be substituted", the "-lower alkylene-O-aryl which may be substituted", and the "-lower alkylene-O-heteroaryl which may be substituted" of $R^B$ include a group selected from the Group $G^3$, —O-benzyl, —$N(R^0)_2$, —$N(R^0)$—CO-lower alkyl, —$N(R^0)$—$SO_2$-lower alkyl, —$S(O)_n$-lower alkyl, —$SO_2$—$N(R^0)_2$, phenyl which may be substituted with a group selected from the Group $G^3$, -lower alkylene-$OR^0$, or —Y—Z.

Preferred embodiments in the active ingredient (I) of the present invention are as follows.

(1-a) $L^1$ is preferably a single bond.
(2-a) $L^2$ is preferably methylene.
(3-a) Ring A is preferably a benzene ring.
(4-a) $R^1$ and $R^2$ are preferably the same as or different from each other, and are each halogen, lower alkyl, halogeno-lower alkyl, —$OR^0$, —O-halogeno-lower alkyl, —CN, or —$NO_2$, more preferably, halogen, lower alkyl, or —$OR^0$, and even more preferably, Cl, Br, methyl, ethyl, or methoxy. Furthermore, a position to be substituted on a benzene ring of $R^1$ and $R^2$, preferably, a 2- or 3-position, relative to a position to which $L^1$ is bonded to, is substituted with the same or different groups as described above.
(5-a) $R^3$ and $R^4$ are preferably the same as or different from each other, and are each $R^0$, halogen, —CN, halogeno-lower alkyl, —CO-lower alkyl, or -lower alkylene-$OR^0$, more preferably, $R^0$, halogen, —CN, or halogeno-lower alkyl, and even more preferably, H, methyl, ethyl, Br, Cl, F, —CN, or trifluoromethyl.

Even more preferably, either of $R^3$ and $R^4$ is H or F, and the other is the group as described above, which is other than H and F.

(6-a) $R^4$ is preferably H.
(7-a) $R^B$ is preferably -lower alkylene-aryl which may be substituted, or -lower alkylene-heteroaryl which may be substituted, and more preferably, -methylene-aryl which may be substituted, or -methylene-heteroaryl which may be substituted. Here, the aryl is preferably phenyl, and the heteroaryl is preferably thienyl, furyl, pyridyl, or pyrimidinyl. Furthermore, the aryl which may be substituted and the heteroaryl which may be substituted is preferably aryl and heteroaryl that are each not substituted, or aryl and heteroaryl that are each substituted with a group selected from the group consisting of halogen, —$OR^0$, —O-halogeno-lower alkyl, —CN, -lower alkylene-$OR^0$, —$N(R^0)$—CO-lower alkyl, and —Y—Z, and more preferably, aryl and heteroaryl that are each not substituted, or aryl and heteroaryl that are each substituted with a group selected from the group consisting of —$OR^0$ and —Y—Z.

A particularly preferred embodiment of the active ingredient (I) of the present invention is a compound obtained by the combination of each preferable group as described in (1-a) to (7-a) as above. Another preferred embodiment is the compound represented by the formula (II).

The preferred embodiments in the compound (II) of the present invention are as follows.

(1-b) $L^1$ is preferably a single bond.
(2-b) $L^2$ is preferably methylene.
(3-b) Ring A is preferably a benzene ring.
(4-b) $R^1$ and $R^2$ are preferably the same as or different from each other, and are each halogen, lower alkyl, halogeno-lower alkyl, —$OR^0$, —O-halogeno-lower alkyl, or —CN, more preferably, halogen, lower alkyl, or —$OR^0$, and even more preferably, Cl, Br, methyl, ethyl, or methoxy. Furthermore, a position to be substituted on a benzene ring of $R^1$ and $R^2$, preferably, a 2- or 3-position, relative to a position to which $L^1$ is bonded to, is substituted with the same or different groups as described above.
(5-b) $R^3$ and $R^4$ are preferably the same as or different from each other, and are each $R^0$, halogen, halogeno-lower alkyl, —$OR^0$, —O-halogeno-lower alkyl, or —CN, more preferably, $R^0$, halogen, halogeno-lower alkyl, or —CN, and even more preferably, H, methyl, ethyl, Br, Cl, F, —CN, or trifluoromethyl.

Even more preferably, either of $R^3$ and $R^4$ is H or F, and the other is the group as described above, which is other than H and F.

(6-b) $L^3$ is preferably methylene or ethylene, and more preferably, methylene.
(7-b) X is preferably a single bond.
(8-b) Ring B is preferably a benzene ring, a thiophene ring, a furan ring, an oxazole ring, a pyridine ring, or a pyrimidine ring, and more preferably, a benzene ring, a thiophene ring, or an oxazole ring.
(9-b) $R^5$ and $R^6$ are preferably the same as or different from each other, and are each $R^0$, halogen, or —$OR^0$, more preferably H or halogen, and even more preferably, both of $R^5$ and $R^6$ are H, or either of $R^5$ and $R^6$ is H, and the other is F.
(10-b) Y is preferably i) a single bond, ethylene, vinylene, propenylene, —O-methylene, or —O-methylmethylene in a case where Z is —$CO_2H$ or a biological equivalent, or —$CONR^7R^8$; or ii) a single bond in a case where Z is a nitrogen-containing heterocyclic group which may be substituted with a substituent selected from the group $G^1$.

(11-b) Z is preferably —$CO_2H$ or a biological equivalent, more preferably, —$CO_2H$, acyl sulfonamide, tetrazole, or 5-oxo-1,2,4-oxadiazole, and even more preferably, —$CO_2H$ or —$CONH$—$SO_2Me$.

A particularly preferred embodiment of the active ingredient (II) of the present invention is a compound obtained by the combination of each preferable group as described in (1-b) to (11'-b) as above.

Moreover, the preferred embodiments in the compound (II-B) of the present invention are as follows.

(1) $L^1$ is preferably a single bond.
(2) $L^2$ is preferably methylene.
(3) Ring A is preferably a benzene ring.
(4) $R^1$ and $R^2$ are preferably the same as or different from each other, and are each halogen, lower alkyl, halogeno-lower alkyl, —$OR^0$, —O-halogeno-lower alkyl, —CN, or —$NO_2$, and more preferably, halogen, lower alkyl, or —$OR^0$. Furthermore, a position to be substituted on a benzene ring of $R^1$ and $R^2$, preferably, an ortho- or meta-position, relative to a position to which $L^1$ is bonded to, is substituted with the same or different groups as described above.
(5) $R^3$ and $R^4$ are preferably the same as or different from each other, and are each H, lower alkyl, halogen, —CN, halogeno-lower alkyl, —CO-lower alkyl, or -lower alkylene-$OR^0$, and more preferably, methyl, ethyl, Br, Cl, —CN, trifluoromethyl, acetyl, or hydroxymethyl. Even more preferably, either of $R^3$ and $R^4$ is H, and the other is the group as described above, which is other than H.
(6) $L^3$ is preferably methylene or ethylene, and more preferably methylene.
(7) X is preferably a single bond.
(8) Ring B is preferably a benzene ring, a thiophene ring, or a pyridine ring, and more preferably, a benzene ring.
(9) $R^5$ and $R^6$ are preferably the same as or different from each other, and are each H or —O-lower alkyl, and more preferably, both of $R^5$ and $R^6$ are H, or either of $R^5$ and $R^6$ is H, and the other is —O-lower alkyl.
(10) Y is preferably i) a single bond, ethylene, vinylene or —O-methylene in a case where Z is —$CO_2R^0$, —$CONR^7R^8$, or —$CONH$—$SO_2$—$R^9$; or ii) a single bond in a case where Z is a nitrogen-containing heterocyclic group which may be substituted with a substituent selected from the group $G^1$.
(11) Z is preferably $CO_2H$, —$CONH$—$(CH_2)_2OH$, —$CONH$—$(CH_2)_2NMe_2$, —$CONH$—$SO_2Me$, or —$CONH$—$SO_2$—$(CH_2)_3OH$.

A particularly preferred embodiment of the active ingredient (II) of the present invention is a compound obtained by the combination of each preferable group as described in (1) to (11) as above.

The compound of the present invention may sometimes exist in the form of a geometrical isomer or a tautomer, depending on the kind of the substituents. The present invention includes an isolated form and a mixture of these isomers.

The compound of the present invention may have asymmetric carbons, and correspondingly, exist in the form of optical isomers such as an (R)-form and an (S)-form.

The compound of the present invention includes both of a mixture and an isolated form of these optical isomers.

Furthermore, the compound of the present invention includes a "pharmaceutically acceptable prodrugs". The "pharmaceutically acceptable prodrug" is a compound having a group which is converted into $NH_2$, OH, $CO_2H$, or the like of the present invention by solvolysis or under a physiological condition. Examples of the group capable of forming a prodrug include the groups as described in "Progress in Medicine", Life Science Medical, vol. 5, 2157-2161 (1985), and "Iyakuhin no Kaihatsu (Development of Drugs) (Hirokawa Shoten, vol. 7), Bunshi Sekkei (Molecular Design)", 163-198 (1990).

The compound of the present invention may form a salt with an acid or a base, depending on the kind of substituents. These salts are the pharmaceutically acceptable salts, and specific examples thereof include acid addition salts with inorganic acids such as hydrochloric acid, hydrobromic acid, hydroiodic acid, sulfuric acid, nitric acid, and phosphoric acid; with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, and glutamic acid; with inorganic bases such as sodium, potassium, magnesium, calcium, and aluminum; and with organic bases such as methylamine, ethylamine, ethanolamine, lysine, and ornithine, and ammonium salts.

In addition, the present invention also includes various hydrates, solvates, and polymorphic substances of the compound or a salt thereof of the present invention.

(Production Processes)

The compound of the present invention and a pharmaceutically acceptable salt thereof can be prepared by applying various known synthetic methods, by the use of the characteristics based on their basic skeltons or the kind of the substituents. Further, depending on the kind of the functional groups, it is sometimes effective from the viewpoint of the preparation techniques to protect the functional group with an appropriate protecting group, or to replace it by a group which may be easily converted into the functional group, during the steps of from starting materials to intermediates. Examples of such a functional group include an amino group, a hydroxyl group, and a carboxyl group, and examples of such a protecting group include those as described in "Protective Groups in Organic Synthesis", edited by T. W. Greene and P. G. M. Wuts, (USA), $3^{rd}$ edition, John Wiley & Sons, 1999, which may be optionally selected and used in response to the reaction conditions. By such a method, a desired compound can be obtained by introducing the protecting group to carry out the reaction, and then, if desired, removing the protecting group or converting it into a desired group.

In addition, a prodrug of the compound of the present invention can be prepared by introducing a specific group during the steps for from starting materials to intermediates, in a similar way to the aforementioned protecting groups, or by carrying out the reaction with the obtained compound of the present invention. The reaction may be carried out by employing a method known to a skilled person in the art, such as common esterification, amidation, and dehydration.

Hereinbelow, the representative production processes of the compounds of the present invention are described. Further, the production processes of the present invention are not limited to the examples as shown below.

(Production Process 1)

[Chem. 12]

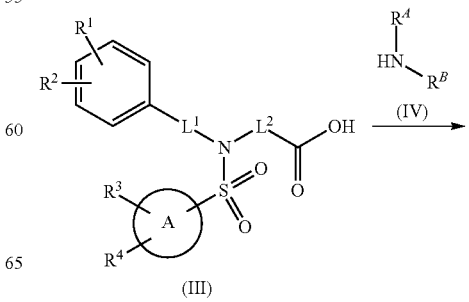

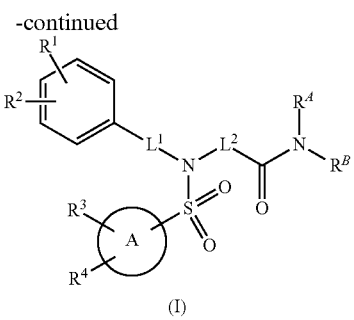

(I)

This step is a process for preparing the compound (I) of the present invention by reacting a compound (IV) with a compound (III) or a reactive derivative thereof. Examples of the reactive derivative include an acid halide (acid chloride, acid bromide or the like), an acid anhydride (mixed acid anhydrides obtained by the reaction with ethyl chlorocarbonate, benzyl chlorocarbonate, phenyl chlorocarbonate, p-toluenesulfonic acid, isovaleric acid or the like, or symmetric acid anhydrides), an active ester (an ester which may be prepared using a phenol which may be substituted with an electron-withdrawing group (e.g., a nitro group, a fluorine atom or the like), 1-hydroxybenzotriazole (HOBt), N-hydroxysuccinimide (HONSu) or the like), a lower alkyl ester, and an acid azide. These reactive derivatives can be produced by conventional methods. The reaction can be carried out using equimolar of the carboxylic acid compound (III) or a reactive derivative thereof and the compound (IV), or one of them in excess amount, from under cooling to heating in a reaction-inert solvent such as aromatic hydrocarbons, halogenated hydrocarbons, ethers, N,N-dimethylformamide (DMF), N,N-dimethylacetamide (DMA), N-methylpyrrolidone (NMP), ethyl acetate, and acetonitrile. Depending on the kind of the reactive derivatives, it is sometimes advantageous in advancing the reaction smoothly to carry out the reaction in the presence of a base (preferably, triethylamine, diisopropylethylamine, N-methylmorpholine, pyridine, 4-(N,N-dimethylamino)pyridine, or the like). Pyridine can also serve as a solvent.

When a free carboxylic acid is used, it is desirable to use a condensing agent (N,N'-dicyclohexylcarbodiimide (DCC), 1-[3-(dimethylamino)propyl]-3-ethylcarbodiimide (WSC), 1,1'-carbonyldiimidazole (CDI), N,N'-disuccinimidyl carbonate, a Bop reagent (manufactured by Aldrich, USA), 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), diphenylphosphoric acid azide (DPPA), phosphorus oxychloride, phosphorus trichloride, triphenylphosphine/N-bromosuccinimide or the like), and if desired, an additive (for example, HONSu and HOBt).

(Production Process 2)

[Chem. 13]

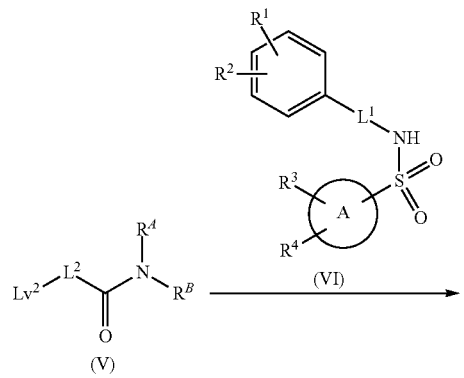

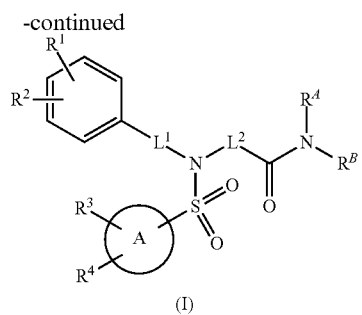

(I)

(wherein $Lv^2$ represents a leaving group. The same shall apply hereinafter.)

This step is a process for preparing the compound (I) of the present invention by alkylating a compound (VI) to a compound (V) with a leaving group. The leaving group represented by $Lv^2$ may be any leaving group which is generally used in the nucleophilic substitution reaction, and, as for this, halogen such as chloro and bromo; sulfonyloxy such as methanesulfonyloxy, p-toluenesulfonyloxy, and trifluoromethanesulfonyloxy; sulfonyl such as lower alkylsulfonyl and arylsulfonyl; and the like may be suitably used. As the alkylation reaction of this step, the alkylation generally used by those skilled in the art may be employed. For example, this may be carried out from at room temperature to heat under reflux without solvent or in a reaction-inert solvent such as the aforementioned aromatic hydrocarbons such as benzene, toluene, and xylene, esters such as ethyl acetate, ethers such as diethyl ether, tetrahydrofuran (THF), and dioxane, halogenated hydrocarbons such as dichloromethane, 1,2-dichloroethane, and chloroform, DMF, DMA, NMP, dimethyl sulfoxide (DMSO), and acetonitrile, or in a solvent such as alcohols or the like. Depending on the compounds, it is sometimes advantageous for smoothly advancing the reaction to carry out the reaction in the presence of an organic base (triethylamine, diisopropylethylamine, N-methylmorpholine, pyridine, 4-(N,N-dimethylamino)pyridine or the like is suitably used), or a metal salt base (potassium carbonate, cesium carbonate, sodium hydroxide, potassium hydroxide, sodium hydride, potassium tert-butoxide or the like is suitably used).

(Production Process 3)

[Chem. 14]

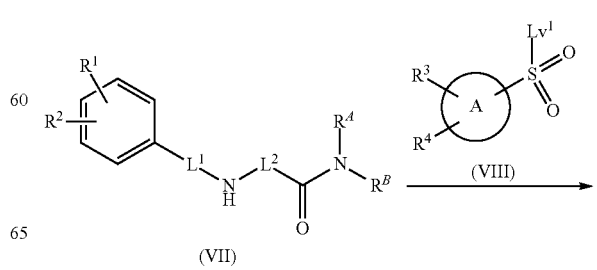

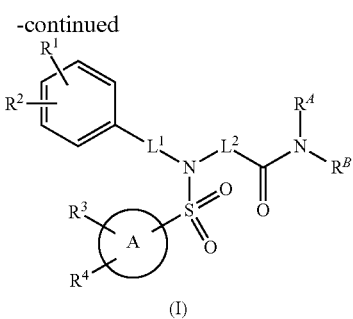

(I)

(wherein $Lv^1$ represents a leaving group. The same shall apply hereinafter.)

This step is a process for preparing the compound (I) of the present invention by sulfonylating the compound (VII) by a compound (VIII). As the leaving group of $Lv^1$, halogen such as chloro and bromo is suitably used. The reaction can be carried out, for example, by employing the sulfonylation condition described in the aforementioned "Protective Groups in Organic Synthesis". Specifically, the reaction can be carried out without a solvent, or in a solvent such as THF, methylene chloride, and acetonitrile, in the presence of a base such as triethylamine and pyridine if necessary, from under cooling to heat under reflux.

(Production Process 4)

[Chem. 15]

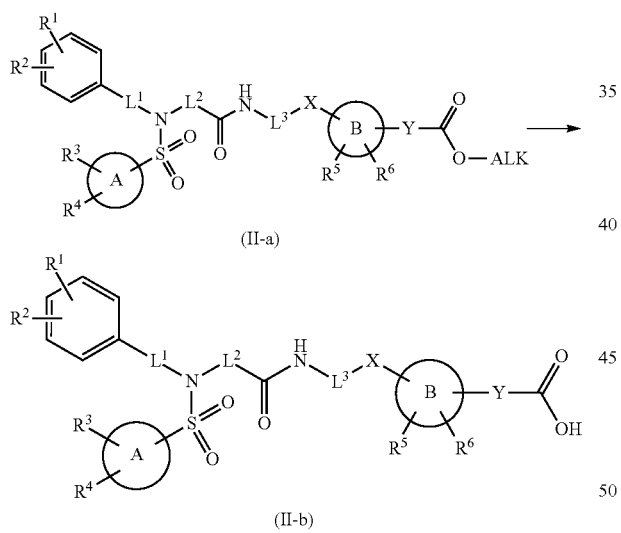

(wherein ALK represents lower alkyl. The same shall apply hereinafter.)

This step is a process for preparing the compound (II-b) of the present invention in which Z is carboxyl, by hydrolysis of the compound (II-a) of the present invention in which Z is an ester. The hydrolysis reaction of this step can be carried out, for example, in accordance with the deprotection reaction described in the aforementioned "Protective Groups in Organic Synthesis".

In addition, some compounds represented by the formulae (I) and (II) can be prepared from the compounds of the present invention obtained by the aforementioned methods and variations thereof, or by any combination of well-known processes that can be usually employed by a skilled person in the art, such as alkylation, acylation, substitution reaction, oxidation, reduction, hydrolysis, and deprotection.

The starting material compounds used in the preparation of the compounds of the present invention can be prepared, for example, by using the methods as described below, well-known methods, or variations thereof.

(Starting Material Synthesis 1)

[Chem. 16]

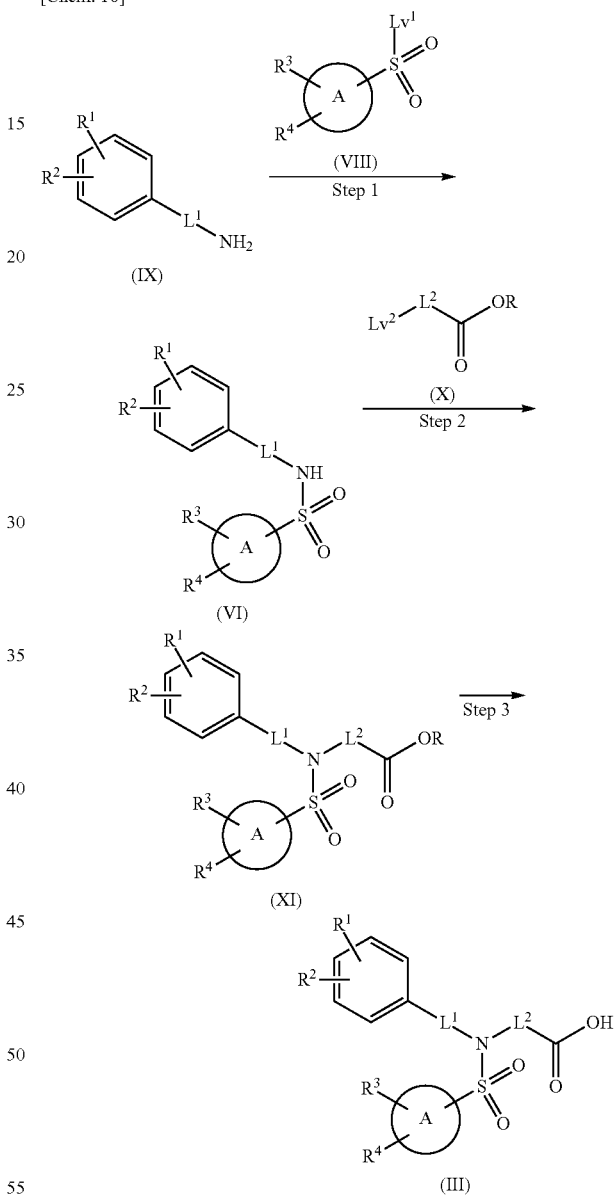

First Step

This step is a process for preparing a compound (VI) by sulfonylating the compound (IX) by a compound (VIII). The sulfonylation of this step can be carried out in the same manner as the sulfonylation in Production Process 3.

Second Step

This step is a process for preparing a compound (XI) by alkylating the compound (VI) by a compound (X) containing a leaving group. The alkylation of this step can be carried out in the same manner as the alkylation in Production Process 2.

Third Step

This step is a process for preparing a compound (III) from a compound (XI) by hydrolysis. The hydrolysis reaction of this step can be carried out in the same manner as the hydrolysis reaction in Production Process 4.

(Starting Material Synthesis 2)

[Chem. 17]

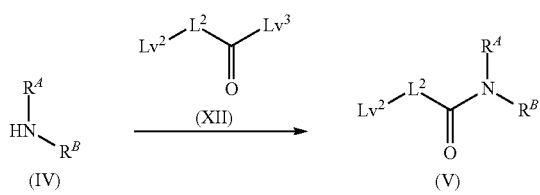

(wherein $Lv^3$ represents a leaving group. The same shall apply hereinafter.)

This step is a process for preparing a compound (V) by acylating the compound (IV) by a compound (XII) containing a leaving group. As the leaving group of $Lv^3$, halogen such as chloro and bromo is suitably used. For example, the reaction can be carried out by employing the acylation condition described in the aforementioned "Protective Groups in Organic Synthesis". Specifically, it can be carried out without a solvent, or in a solvent such as THF, methylene chloride, and acetonitrile, in the presence of a base such as triethylamine and pyridine if necessary, from under cooling to heat under reflux.

(Starting Material Synthesis 3)

[Chem. 18]

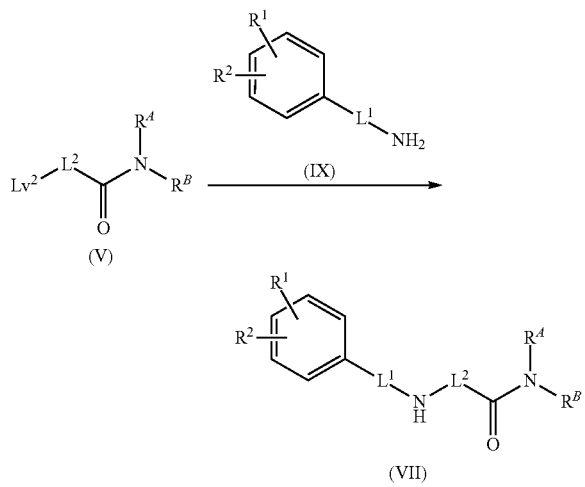

This step is a process for preparing a compound (VII) by alkylating the compound (IX) by the compound (V) containing a leaving group. The alkylation of this step can be carried out in the same manner as the alkylation in Production Process 2.

The reaction products obtained by each of Production Processes can be isolated and purified as their free compounds, or salts or various solvates thereof, such as hydrates. The salts can be prepared after carrying out a conventional salt formation treatment.

The isolation and purification can be carried out by employing common chemical operations such as extraction, concentration, removal by distillation, crystallization, filtration, recrystallization, and various chromatography techniques.

Various isomers can be isolated by conventional method making use of the differences in physicochemical properties among the isomers. For example, the optical isomers can be separated by general optical resolutions, for example, by fractional crystallization, chromatography, or the like. In addition, the optical isomers can also be prepared from appropriate starting material compounds that are optically active.

The effects of the compounds of the present invention were confirmed by the following tests.

1. Experiment to Measure a Receptor Antagonistic Activity Using Cells Expressing an EP1 Receptor HEK293 cells (American Type Culture Collection) that stably expressed rat EP1 receptors were dispensed onto a 96-well poly-D-lysine-coated plate (Product Name: Biocoat, PDL96W black/clear, Nippon Becton Dickinson) to a $2\times10^4$ cells/well at the day before the experiment, and incubated overnight at 37° C. under 5% carbon dioxide ($CO_2$) in a culture medium containing 10% fetal bovine serum (FBS) (Product Name: DMEM, Invitrogen Corporation). The culture medium was replaced by a loading buffer (a washing solution containing a 4 μM fluorescent indicator (Product Name: Fluo3-AM, Tong Ren Tang Technologies Co. Ltd.):a Hank's balanced salt solution)(HBSS), 20 mM 2-[4-(2-hydroxyethyl)-1-piperazinyl]ethanesulfonic acid (HEPES)-sodium hydroxide (NaOH), 2.5 mM Probenecid, 0.1% bovine serum albumin (BSA)), and left to stand at room temperature for 3 hours, and the cells were washed using a plate washer in which a washing solution had been set up (Product Name: ELx405, BIO-TEK instrument Corporation). The compound that had been preliminarily dissolved and diluted in a washing solution was added thereto, and set up in a system for measuring a calcium (Ca) concentration in a cell (Product Name: FLIPR, Molecular Devices Corporation). After 5 minutes, $PGE_2$ was added to a final concentration of 100 nM, and the change in Ca concentrations in cells was measured. A difference between a maximum value and a minimum value in Ca concentrations in cells was determined, and kept as measurement data. With a response upon addition of 100 nM $PGE_2$ being set at 0%, and a response upon addition of a buffer being set at 100%, the concentration causing 50% inhibition was determined as an $IC_{50}$ value.

The results are shown in the following Table 1. In the table, Pre represents Preparative Example No. as described later, and Ex represent Example No. as described later.

TABLE 1

| Compound | $IC_{50}$ (nM) |
| --- | --- |
| Pre1 | 16 |
| Pre15 | 12 |
| Ex7 | 1.6 |
| Ex16 | 2.4 |
| Ex20 | 1.4 |
| Ex24 | 1.0 |
| Ex26 | 2.5 |
| Ex38 | 1.5 |
| Ex40 | 0.72 |
| Ex74 | 1.0 |

(2) Receptor Binding Test Using EP1 Receptor-Expressing Cells

A signal peptide (MKTIIALSYIFCLVFA: SEQ ID NO: 1) and a FLAG sequence (DYKDDDDK: SEQ ID NO: 2) were introduced at the N-terminus of a rat EP1 receptor, followed by subcloning into an expression vector (Product Name:

pCEP4, Invitrogen Corporation). An HEK293EBNA cell (American Type Culture Collection) was transfected with the rat EP1 expression vector using a transfection regent (Product Name: Fugene-6, Roche-Diagnostics, K.K), and then cultured for 2 days in a medium containing 10% FBS (Product Name: DMEM, Invitrogen Corporation) at 37° C. under 5% $CO_2$. After culturing, the cells were recovered, treated with a cell lysate (20 mM Tris(hydroxymethyl)aminomethane (Tris) buffer pH7.5, 5 mM ethylene diaminetetraacetic acid (EDTA)), and ultracentrifuged (23,000 revolution, 25 minutes×2) for a rough preparation of a membrane sample.

A reaction solution containing the prepared membrane sample (15 µg) and $^3$H-$PGE_2$ (150 µl, composition: 10 mM 2-(N-morpholino)ethanesulfonic acid (MES)/potassium hydroxide(KOH) pH6.0, 1 mM EDTA, 10 mM magnesium chloride ($MgCl_2$), 0.02% 3-[(3-Cholamidopropyl)dimethylammonio] propanesulfonate (CHAPS)) was incubated at room temperature for 1 hour. The reaction was terminated with an ice-cooled buffer, and suction-filtered under reduced pressure to trap the bound $^3$H-$PGE_2$ to a glass fiber filter (Product Name: UNIFILTER-96, GF/B, PerkinElmer Japan Co., Ltd.), so as to measure the radioactivity of the binding with a microplate scintillation counter (Product Name: TopCount, Packard) using Microscinti (Product Name: Microscinti 20, PerkElmer Japan Co., Ltd.).

The dissociation constant (Kd) and the maximum binding (Bmax) were determined using Scatchard plot (Annals of the New York Academy of Science, US, volume 51, page 660, 1949). Nonspecific bindings were determined as bindings in the presence of an excessive amount (2.5 µM) of label-free $PGE_2$. The assessment of inhibitory effect on $^3$H-$PGE_2$ binding by the compound was carried out by adding 2.5 nM $^3$H-$PGE_2$ and the compound.

The inhibition constant Ki(nM) for each compound was obtained using the following formula:

$$Ki=IC_{50}/(1+([C]/Kd))$$

wherein [C] represents the concentration of $^3$H-$PGE_2$ employed in a reaction system.

The results are shown in Table 2.

TABLE 2

| Compound | Ki (nM) |
|---|---|
| Pre1 | 0.68 |
| Ex7 | 0.57 |
| Ex16 | 1.00 |
| Ex20 | 0.74 |
| Ex38 | 0.48 |
| Ex40 | 0.33 |
| Ex74 | 0.35 |

(3) Effects on Rats with Acetic Acid-Induced Urinary Frequency

The anti-pollakiuria action of the compound was assessed using a pathological model. It has been reported that applying acetic acid to rat urinary bladder damages the bladder mucosa, thereby activating the nociceptive stimulus transmittance afferent (The Journal of Neuroscience, US, 12 (12): p. 4878-89). Since urinary frequency is induced by treating intra-bladder with acetic acid, it is possible to assess remedial effects of the compound against the symptoms.

For the experiment, male Wistar rats (Charles River Laboratories) weighing between 200 and 450 g were used. The urinary bladder was exteriorized by median abdominal incision under pentobarbital anesthesia (50 mg/kg, i.p.), and residual urine in the urinary bladder was removed with a syringe equipped with a 27G needle. Thereafter, 0.5 to 0.7 mL of a 1% acetic acid solution was injected into the bladder and the wound was closed. 2 days after, further experiment was carried out. Rats were placed in metabolic cages for acclimation for 1 hour, and then the test drug was injected. Immediately thereafter, change in the amount of urine output was sequentially measured for 6 hours. Total urine output was divided by total urination incidents to calculate the effective bladder capacity. As a result, it was noted that the effective bladder capacity of the group the bladder of which had been treated with acetic acid was decreased as compared to that of the sham-operated group, and thus showed symptoms of urinary frequency. On the other hand, the compound of the invention highly improved the urinary frequency symptom.

From the test results (1) to (3), it was confirmed that the compound of the present invention has a potent EP1 receptor antagonistic activity, and that it greatly improves the urinary frequency symptom.

Thus, the compound of the present invention is effective as a remedy for EP1 receptor-related diseases, especially for a lower urinary tract symptom.

Examples of diseases that cause 'a lower urinary tract symptom' in the present invention include overactive bladder, BPH (benign prostatic hyperplasia), bladder neck contracture, cystitis, prostatitis and the like.

The 'a lower urinary tract symptom' in the present invention include urinary storage symptoms such as diurnal urinary frequency, nocturnal urinary frequency, urinary urgency, and urinary urge incontinence; voiding symptoms such as weak urination, interrupted urine flow, and delayed urination; post-urination symptoms such as residual urine sensation; and genital/lower abdominal pain such as bladder pain, urethral pain, perineal pain, scrotal pain, and pelvic pain. Furthermore, urinary storage symptoms, voiding symptoms and post-urination symptoms include urinary storage symptoms, voiding symptoms and post-urination symptoms associated with benign prostatic hyperplasia. In addition, urinary storage symptoms include urinary storage symptoms associated with overactive bladder, cystitis and prostatitis.

The pharmaceutical composition containing at least one or more kinds of the compound or a salt thereof of the present invention as an active ingredient is prepared by using pharmaceutical carriers, excipients, other additives and the like, usually used in the field according to a usual method.

Therapeutic administration may be made in any one form for either oral administration via tablets, pills, capsules, granules, powders, liquids, etc., or for parenteral administration via injections for intravenous injection and intramuscular injection, suppositories, transdermal preparations, transnasal preparations, inhalers, or the like. The dose is appropriately decided in response to an individual case by taking the symptoms, the age and sex of the subject, and the like into consideration, but is usually from about 0.001 mg/kg to about 100 mg/kg per day per adult in the case of oral administration, and this is administered in one portion or dividing it into 2 to 4 portions. Also, in the case of intravenous administration, this is administered usually within the range of from 0.0001 mg/kg to 10 mg/kg per day per adult, once a day or two or more times a day. In the case of transnasal administration, this is administered usually within the range of from 0.0001 mg/kg to 10 mg/kg per day per adult, once a day or two or more times a day. In addition, in the case of inhaler, this is administered usually within the range of from 0.0001 mg/kg to 1 mg/kg per adult, once a day or several times a day.

Regarding the solid composition according to the present invention for oral administration, tablets, powders, granules, or the like are used. In such a solid composition, one or more active substances are mixed with at least one inactive excipient such as lactose, mannitol, glucose, hydroxypropylcellulose, microcrystalline cellulose, starch, polyvinyl pyrrolidone, and magnesium alminometasilicate. In a conventional method, the composition may contain inactive additives such as lubricants such as magnesium stearate, disintegrating agents such as carboxymethylstarch sodium, and solubilization assisting agents. As occasion demands, tablets or pills may be coated with sugar, or a gastric or enteric coating agent, if necessary.

The liquid composition for oral administration includes pharmaceutically acceptable emulsions, solutions, suspensions, syrups, elixirs, and the like, and contains commonly used inert solvents such as purified water or ethanol. In addition to the inert solvent, this composition may contain auxiliary agents such as solubilization assisting agents, moistening agents, and suspending agents, sweeteners, correctives, aromatics and antiseptics.

Injections for parenteral administration include aseptic aqueous or non-aqueous solutions, suspensions and emulsions. As the aqueous solvent, for example, distilled water for injection and physiological saline are included. Examples of the non-aqueous solvent include propylene glycol, polyethylene glycol, plant oils such as olive oil, alcohols such as ethanol, and Polysorbate 80 (Pharmacopeia). Such a composition may further contain tonicity agents, antiseptics, moistening agents, emulsifying agents, dispersing agents, stabilizing agents, and solubilization assisting agents. These are sterilized, for example, by filtration through a bacteria retaining filter, blending of germicides or irradiation. In addition, these can also be used by producing a sterile solid composition, and dissolving or suspending it in sterile water or a sterile solvent for injection prior to their use.

The drug for external use may include ointments, plasters, creams, jellies, patches, sprays, lotions, eye-drops, eye ointments, and the like. The drug contains generally used ointment bases, lotion bases, aqueous or non-aqueous solutions, suspensions, emulsions, and the like Examples of the ointment bases or lotion bases include polyethylene glycol, propylene glycol, white vaseline, bleached bee wax, polyoxyethylene hydrogenated castor oil, glyceryl monostearate, stearyl alcohol, cetyl alcohol, lauromacrogol, and sorbitan sesquioleate.

Regarding transmucosal agents such as inhalers and transnasal agents, those in the form of solid, liquid or semi-solid state are used, and may be produced in accordance with a conventionally known method. For example, excipients such as lactose and starch, and also pH adjusting agents, antiseptics, surfactants, lubricants, stabilizers, thickeners, and the like may be optionally added thereto, if necessary. For their administration, appropriate devices for inhalation or insufflation may be used. For example, a compound may be administered alone or as a powder of formulated mixture, or as solutions or suspensions by combining it with pharmaceutically acceptable carriers, using conventionally known devices or sprayers, such as measured-dose inhalers. The dry powder inhalers or the like may be for single or multiple administration use, and dry powders or powder-containing capsules may be used. Alternatively, these may be in the form such as a high pressure aerosol spray or the like which uses an appropriate propellant, for example, a suitable gas such as chlorofluoroalkane, hydrofluoroalkane, and carbon dioxide.

PREPARATIVE EXAMPLES AND EXAMPLES

Hereinbelow, the methods for preparing the compound of the present invention will be described in more detail with reference to Preparative Examples and Examples of the compound of the present invention, but the present invention is not limited to these Preparative Examples and Examples. Furthermore, the methods for preparing the starting material compounds for the compound of the present invention will be described in Reference Examples.

In this regard, the symbols in Reference Examples, Preparative Examples, and Examples have the following meanings (the same shall apply hereinafter.).

Rf: Reference Example No., Pre: Preparative Example No., Ex: Example No., Str: structural formula, Syn: production process (the numeral shows that it was produced using a corresponding starting material, similar to the case of an Example compound having its number as the Example No. In a case where R is attached before the number, the numeral shows that it was produced using a corresponding starting material, similar to the case of a Reference Example compound having its number as the Reference Example No., and in a case where P is attached before the number, the numeral shows that it was produced using a corresponding starting material, similar to the case of a Preparative Example compound having its number as the Preparative Example No. A case where a plurality of production processes are described, for example, by using * as in P1*1, indicates that it was produced by carrying out the reactions in those order starting from the left one or the upper one, using a corresponding starting material), Dat: Physicochemical data (EI: EI-MS ([M]$^+$); EP: ESI-MS (Pos) (in a case of no description, [M+H]$^+$); EN: ESI-MS (Neg)([M−H]$^-$); API: API-MS (Pos) (in a case of no description, [M+H]$^+$); FP: FAB-MS (Pos) (in a case of no description, [M+H]$^+$); FN: FAB-MS (Neg) (in a case of no description, [M−H]$^-$); NMR1: δ (ppm) of the peaks in $^1$H-NMR using DMSO-d$_6$; Me: methyl, Et: ethyl, nPr: n-propyl, iPr: isopropyl, Bn: benzyl, Ac: acetyl, Ms: methanesulfonyl.

Reference Example 1

18.7 g of 3-chloro-2-methylaniline was dissolved in 120 mL of pyridine, and 22.9 g of p-toluene sulfonylchloride was added portionwise thereto over 30 minutes, followed by stirring at room temperature overnight. The reaction liquid was concentrated under reduced pressure, and to the obtained residue was added water, followed by extraction with ethyl acetate. The organic layer was washed with 1 M hydrochloric acid, saturated brine, an aqueous saturated sodium hydrogen carbonate solution, and saturated brine, and then dried over anhydrous sodium sulfate. The solvent was evaporated under reduced pressure to obtain 34.6 g of N-(3-chloro-2-methylphenyl)-4-methylbenzenesulfonamide.

Reference Example 2

34.5 g of N-(3-chloro-2-methylphenyl)-4-methylbenzenesulfonamide was dissolved in 232 mL of DMF, and 21.4 g of ethyl bromoacetate and 19.3 g of potassium carbonate were added thereto, followed by stirring at 100° C. for 1 hour. The reaction liquid was cooled to room temperature, and then water was added, followed by extraction with ethyl acetate. The organic layer was washed with brine, and then dried over anhydrous sodium sulfate. The solvent was evaporated under reduced pressure, and the obtained residue was purified by silica gel column chromatography (hexane:ethyl acetate=80:20) to obtain 34.6 g of ethyl N-(3-chloro-2-methylphenyl)-N-[(4-methylphenyl)sulfonyl]glycine.

Reference Example 3

35.8 g of ethyl N-(3-chloro-2-methylphenyl)-N-[(4-methylphenyl)sulfonyl]glycine was dissolved in 157 mL of ethanol and 157 mL of 1,4-dioxane, and 157 mL of a 1 M aqueous sodium hydroxide solution was added thereto, followed by stirring at 60° C. overnight. The reaction liquid was cooled to room temperature, and then concentrated under reduced pressure. The residue was dissolved in water, acidified by addition of 1 M hydrochloric acid, and then extracted with ethyl acetate. The organic layer was washed with saturated brine, and then dried over anhydrous sodium sulfate. The solvent was evaporated under reduced pressure to obtain 29.3 g of N-(3-chloro-2-methylphenyl)-N-[(4-methylphenyl)sulfonyl]glycine.

Reference Example 4

7.42 g of 4-methoxybenzylamine was dissolved in 70 mL of methylene chloride, and a solution (10 mL) of 23.2 g of bromoacetyl bromide in methylene chloride was added thereto at −10° C. To the reaction liquid was added dropwise a solution (10 mL) of 8.0 mL of triethylamine in methylene chloride at 0° C., followed by stirring at room temperature for 30 minutes. To the reaction liquid was added water under ice-cooling, followed by extraction with methylene chloride. The organic layer was washed with an aqueous saturated sodium hydrogen carbonate solution, and then dried over anhydrous magnesium sulfate. The solvent was evaporated under reduced pressure, and the obtained residue was purified by silica gel column chromatography (hexane:ethyl acetate=90:10 to 0:100) to obtain a product, which was recrystallized from ethyl acetate to obtain 6.11 g of 2-bromo-N-(4-methoxybenzyl)acetamide.

Reference Example 5

3.93 g of 3-chloro-2-methylaniline was dissolved in 10 mL of DMF, and 2.00 g of potassium carbonate was added thereto, followed by portionwise addition of 3.55 g of 2-bromo-N-(4-methoxybenzyl)acetamide over 1 hour. The mixture was stirred at room temperature overnight, and ice water was added thereto, followed by extraction with ethyl acetate. The organic layer was washed with brine, and then dried over anhydrous sodium sulfate. The solvent was evaporated under reduced pressure, and the obtained residue was purified by silica gel column chromatography (hexane:ethyl acetate=70:30 to 30:70) to obtain 2.89 g of $N^2$-(3-chloro-2-methylphenyl)-N-(4-methoxybenzyl)glycinamide.

Reference Example 6

1.00 g of 3-chloro-2-methylaniline was dissolved in 10 mL of hexamethylphosphoramide, and 1.80 g of sodium hydrogen carbonate and 1.19 g of methyl 3-bromopropionate sequentially were added thereto, followed by stirring at room temperature for 4 hours. To the reaction liquid was added water, followed by extraction with diisopropyl ether. The organic layer was washed with saturated brine, and then dried over anhydrous magnesium sulfate. The solvent was evaporated under reduced pressure, and the obtained residue was purified by silica gel column chromatography (hexane:ethyl acetate=95:5 to 85:25) to obtain 0.92 g of methyl N-(3-chloro-2-methylphenyl)-β-alanine.

Reference Example 7

0.92 g of methyl N-(3-chloro-2-methylphenyl)-β-alanine was dissolved in 5 mL of pyridine, and 1.19 g of p-toluene sulfonylchloride was added thereto under ice-cooling, followed by stirring at room temperature overnight. To the reaction liquid was added water, followed by extraction with diisopropyl ether. The organic layer was washed with 1 M hydrochloric acid, brine, and an aqueous saturated sodium hydrogen carbonate solution, and then dried over anhydrous magnesium sulfate. The solvent was evaporated under reduced pressure, and the obtained residue was purified by silica gel column chromatography (hexane:ethyl acetate=90:10 to 70:30) to obtain 0.92 g of methyl N-(3-chloro-2-methylphenyl)-N-[(4-methylphenyl)sulfonyl]-α-alanine.

Reference Example 8

652 mg of 4-{[(3-chloro-2-methylphenyl)amino]sulfonyl}benzoic acid was dissolved in 10.0 mL of THF, and 6.00 mL of a 1 M borane-THF complex was added thereto under an argon atmosphere, followed by stirring at room temperature for 4 hours. To the reaction liquid was added 1.00 mL of a mixed solution of water-acetic acid (1:1) and added water, followed by extraction with ethyl acetate. The organic layer was washed with an aqueous saturated sodium hydrogen carbonate solution and saturated brine, and then dried over anhydrous sodium sulfate. The solvent was evaporated under reduced pressure to obtain 467 mg of N-(3-chloro-2-methylphenyl)-4-(hydroxymethyl)benzenesulfonamide.

Reference Example 9

830 mg of methyl 4-cyanopyridine-2-carboxylate was dissolved in 20.0 mL of ethanol and 20.0 mL of aqueous ammonia, and 160 mg of Raney nickel was added thereto, followed by stirring at room temperature for 4 hours under a hydrogen atmosphere. The reaction liquid was filtered through Celite, the filtrate was concentrated under reduced pressure, and the obtained residue was purified by silica gel column chromatography (chloroform:methanol=10:1) to obtain 410 mg of 4-(aminomethyl)pyridine-2-carboxamide.

Reference Example 10

20.0 g of ethyl (3-cyanophenoxy)acetate was dissolved in 100 mL of ethanol, and 5.58 mL of acetic acid and 4.00 g of 10% Pd—C (Kawaken, AD type, water content 54%) were added thereto, followed by stirring at room temperature overnight under a hydrogen atmosphere. The reaction liquid was filtered through Celite, the filtrate was concentrated under reduced pressure, and the obtained residue was purified by silica gel column chromatography (chloroform:methanol=10:1). The obtained product was dissolved in ethyl acetate, and 10.0 mL of a 4 M hydrogen chloride/ethyl acetate solution was added thereto, followed by stirring at room temperature for 1 hour. The precipitated crystal was collected by filtration, washed with ethyl acetate, and dried under reduced pressure to obtain 6.49 g of [3-(aminomethyl)phenoxy]ethyl acetate hydrochloride.

Reference Example 11

To a mixture of 41 mg of copper iodide, 1.82 g of tripotassium phosphate, 38 mg of N,N'-dimethylethylenediamine, 1.00 g of 1-(4-iodophenyl)methyl amine, and 510 mg of 2-piperidone was added 4.29 mL of toluene, followed by stirring at 80° C. overnight under an argon atmosphere. The reaction liquid was filtered through Celite, the filtrate was then concentrated under reduced pressure, and the obtained residue was purified by silica gel column chromatography (chloroform:methanol=10:1) to obtain 552 mg of 1-[4-(aminomethyl)phenyl]piperidine-2-one.

Reference Example 12

5.00 g of 4-fluoro-3-methylbenzoic acid was dissolved in 100 mL of ethanol, and 2.59 mL of concentrated sulfuric acid was added thereto, followed by heating under reflux overnight. The reaction liquid was cooled to room temperature, and then concentrated under reduced pressure, and the obtained residue was alkalified (pH=8) by addition of an aqueous saturated sodium hydrogen carbonate solution under ice-cooling, followed by extraction with ethyl acetate. The organic layer was washed with brine, and then dried over anhydrous sodium sulfate. The solvent was evaporated under reduced pressure to obtain 5.86 g of ethyl 4-fluoro-3-methylbenzoate.

Reference Example 13

3.00 g of ethyl 4-fluoro-3-methylbenzoate was dissolved in 50.0 mL of carbon tetrachloride, and 4.40 g of N-bromosuccinimide and 1.35 g of 2,2'-azobisisobutyronitrile were added thereto, followed by heating under reflux for 4 hours. The reaction liquid was cooled to room temperature, and then concentrated under reduced pressure, and the obtained residue was purified by silica gel column chromatography (hexane:ethyl acetate=7:3) to obtain 1.73 g of ethyl 3-(bromomethyl)-4-fluorobenzoate.

Reference Example 14

1.56 g of di-tert-butyl iminodicarboxylate was dissolved in 20.0 mL of DMF, and 804 mg of potassium tert-butoxide was added under ice-cooling, followed by stirring at room temperature for 1 hour. To the reaction liquid was added dropwise a solution (10.0 mL) of 1.70 g of ethyl 3-(bromomethyl)-4-fluorobenzoate in DMF, followed by stirring at room temperature overnight. The reaction liquid was poured to water, followed by extraction with ethyl acetate, and the organic layer was washed with brine, and then dried over anhydrous sodium sulfate. The solvent was evaporated under reduced pressure to obtain 2.59 g of 3-{[bis(tert-butoxycarbonyl)amino]methyl}-4-fluorobenzoic acid.

Reference Example 15

2.59 g of 3-{[bis(tert-butoxycarbonyl)amino]methyl}-4-fluorobenzoic acid was dissolved in 10.0 mL of ethyl acetate, and 10.0 mL of a 4 M hydrogen chloride/ethyl acetate solution was added thereto, followed by stirring at room temperature for 4 hours. The reaction liquid was concentrated under reduced pressure, and the obtained residue was crystallized by addition of ethyl acetate and hexane to obtain 2.59 g of ethyl 3-(aminomethyl)-4-fluorobenzoate hydrochloride.

Reference Example 16

374 mg of 60% sodium hydride was suspended in 20.0 mL of dimethoxyethane, and 1.91 g of ethyl diethylphosphonoacetate was added dropwise thereto at −5° C., followed by stirring at room temperature for 10 minutes. To the reaction liquid was added dropwise a solution of tert-butyl (3-formylbenzyl)carbamate in dimethoxyethane (5.00 mL), followed by stirring at 60° C. for 4 hours. The reaction liquid was cooled to room temperature, followed by addition of water and extraction with ethyl acetate. The organic layer was washed with brine, and then dried over anhydrous sodium sulfate. The solvent was evaporated under reduced pressure to obtain ethyl 3-{[(tert-butoxycarbonyl)amino]methyl}cinnamate. This was dissolved in 5.00 mL of ethyl acetate, and 8.50 mL of a 4 M hydrogen chloride/ethyl acetate solution was added thereto, followed by stirring at room temperature for 6 hours. The resulting precipitate was collected by filtration, washed with ethyl acetate, and then dried under reduced pressure to obtain 1.71 g of ethyl 3-(aminomethyl)cinnamate hydrochloride.

Reference Example 17

779 mg of ethyl 3-(aminomethyl)cinnamte was dissolved in 5.00 mL of ethanol, and 80 mg of 10% Pd—C (Kawaken, AD type) was added thereto, followed by stirring at room temperature for 3 hours under a hydrogen atmosphere. The reaction liquidn was filtered through Celite, and the filtrate was concentrated under reduced pressure to obtain 773 mg of ethyl 3-[3-(aminomethyl)phenyl]propionate.

Reference Example 18

670 mg of methyl 5-formyl-1-methyl-1H-pyrrole-2-carboxylate was dissolved in 10.0 mL of THF, and 303 mg of sodium borohydride was added thereto at −20° C., followed by stirring at −20° C. for 30 minutes, and then at 0° C. for further 1 hour. To the reaction liquid was added an aqueous saturated ammonium chloride solution, followed by extraction with ethyl acetate. The organic layer was washed with an aqueous saturated sodium hydrogen carbonate solution and brine, and then dried over anhydrous sodium sulfate. The solvent was evaporated under reduced pressure to obtain 592 mg of methyl 5-(hydroxymethyl)-1-methyl-1H-pyrrole-2-carboxylate.

Reference Example 19

590 mg of methyl 5-(hydroxymethyl)-1-methyl-1H-pyrrole-2-carboxylate, 770 mg of phthalimide, and 1.83 g of triphenylphosphine were dissolved in 10.0 mL of THF, and 2.75 mL of diethyl azodicarboxylate was added thereto under ice-cooling, followed by stirring at room temperature overnight. The reaction liquid was concentrated under reduced pressure, and the obtained residue was purified by silica gel column chromatography (hexane:ethyl acetate=3:1 to 1:1) to obtain 650 mg of methyl 5-[(1,3-dioxo-1,3-dihydro-2H-isoindol-2-yl)methyl]-1-methyl-1H-pyrrole-2-carboxylate.

Reference Example 20

650 mg of methyl 5-[(1,3-dioxo-1,3-dihydro-2H-isoindole-2-yl)methyl]-1-methyl-1H-pyrrole-2-carboxylate was dissolved in 20.0 mL of methanol, and 109 mg of hydrazine monohydrate was added thereto, followed by stirring at room temperature overnight. The reaction liquid was concentrated under reduced pressure, to the obtained residue was added chloroform, and the insolubles were filtered off. Then, the filtrate was concentrated under reduced pressure to obtain 294 mg of methyl 5-(aminomethyl)-1-methyl-1H-pyrrole-2-carboxylate.

Reference Example 21

4.86 g of methyl 5-(hydroxymethyl)thiophene-3-carboxylate was dissolved in 50.0 mL of dichloromethane, and 4.12 mL of thionyl chloride was added thereto under ice-cooling, followed by stirring at room temperature for 15 hours. The reaction liquid was concentrated under reduced pressure, and to the obtained residue was added ethyl acetate, and then washed with an aqueous saturated sodium hydrogen carbonate solution and saturated brine. It was dried over anhydrous magnesium sulfate, and then the solvent was evaporated to obtain 4.90 g of methyl 5-(chloromethyl)thiophene-3-carboxylate.

Reference Example 22

3.57 g of 3-cyanophenol was dissolved in 60.0 mL of acetonitrile, and 5.81 mL of ethyl 2-bromo-2-methylpropionate and 14.6 g of cesium carbonate were added thereto, followed by heating under reflux overnight. The reaction liquid was cooled to room temperature, followed by addition of water and extraction with ethyl acetate. The organic layer was washed with saturated brine. It was dried over anhydrous magnesium sulfate, the solvent was then evaporated, and the residue was purified by silica gel column chromatography (hexane:ethyl acetate=9:1) to obtain 6.75 g of ethyl 2-(3-cyanophenoxy)-2-methyl propionate.

Reference Example 96

2.50 g of 3-hydroxybenzaldehyde, 2.77 g of methyl L-(–)-lactate, and 6.44 g of triphenylphosphine were dissolved in 25.0 mL of THF, and 22.2 mL of a 2.2 M diethyl azodicarboxylate/toluene solution was added thereto under ice-cooling, followed by stirring at room temperature overnight. To the reaction liquid was added an aqueous saturated sodium hydrogen carbonate solution, followed by extraction with ethyl acetate. The organic layer was washed with saturated brine, and then dried over anhydrous magnesium sulfate. The solvent was evaporated under reduced pressure, and the obtained residue was purified by silica gel column chromatography (hexane:ethyl acetate=7:3 to 1:1) to obtain 1.67 g of methyl (2R)-2-(3-formylphenoxy)propionate. The obtained methyl (2R)-2-(3-formylphenoxy)propionate was dissolved in 33.3 mL of methanol, and 394 mg of sodium borohydride was added thereto under ice-cooling, followed by stirring for 30 minutes. To the reaction liquid were added ethyl acetate and water, followed by extraction with ethyl acetate. The organic layer was washed with saturated brine, and then dried over anhydrous magnesium sulfate. The solvent was evaporated under reduced pressure to obtain 1.68 g of methyl (2R)-2-[3-(hydroxymethyl)phenoxy]propionate.

Reference Example 97

300 mg of methyl (2R)-2-[3-(hydroxymethyl)phenoxy]propionate, 465 mg of di-tert-butyl iminodicarboxylate, and 543 mg of triphenylphosphine were dissolved in 3.00 mL of toluene, and 445 mg of diisopropyl azodicarboxylate was added thereto under ice-cooling, followed by stirring at room temperature overnight. The reaction liquid was concentrated under reduced pressure, and the obtained residue was purified by silica gel column chromatography (hexane:ethyl acetate=95:5 to 0:100) to obtain 584 mg of methyl (2R)-2-(3-{[bis(tert-butoxycarbonyl)amino]methyl}phenoxy)propionate.

Reference Example Compounds 1 to 104 shown in Tables 3 to 10 later were prepared in the same manner as the methods of Reference Examples 1 to 22, 96, and 97, using each corresponding starting material. In addition, the structures, the synthetic methods, and the physiochemical data of Reference Example compounds are shown in Tables 3 to 10.

Preparative Example 1

707 mg of N-(3-chloro-2-methylphenyl)-N-[(4-methylphenyl)sulfonyl]glycine was dissolved in 8.00 mL of DMF, and 302 mg of 4-methoxybenzylamine, 324 mg of HOBt, and 460 mg of WSC were added thereto, followed by stirring at room temperature overnight. To the reaction liquid was added water, followed by extraction with ethyl acetate, and the organic layer was washed with saturated brine, and then dried over anhydrous sodium sulfate. The solvent was evaporated under reduced pressure, and the obtained residue was purified by silica gel column chromatography (hexane:ethyl acetate=4:1) to obtain 881 mg of $N^2$-(3-chloro-2-methylphenyl)-N-(4-methoxybenzyl)-$N^2$-[(4-methylphenyl)sulfonyl]glycinamide.

Preparative Example 2

449 mg of N-(3-chloro-2-methylphenyl)-4-fluorobenzenesulfonamide was dissolved in 3.00 mL of DMF, and 387 mg of 2-bromo-N-(4-methoxybenzyl)acetamide and 207 mg of potassium carbonate were added thereto, followed by stirring at room temperature overnight. To the reaction liquid was added an aqueous sodium hydrogen carbonate solution, followed by extraction with chloroform, and the organic layer was washed with brine, and then dried over anhydrous sodium sulfate. The solvent was evaporated under reduced pressure, and the obtained residue was purified by silica gel column chromatography (hexane:ethyl acetate) to obtain a product, which was crystallized from hexane/ethyl acetate to obtain 466 mg of $N^2$-(3-chloro-2-methylphenyl)-N-(4-methoxybenzyl)-$N^2$-[(4-fluorophenyl)sulfonyl]glycinamide.

Preparative Example 3

200 mg of $N^2$-(3-chloro-2-methylphenyl)-N-(4-methoxybenzyl)glycinamide was dissolved in 2.0 mL of pyridine, and a solution (2.0 mL) of 200 mg of 4-hydroxybenzenesulfonamide in dichloroethane was added thereto, followed by stirring at 80° C. overnight. The reaction liquid was concentrated under reduced pressure, to the residue was added water, followed by extraction with ethyl acetate, and the organic layer was washed with 1 M hydrochloric acid and water, and then dried over anhydrous sodium sulfate. The solvent was evaporated under reduced pressure, and the obtained residue was purified by silica gel column chromatography (hexane:ethyl acetate=70:30 to 30:70), and further purified by silica gel column chromatography (chloroform:methanol=100:0 to 97:3), and the obtained residue was crystallized from diisopropyl ether to obtain 68 mg of $N^2$-(3-chloro-2-methylphenyl)-$N^2$-[(4-hydroxyphenyl)sulfonyl]-N-(4-methoxybenzyl)glycinamide.

Preparative Example 4

668 mg of N-[4-(benzyloxy)benzyl]-$N^2$-(3-chloro-2-methylphenyl)-$N^2$-[(4-methylphenyl)sulfonyl]glycinamide was dissolved in 5.00 mL of methanol and 2.00 mL of THF, and 70 mg of 10% Pd—C (Kawaken, AD type, water content 54%) was added thereto, followed by stirring at room temperature for 6.5 hours under a hydrogen atmosphere. The reaction liquid was filtered through Celite, the filtrate was evaporated under reduced pressure, and the obtained residue was purified by silica gel column chromatography (hexane:ethyl acetate=50:50 to 30:70) to obtain a product, which was recrystallized from ethanol/water to obtain 373 mg of $N^2$-(3-chloro-2-methylphenyl)-N-(4-hydroxybenzyl)-$N^2$-[(4-methylphenyl)sulfonyl] glycinamide.

Preparative Example 5

300 mg of 4-[((3-chloro-2-methylphenyl){2-[(4-methoxybenzyl)amino]-2-oxoethyl}amino)sulfonyl]benzoic acid was dissolved in 5.00 mL of THF, and 340 mg of ethyl chloroformate and 326 mg of triethylamine were added thereto, followed by stirring at room temperature for 1 hour. To the reaction liquid was added dropwise an aqueous solution (0.80 mL) of 360 mg of sodium borohydride over 30 minutes, followed by stirring at room temperature for 2 hours. The reaction liquid was acidified with addition of 8.0 mL of 1 M hydrochloric acid, and then extracted with a mixed solvent of chloroform/methanol (5/1), and the organic layer was dried over anhydrous sodium sulfate. The solvent was evaporated under reduced pressure, and the obtained residue was purified by silica gel column chromatography (chloroform:methanol=100:0 to 90:10) to obtain a product, which was crystallized from diisopropyl ether to obtain 118 mg of $N^2$-(3-chloro-2-methylphenyl)-$N^2$-{[4-(hydroxymethyl)phenyl]sulfonyl}-N-(4-methoxybenzyl)glycinamide.

Preparative Example 6

330 mg of $N^2$-(3-chloro-2-methylphenyl)-$N^2$-[(4-methylphenyl)sulfonyl]-N-(pyridine-4-ylmethyl)glycinamide was dissolved in 5.0 mL of methylene chloride, and 166 mg of m-chloroperbenzoic acid was added thereto, followed by stirring at room temperature for 4 hours. To the reaction liquid was added an aqueous saturated sodium hydrogen carbonate solution, and then extracted with chloroform. The organic layer was concentrated under reduced pressure, the obtained residue was purified by silica gel column chromatography (chloroform:methanol=99:1), and the obtained residue was crystallized from hexane/ethyl acetate to obtain 179 mg of $N^2$-(3-chloro-2-methylphenyl)-$N^2$-[(4-methylphenyl)sulfonyl]-N-[(1-oxidopyridine-4-yl)methyl]glycinamide.

Preparative Example 25

220 mg of methyl 4-{[(3-chloro-2-methylphenyl)amino]sulfonyl}benzoate was dissolved in 1.10 mL of DMF, and 168 mg of 2-bromo-N-(4-methoxybenzyl)acetamide and 100 mg of potassium carbonate were added thereto, followed by stirring at room temperature for 7 hours. To the reaction liquid was added water, followed by extraction with ethyl acetate, and the organic layer was washed with brine, and then dried over anhydrous sodium sulfate. The solvent was evaporated under reduced pressure, and the obtained residue was purified by silica gel column chromatography (hexane:ethyl acetate=7:3 to 4:6) to obtain 270 mg of methyl 4-[((3-chloro-2-methylphenyl)-{2-[(4-methoxybenzyl)amino]-2-oxoethyl}amino)sulfonyl]benzoate. The obtained methyl 4-[((3-chloro-2-methylphenyl)-{2-[(4-methoxybenzyl)amino]-2-oxoethyl}amino)sulfonyl]benzoate was dissolved in 2.00 mL of methanol and 1.50 mL of THF, and 1.05 mL of a 1 M aqueous sodium hydroxide solution was added thereto, followed by stirring at room temperature for 2 days. The reaction liquid was acidified by addition of 1 M hydrochloric acid, and then extracted with a mixed solvent of chloroform/methanol (5/1), and the organic layer was dried over anhydrous magnesium sulfate. The solvent was evaporated under reduced pressure, and the obtained residue was purified by silica gel chromatography (chloroform:methanol=100:0 to 90:10) to obtain 204 mg of 4-[((3-chloro-2-methylphenyl){2-[(4-methoxybenzyl)amino]-2-oxoethyl}amino)sulfonyl]benzoic acid.

Preparative Example 33

100 mg of $N^2$-(3-chloro-2-methylphenyl)-N-[3-(hydroxymethyl)benzyl]-$N^2$-[(4-methylphenyl)sulfonyl]glycinamide was obtained from 240 mg of 3-[({N-(3-chloro-2-methylphenyl)-N-[(4-methylphenyl)sulfonyl]glycyl}amino)methyl]benzoic acid in the same manner as in Preparative Example 5.

Example 1

308 mg of methyl 4-[({N-(3-chloro-2-methylphenyl)-N-[(4-methylphenyl)sulfonyl]glycyl}amino)methyl]benzoate was dissolved in 5.00 mL of methanol and 2.00 mL of THF, and 2.40 mL of a 1 M aqueous sodium hydroxide solution was added thereto, followed by stirring at room temperature overnight. Then, to the reaction liquid was added 3.00 mL of THF, followed by stirring at 60° C. for 4 hours. The reaction liquid was ice-cooled, acidified by addition of 2.60 mL of 1 M hydrochloric acid, and then extracted with a mixed solvent of chloroform/methanol (5/1), and the organic layer was dried over anhydrous sodium sulfate. The solvent was evaporated under reduced pressure, and the obtained residue was purified by silica gel column chromatography (chloroform:methanol=100:0 to 90:10) to obtain 601 mg of 4-[({N-(3-chloro-2-methylphenyl)-N-[(4-methylphenyl)sulfonyl]glycyl}amino)methyl]benzoic acid.

Example 2

185 mg of 4-[({N-(3-chloro-2-methylphenyl)-N-[(4-methylphenyl)sulfonyl]glycyl}amino)methyl]benzoic acid, 25 mg of ammonium chloride, and 62 mg of HOBt were dissolved in 2.00 mL of DMF, and 78 mg of WSC was added thereto, followed by stirring at room temperature overnight. To the reaction liquid was added water, followed by extraction with ethyl acetate, and the organic layer was washed with water, an aqueous sodium hydrogen carbonate solution, and water, and then dried over anhydrous sodium sulfate. The solvent was evaporated under reduced pressure, and the obtained residue was purified by silica gel column chromatography (hexane:ethyl acetate=20:80 to 0:100) to obtain a product, which was recrystallized from ethanol/water (95:5) to obtain 89 mg of 4-[({N-(3-chloro-2-methylphenyl)-N-[(4-methylphenyl)sulfonyl]glycyl}amino)methyl]benzoic acid amide.

Example 3

300 mg of $N^2$-(3-chloro-2-methylphenyl)-N-(4-hydroxybenzyl)-$N^2$-[(4-methylphenyl)sulfonyl]glycinamide was dissolved in 2.00 mL of DMF, and 110 mg of potassium carbonate and 133 mg of ethyl bromoacetate were added thereto, followed by stirring at room temperature overnight. To the reaction liquid was added water, followed by extraction with ethyl acetate, and the organic layer was washed with saturated brine, and then dried over anhydrous sodium sulfate. The solvent was evaporated under reduced pressure, and the obtained residue was purified by silica gel column chromatography (hexane:ethyl acetate=60:40 to 30:70) to obtain 370 mg of ethyl 4-[({N-(3-chloro-2-methylphenyl)-N-[(4-methylphenyl)sulfonyl]glycyl}amino)methyl]phenoxyacetate.

Example 4

182 mg of 3-[({N-(3-chloro-2-methylphenyl)-N-[(4-methylphenyl)sulfonyl]glycyl}amino)methyl]benzoic acid was dissolved in 0.50 mL of DMF, and 75 mg of 1,1'-carbonyldiimidazole was added thereto, followed by stirring at room temperature for 1 hour. To the reaction liquid were added 40 mg of methane sulfonamide and 66 mg of DBU, followed by stirring at 50° C. for 8 hours. The reaction liquid was acidified by addition of 2.50 mL of 1 M hydrochloric acid, and then extracted with a mixed solvent of chloroform/methanol (5/1), and the organic layer was dried over anhydrous sodium sulfate. The solvent was evaporated under reduced pressure, and the obtained residue was purified by silica gel column chromatography (chloroform:methanol=100:0 to 95:5) to obtain 207 mg of 3-[({N-(3-chloro-2-methylphenyl)-N-[(4-methylphenyl)sulfonyl]glycyl}amino)methyl]-N-(methylsulfonyl)benzamide.

Example 230

404 mg of $N^2$-(3-chloro-2-methylphenyl)-N-(3-cyanobenzyl)-N-[(4-methylphenyl)sulfonyl]glycinamide was dissolved in 8.08 mL of ethanol, and 120 mg of hydroxylamine hydrochloride and 0.241 mL of triethylamine were added thereto, followed by heating under reflux for 6 hours. The reaction liquid was cooled to room temperature, and then extracted with ethyl acetate, and the organic layer was washed with water and saturated brine, and then concentrated under reduced pressure. The obtained residue was dissolved in 5.00 mL of DMF, and 88 mg of pyridine and 167 mg of 2-ethylhexyl chloroformate were added thereto under ice-cooling, followed by stirring at 5° C. for 1 hour. The reaction liquid was diluted with water, and then extracted with ethyl acetate, and the organic layer was washed with water and saturated brine, and then dried over anhydrous magnesium sulfate. The solvent was evaporated under reduced pressure, and the obtained residue was dissolved in 8.54 mL of xylene, followed by heating under reflux for 13 hours. The reaction liquid was concentrated under reduced pressure, and to the obtained residue were added chloroform and hexane, and the resulting precipitate was collected by filtration. The obtained product was recrystallized from ethanol/diisopropyl ether to obtain 298 mg of $N^2$-(3-chloro-2-methylphenyl)-$N^2$-[(4-methylphenyl)sulfonyl]-N-[3-(5-oxo-4,5-dihydro-1,2,4-oxadiazole-3-yl)benzyl] glycinamide.

Example 231

300 mg of $N^2$-(3-chloro-2-methylphenyl)-N-(3-cyanobenzyl)-$N^2$-[(4-methylphenyl)sulfonyl]glycinamide was dissolved in 5.00 mL of DMF, and 125 mg of sodium azide and 103 mg of ammonium chloride were added thereto, followed by stirring at 100° C. for 6 hours. The reaction liquid was concentrated under reduced pressure, and to the obtained residue was added water, followed by extraction with chloroform. The organic layer was washed with saturated brine, and then dried over anhydrous magnesium sulfate. The solvent was evaporated under reduced pressure, and the obtained residue was purified by preparative thin layer chromatography (chloroform:methanol=80:20). The obtained product was recrystallized from ethanol/diisopropyl ether to obtain 82.6 mg of $N^2$-(3-chloro-2-methylphenyl)-$N^2$-[(4-methylphenyl)sulfonyl]-N-[3-(2H-tetrazol-5-yl)benzyl]glycinamide.

Preparative Example Compounds 1 to 122 shown in Tables 11 to 22, and Example compounds 1 to 231 shown in Tables 23 to 45 were prepared in the same manner as the methods of Preparative Examples 1 to 6, 25, and 33, and Examples 1 to 4, 230, and 231, using each corresponding starting material. In addition, the production processes and the physiochemical data of Preparative Example compounds are shown in Tables 46 to 48, and the production processes and the physiochemical data of Example compounds are shown in Tables 49 to 56.

TABLE 3

| Rf | Syn | Str | Dat |
|---|---|---|---|
| 1 | R1 | 3-chloro-2-methylphenyl sulfonamide with 4-methylphenyl group (structure) | FP: 296 |
| 2 | R2 | N-(3-chloro-2-methylphenyl)-N-(CH2CO2Et)-(4-methylphenyl)sulfonyl (structure) | FP: 382 |
| 3 | R3 | N-(3-chloro-2-methylphenyl)-N-(CH2CO2H)-(4-methylphenyl)sulfonyl (structure) | FP: 354 |
| 4 | R4 | BrCH2C(O)NH-CH2-C6H4-OMe (structure) | FP: 258, 260 |
| 5 | R5 | (3-chloro-2-methylphenyl)NH-CH2-C(O)-NH-CH2-C6H4-OMe (structure) | EP: 319 |

TABLE 3-continued

| Rf | Syn | Str | Dat |
|---|---|---|---|
| 6 | R6 | (Cl, Me-substituted phenyl with NH-CH2CH2-CO2Me) | EP: 228 |
| 7 | R7 | (Cl, Me-substituted phenyl with N(Ts)-CH2CH2-CO2Me) | EP: 403 [M+Na]+ |
| 8 | R8 | (Cl, Me-substituted phenyl-NH-SO2-C6H4-CH2OH) | EI: 311 |
| 9 | R9 | (H2N-CH2-pyridine-CONH2) | EP: 152 |
| 10 | R10 | HCl, H2N-CH2-C6H4-O-CH2-CO2Et | FP: 210 |
| 11 | R11 | (2-oxopiperidinyl-phenyl-CH2NH2) | EI: 204 |
| 12 | R12 | (F, Me-substituted phenyl-CO2Et) | EI: 182 |
| 13 | R13 | (F-phenyl-CH2Br, CO2Et) | EI: 260 |
| 14 | R14 | (F-phenyl-CH2-NBoc2, CO2Et) | FP: 398 |

TABLE 4

| Rf | Syn | Str | Dat |
|---|---|---|---|
| 15 | R15 | HCl, H2N-CH2-C6H3(F)-CO2Et | FP: 198 |
| 16 | R16 | HCl, H2N-CH2-C6H4-CH=CH-CO3Et | FP: 206 |
| 17 | R17 | HCl, H2N-CH2-C6H4-CH2CH2-CO2Et | EI: 207 |
| 18 | R18 | HO-CH2-(N-Me-pyrrole)-CO2Me | EI: 169 |
| 19 | R19 | (phthalimido-CH2-(N-Me-pyrrole)-CO2Me) | FP: 298 [M]+ |
| 20 | R20 | H2N-CH2-(N-Me-pyrrole)-CO2Me | EI: 168 |
| 21 | R21 | Cl-CH2-thiophene-CO2Me | EI: 190 |
| 22 | R22 | NC-C6H4-O-C(Me)2-CO2Et | EI: 233 |
| 23 | R1 | (Cl, Me-phenyl-NH-SO2-(5-Me-pyridin-2-yl)) | FP: 297 |
| 24 | R1 | (Cl, Me-phenyl-NH-SO2-(4-Me-thiazol-2-yl)) | FP: 303 |

TABLE 4-continued

| Rf | Syn | Str | Dat |
|----|-----|-----|-----|
| 25 | R1 | 3-chloro-2-methylbenzyl-NH-SO2-(4-methylphenyl) | EN: 308 |
| 26 | R1 | 2-methylbenzyl-NH-SO2-(4-methylphenyl) | EN: 274 |
| 27 | R1 | 3-chloro-2-methylphenyl-NH-SO2-(4-MeO2C-phenyl) | EN: 338 |
| 28 | R1 | 3-chloro-2-methylphenyl-NH-SO2-(3-MeO2C-phenyl) | EN: 338 |

TABLE 5

| Rf | Syn | Str | Dat |
|----|-----|-----|-----|
| 29 | R1 | 3-chloro-2-methylphenyl-NH-SO2-(4-cyanophenyl) | EN: 305 |
| 30 | R1 | 3-chloro-2-methylphenyl-NH-SO2-(4-CF3-phenyl) | FP: 350 |
| 31 | R1 | 3-chloro-2-methylphenyl-NH-SO2-(4-Ac-phenyl) | EN: 322 |
| 32 | R1 | 3-chloro-2-methylphenyl-NH-SO2-(3-methyl-2-oxo-benzoxazol-6-yl) | EP: 353 |
| 33 | R2*R3 | 3-chloro-2-methylphenyl-N(CH2CO2H)-SO2-(4-methylthiazol-2-yl) | EP: 361 [M]+ |
| 34 | R2*R3 | 3-chloro-2-methylphenyl-N(CH(Me)CO2H)-SO2-(4-methylphenyl) | EN: 365 |

TABLE 5-continued

| Rf | Syn | Str | Dat |
|---|---|---|---|
| 35 | R2 * R3 | | EN: 380 |
| 36 | R1 * R2 * R3 | | EN: 355 |
| 37 | R3 | | EP: 395 [M + Na]+ |
| 38 | R4 | | FP: 286 |

TABLE 6

| Rf | Syn | Str | Dat |
|---|---|---|---|
| 39 | R3 | | EN: 366 |
| 40 | R6 | | EP: 256 |

TABLE 6-continued

| Rf | Syn | Str | Dat |
|---|---|---|---|
| 41 | R7 * R3 | | EN: 380 |
| 42 | R1 | | FN: 324 |
| 43 | R1 | | FP: 314 |
| 44 | R2 | | FP: 400 |
| 45 | R3 | | FP: 372 |
| 46 | R14 | | EP: 367 |

TABLE 6-continued
| Rf | Syn | Str | Dat |
|---|---|---|---|
| 47 | R15 | 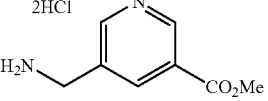 | EP: 167 |
| 48 | R11 | 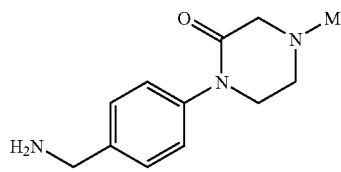 | EI: 219 |
| 49 | R9 | 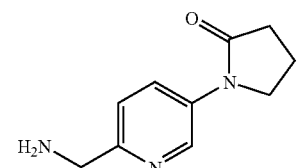 | EI: 191 |
| 50 | R13 | 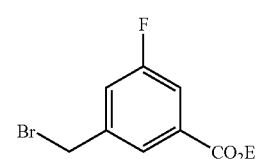 | EI: 260 |
TABLE 7
| Rf | Syn | Str | Dat |
|---|---|---|---|
| 51 | R14 | 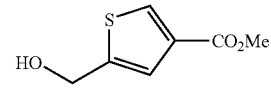 | FP: 398 |
| 52 | R15 | 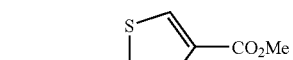 | FP: 198 |
| 53 | R13 | 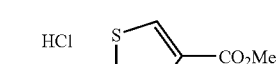 | EI: 260 |
| 54 | R14 | 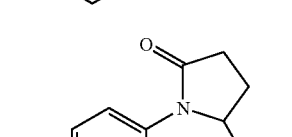 | FP: 398 |
| 55 | R15 | 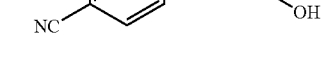 | FP: 198 |
TABLE 7-continued
| Rf | Syn | Str | Dat |
|---|---|---|---|
| 56 | R18 | 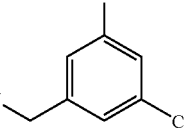 | EI: 172 |
| 57 | R14 | 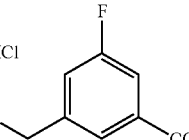 | FP: 372 |
| 58 | R15 | 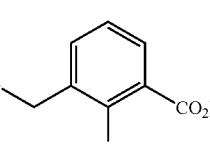 | FP: 172 |
| 59 | R11 | 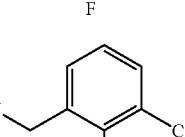 | EI: 216 |
| 60 | R9 | 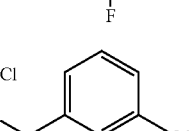 | EI: 221 [M + H]$^+$ |
| 61 | R11 | 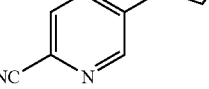 | EI: 203 |
| 62 | R9 | 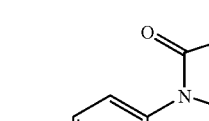 | FP: 208 |
| 63 | R1 | 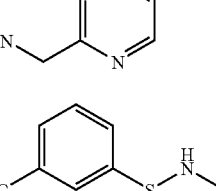 | EN: 225 |
| 64 | R9 | 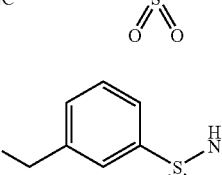 | FP: 231 |
| 65 | R1 | 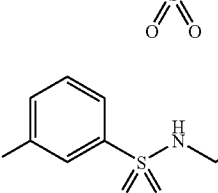 | EI: 254 [M + H]$^+$ |

TABLE 7-continued

| Rf | Syn | Str | Dat |
|---|---|---|---|
| 66 | R9 | (3-(aminomethyl)phenyl)-N-(2-(dimethylamino)ethyl)sulfonamide | FP: 258 |
| 67 | R14 | methyl 2-((bis-Boc-amino)methyl)oxazole-4-carboxylate | FP: 357 |
| 68 | R15 | methyl 2-(aminomethyl)oxazole-4-carboxylate·HCl | FP: 157 |

TABLE 8

| Rf | Syn | Str | Dat |
|---|---|---|---|
| 69 | R12 | ethyl 4-methylthiophene-2-carboxylate | EI: 170 |
| 70 | R13 | ethyl 4-(bromomethyl)thiophene-2-carboxylate | EI: 248 |
| 71 | R14 | ethyl 4-((bis-Boc-amino)methyl)thiophene-2-carboxylate | FP: 386 |
| 72 | R15 | ethyl 4-(aminomethyl)thiophene-2-carboxylate·HCl | FP: 186 |
| 73 | R16 | ethyl (E)-3-(3-(BocNH-methyl)phenyl)-2-methylacrylate | FN: 318 |
| 74 | R16 | ethyl (E)-3-(3-(aminomethyl)phenyl)-2-methylacrylate·HCl | FP: 220 |
| 75 | R17 | ethyl 3-(3-(BocNH-methyl)phenyl)-2-methylpropanoate | FP: 322 |
| 76 | R16 | ethyl 3-(3-(aminomethyl)phenyl)-2-methylpropanoate·HCl | FP: 222 |
| 77 | R13 | methyl 6-(bromomethyl)pyrazine-2-carboxylate | EP: 231 |

TABLE 8-continued

| Rf | Syn | Str | Dat |
|---|---|---|---|
| 78 | R14 | methyl 6-((bis-Boc-amino)methyl)pyrazine-2-carboxylate | FP: 368 |
| 79 | R15 | methyl 6-(aminomethyl)pyrazine-2-carboxylate·HCl | FP: 168 |
| 80 | R11 | 1-(4-(aminomethyl)phenyl)-4-hydroxypyrrolidin-2-one | FP: 207 |
| 81 | R10 | ethyl 2-(3-(aminomethyl)phenoxy)-2-methylpropanoate | EI: 237 |
| 82 | R1 | N-(3-chloro-2-methylphenyl)-4-ethylbenzenesulfonamide | FP: 310 |
| 83 | R1 | N-(3-bromo-2-methylphenyl)-4-methylbenzenesulfonamide | EN: 338 |
| 84 | R1 | N-(3-chloro-2-methylphenyl)-2-methylbenzenesulfonamide | FP: 296 |

TABLE 9
| Rf | Syn | Str | Dat |
|---|---|---|---|
| 85 | R1 | 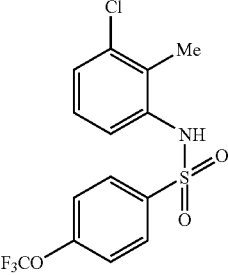 | FP: 366 |
| 86 | R1 | 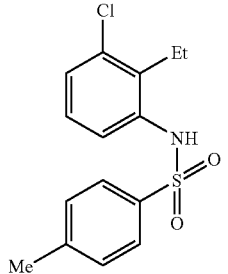 | FP: 310 |
| 87 | R2 | 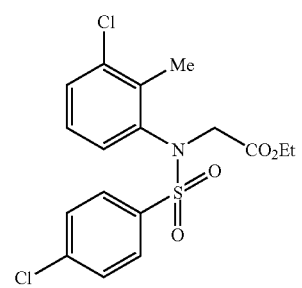 | FP: 402 |
| 88 | R2 | 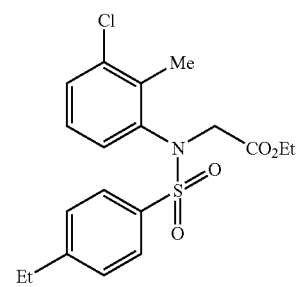 | FP: 396 |
| 89 | R3 | 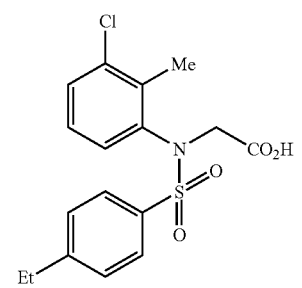 | EN: 366 |
| 90 | R2 | 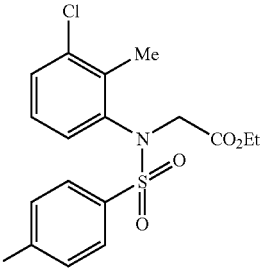 | FP: 393 |
| 91 | R3 | 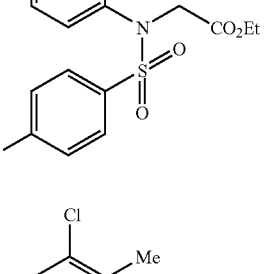 | EN: 363 |
| 92 | R2 | 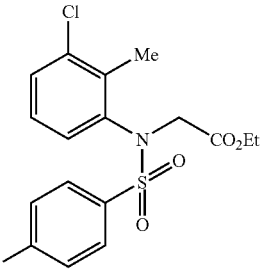 | FP: 436 |
| 93 | R3 | 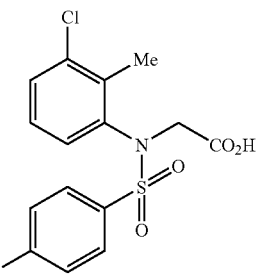 | EN: 406 |
| 94 | R2 | 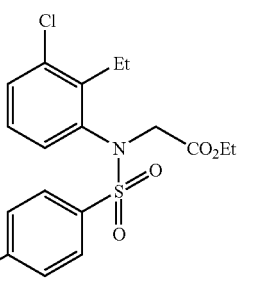 | FP: 396 |

TABLE 10

| Rf | Syn | Str | Dat |
|----|-----|-----|-----|
| 95 | R3 | (structure) | FP: 368 |
| 96 | R96 | (structure) | EP: 233 [M + Na]⁺ |
| 97 | R97 | (structure) | EP: 432 [M + Na]⁺ |
| 98 | R15 | (structure) | EP: 210 |
| 99 | R1 | (structure) | EN: 312 |
| 100 | R2 * R3 | (structure) | EN: 370 |
| 101 | R2 * R3 | (structure) | EN: 396 |
| 102 | R2 * R3 | (structure) | EN: 372 |
| 103 | R1 | (structure) | EI: 311 |
| 104 | R2 * R3 | (structure) | EN: 368 |

TABLE 11

| Pre | Str |
|-----|-----|
| 1 | (structure) |
| 2 | (structure) |

TABLE 11-continued
| Pre | Str |
|---|---|
| 3 | 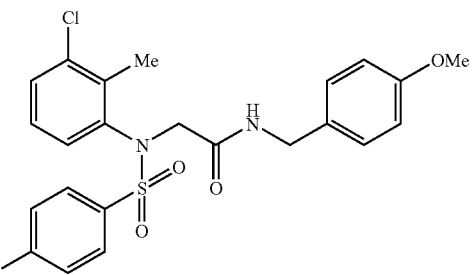 |
| 4 | 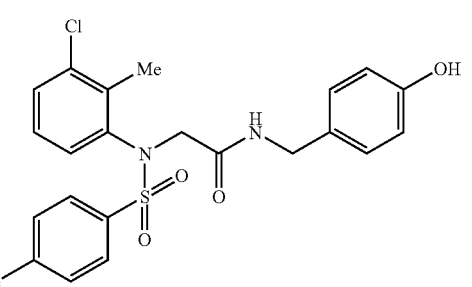 |
| 5 | 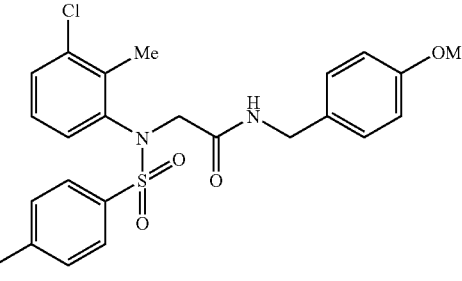 |
| 6 | 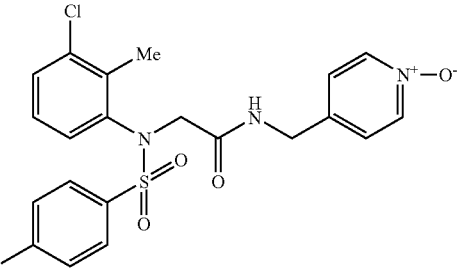 |
| 7 | 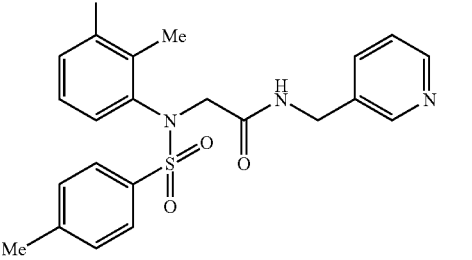 |
| 8 | 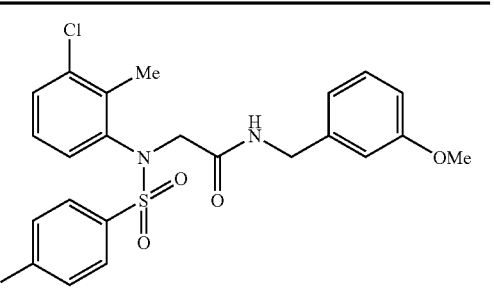 |
| 9 | 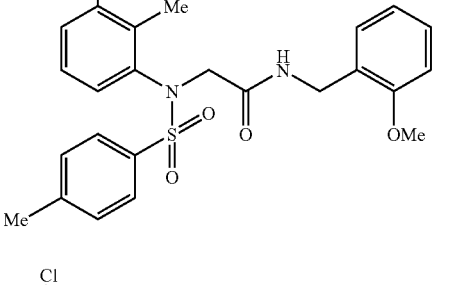 |
| 10 | 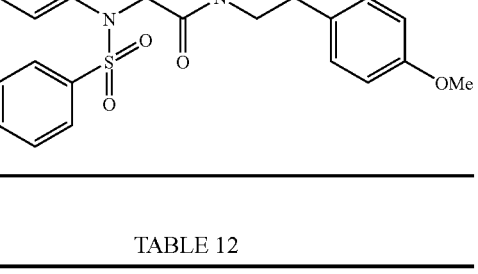 |
TABLE 12
| Pre | Str |
|---|---|
| 11 | 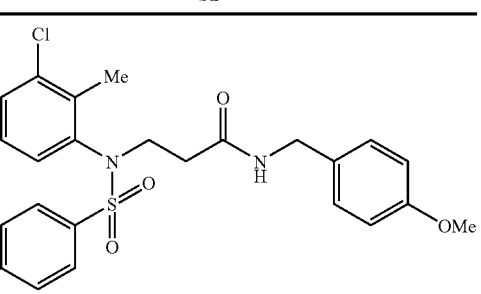 |
| 12 | 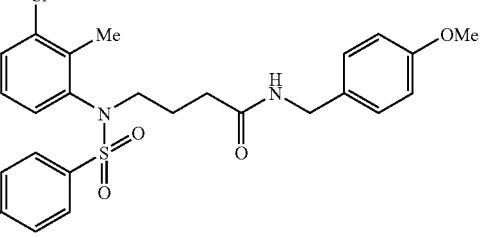 |

TABLE 12-continued
| Pre | Str |
|---|---|
| 13 | 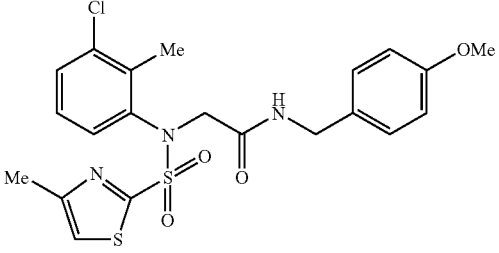 |
| 14 | 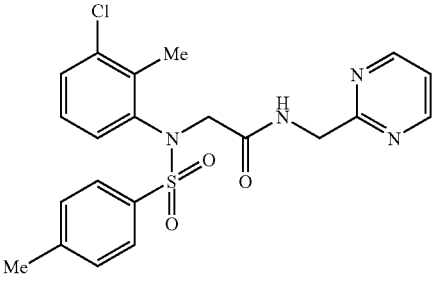 |
| 15 | 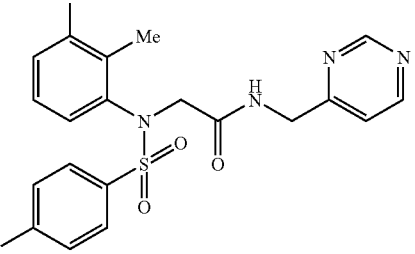 |
| 16 | 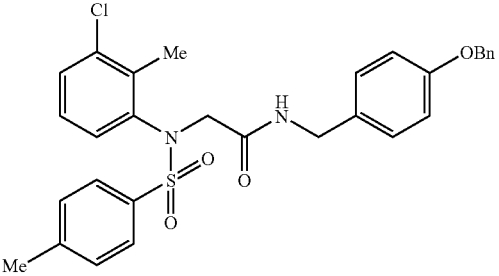 |
| 17 | 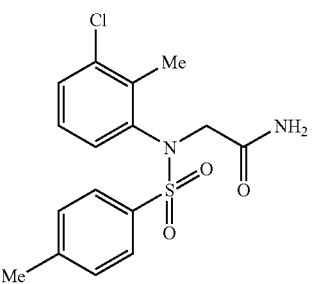 |
| 18 | 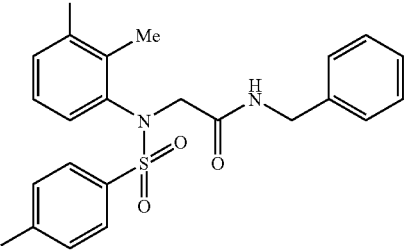 |
| 19 | 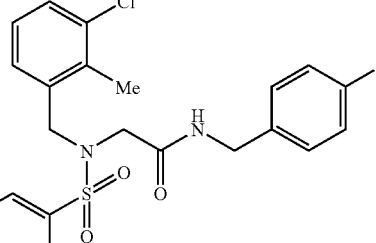 |
| 20 | 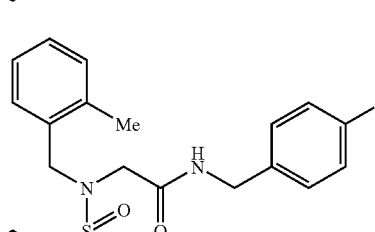 |
TABLE 13
| Pre | Str |
|---|---|
| 21 | 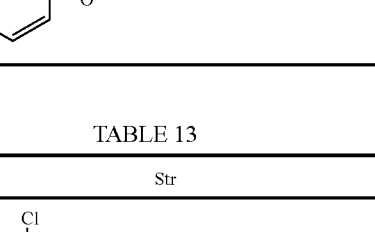 |
| 22 | 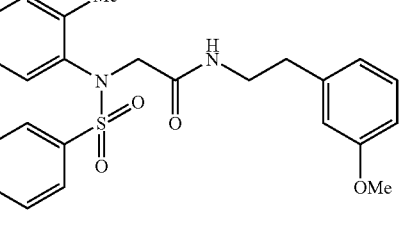 |

TABLE 13-continued

| Pre | Str |
|---|---|
| 23 | 3-Cl, 2-Me-phenyl-N(SO2-4-Me-phenyl)-CH2-C(O)NH-CH2-4-(hydroxymethyl)phenyl |
| 24 | 3-Cl, 2-Me-phenyl-N(SO2-4-MeO2C-phenyl)-CH2-C(O)NH-CH2-4-MeO-phenyl |
| 25 | 3-Cl, 2-Me-phenyl-N(SO2-4-HO2C-phenyl)-CH2-C(O)NH-CH2-4-MeO-phenyl |
| 26 | 3-Cl, 2-Me-phenyl-N(SO2-4-Cl-phenyl)-CH2-C(O)NH-CH2-4-MeO-phenyl |
| 27 | 3-Cl, 2-Me-phenyl-N(SO2-4-NC-phenyl)-CH2-C(O)NH-CH2-4-MeO-phenyl |
| 28 | 3-Cl, 2-Me-phenyl-N(SO2-4-F3C-phenyl)-CH2-C(O)NH-CH2-4-MeO-phenyl |
| 29 | 3-Cl, 2-Me-phenyl-N(SO2-4-MeO-phenyl)-CH2-C(O)NH-CH2-4-MeO-phenyl |
| 30 | 3-Cl, 2-Me-phenyl-N(SO2-4-Et-phenyl)-CH2-C(O)NH-CH2-4-MeO-phenyl |

TABLE 14

| Pre | Str |
|---|---|
| 31 | 3-Cl, 2-Me-phenyl-N(SO2-4-Ac-phenyl)-CH2-C(O)NH-CH2-4-MeO-phenyl |
| 32 | 3-Cl, 2-Me-phenyl-N(SO2-4-(MeO2C-CH2CH2)-phenyl)-CH2-C(O)NH-CH2-4-MeO-phenyl |

TABLE 14-continued
| Pre | Str |
|---|---|
| 33 | 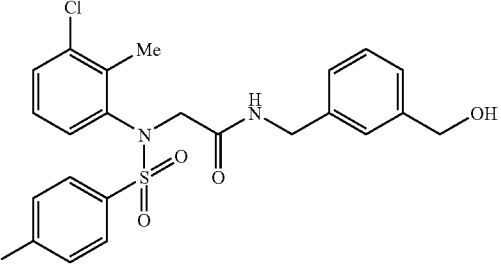 |
| 34 | 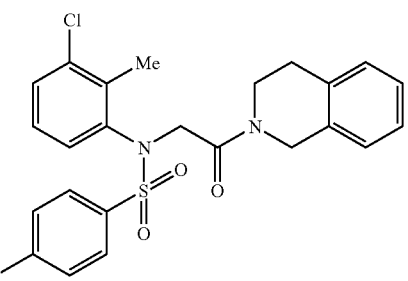 |
| 35 | 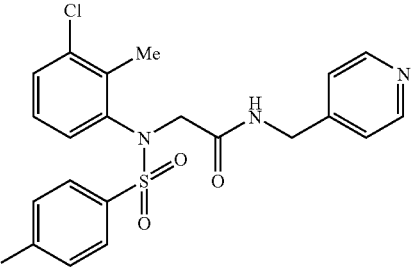 |
| 36 | 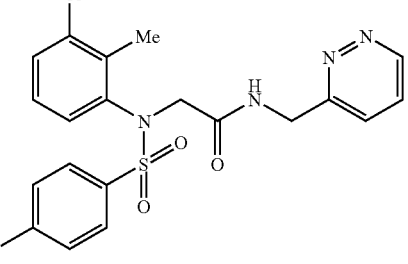 |
| 37 | 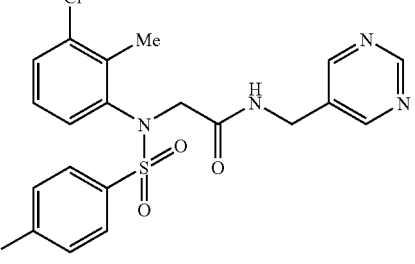 |
TABLE 14-continued
| Pre | Str |
|---|---|
| 38 | 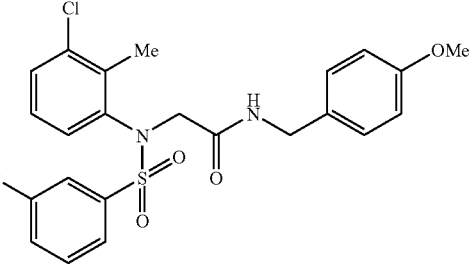 |
| 39 |  |
| 40 | 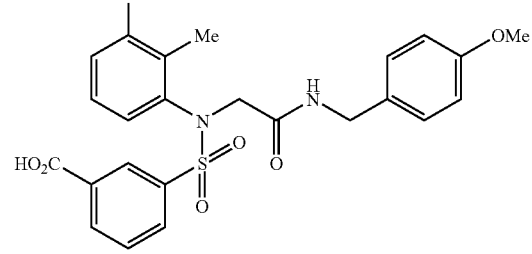 |
TABLE 15
| Pre | Str |
|---|---|
| 41 |  |
| 42 |  |

TABLE 15-continued

| Pre | Str |
|---|---|
| 43 | 2,3-dichlorophenyl-N-(tosyl)-glycine N-(4-methoxybenzyl)amide |
| 44 | 2-ethylphenyl-N-(tosyl)-glycine N-(4-methoxybenzyl)amide |
| 45 | 3-methyl-2-nitrophenyl-N-(tosyl)-glycine N-(4-methoxybenzyl)amide |
| 46 | 2-bromo-3-methylphenyl-N-(tosyl)-glycine N-(4-methoxybenzyl)amide |
| 47 | 2,3-dihydro-1H-inden-4-yl-N-(tosyl)-glycine N-(4-methoxybenzyl)amide |
| 48 | 3-chloro-2-methylphenyl-N-(3-(hydroxymethyl)phenylsulfonyl)-glycine N-(4-methoxybenzyl)amide |
| 49 | 3-chloro-2-methylphenyl-N-(tosyl)-glycine N-(3-hydroxybenzyl)amide |
| 50 | 3-chloro-2-methylphenyl-N-(tosyl)-glycine N-(4-isopropoxybenzyl)amide |

TABLE 16

| Pre | Str |
|---|---|
| 51 | 3-chloro-2-methylphenyl-N-(tosyl)-glycine N-(4-fluorobenzyl)amide |
| 52 | 3-chloro-2-methylphenyl-N-(tosyl)-glycine N-(furan-2-ylmethyl)amide |

TABLE 16-continued
| Pre | Str |
|-----|-----|
| 53 | |
| 54 | |
| 55 | |
| 56 | |
| 57 | |
| 58 | |
| 59 | |
| 60 | |
TABLE 17
| Pre | Str |
|-----|-----|
| 61 | |
| 62 | |
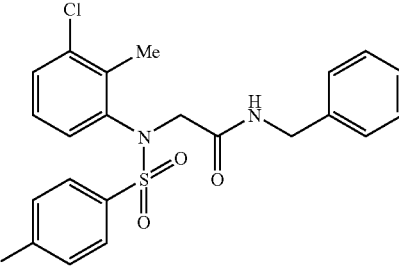

TABLE 17-continued
| Pre | Str |
|---|---|
| 63 | 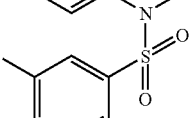 |
| 64 | 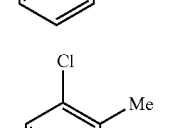 |
| 65 | 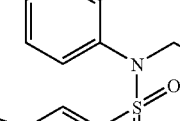 |
| 66 | 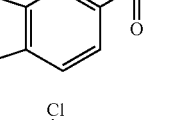 |
| 67 | 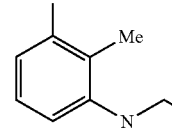 |
| 68 | 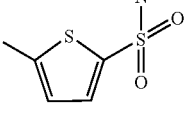 |
| 69 | 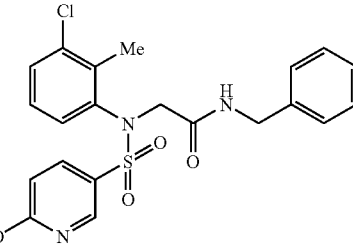 |
| 70 | 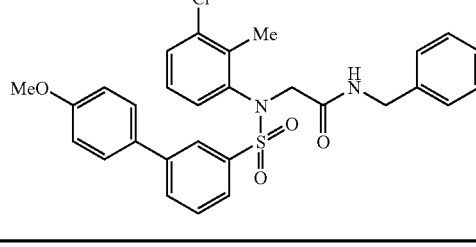 |
TABLE 18
| Pre | Str |
|---|---|
| 71 | 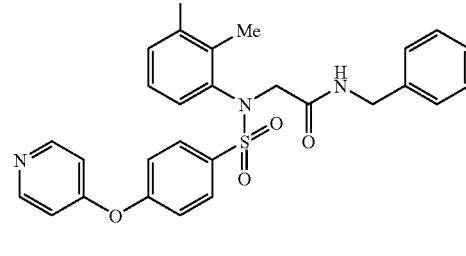 |
| 72 | 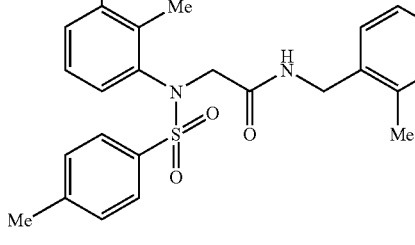 |
| 73 | 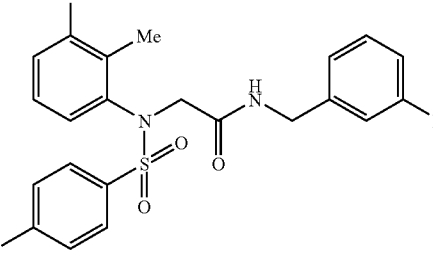 |

TABLE 18-continued

| Pre | Str |
|---|---|
| 74 | (structure) |
| 75 | (structure) |
| 76 | (structure) |
| 77 | (structure) |
| 78 | (structure) |
| 79 | (structure) |
| 80 | (structure) |

TABLE 19

| Pre | Str |
|---|---|
| 81 | (structure) |
| 82 | (structure) |
| 83 | (structure) |

TABLE 19-continued
| Pre | Str |
|---|---|
| 84 | 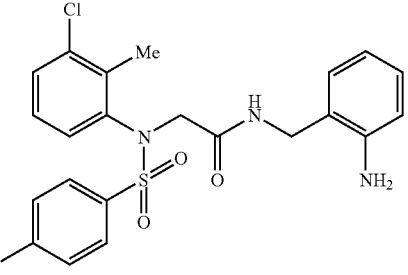 |
| 85 | 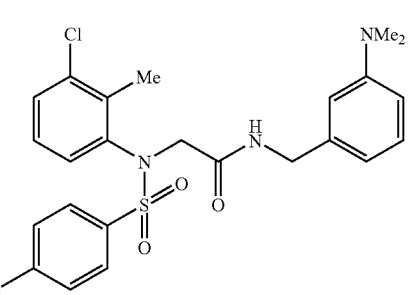 |
| 86 | 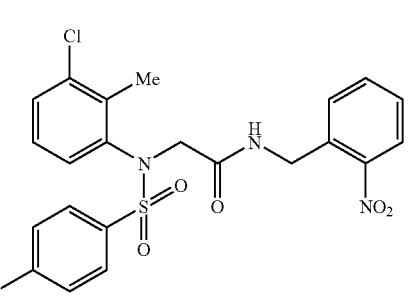 |
| 87 | 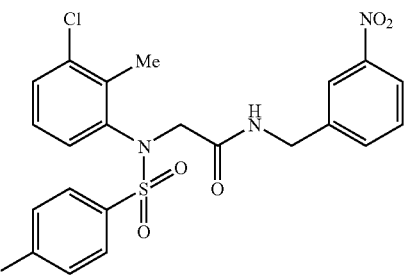 |
| 88 | 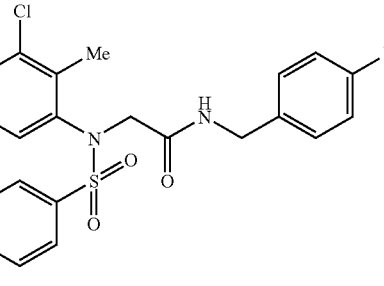 |
| 89 | 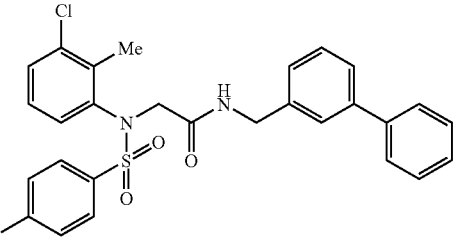 |
| 90 | 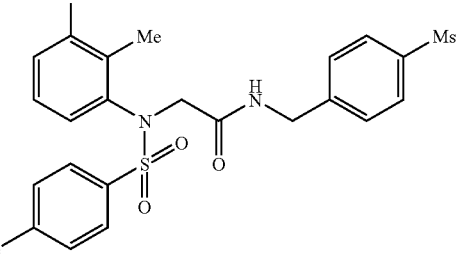 |
TABLE 20
| Pre | Str |
|---|---|
| 91 | 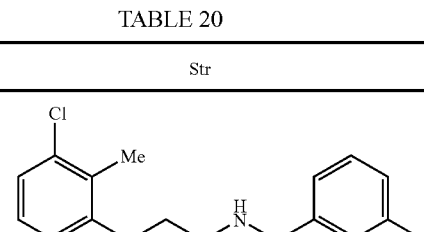 |
| 92 | 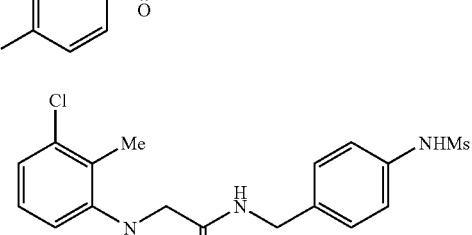 |
| 93 | 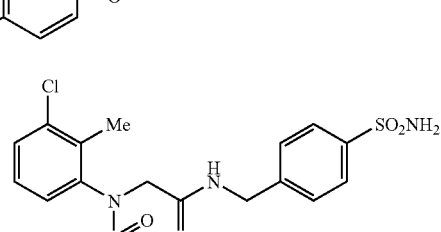 |

TABLE 20-continued

| Pre | Str |
|---|---|
| 94 | (structure) |
| 95 | (structure) |
| 96 | (structure) |
| 97 | (structure) |
| 98 | (structure) |

TABLE 20-continued

| Pre | Str |
|---|---|
| 99 | (structure) |
| 100 | (structure) |

TABLE 21

| Pre | Str |
|---|---|
| 101 | (structure) |
| 102 | (structure) |
| 103 | (structure) |

TABLE 21-continued

| Pre | Str |
|---|---|
| 104 | (structure) |
| 105 | (structure) |
| 106 | (structure) |
| 107 | (structure) |
| 108 | (structure) |
| 109 | (structure) |
| 110 | (structure) |

TABLE 22

| Pre | Str |
|---|---|
| 111 | (structure) |
| 112 | (structure) |
| 113 | (structure) |

TABLE 22-continued

| Pre | Str |
|---|---|
| 114 | 3-Cl, 2-OMe-phenyl-N(Ts)-CH2-C(O)-NH-CH2-(4-OMe-phenyl) |
| 115 | indol-7-yl-N(Ts)-CH2-C(O)-NH-CH2-(4-OMe-phenyl) |
| 116 | 2-Me-phenyl-N(Ts)-CH2-C(O)-NH-CH2-(4-OMe-phenyl) |
| 117 | 3-Cl, 2-Me-phenyl-N(Ts)-CH2-C(O)-NH-CH2-CH(Me)-CH2-Me |
| 118 | 3-Cl, 2-Me-phenyl-N(Ts)-CH2-C(O)-NH-CH2CH2-(pyrrol-1-yl) |
| 119 | 3-Cl, 2-Me-phenyl-N(Ts)-CH2-C(O)-NH-CH2-(3-SO2NH2-phenyl) |
| 120 | 3-Cl, 2-Me-phenyl-N(Ts)-CH2-C(O)-NH-CH2-(3-SO2NH-CH2CH2OH-phenyl) |
| 121 | 3-Cl, 2-Me-phenyl-N(Ts)-CH2-C(O)-NH-CH2-(3-SO2NH-CH2CH2NMe2-phenyl) |
| 122 | 3-Cl, 2-Me-phenyl-N(Ts)-CH2-C(O)-NH-CH2-(3-CN-phenyl) |

TABLE 23

| Ex | Str |
|---|---|
| 1 | 3-Cl, 2-Me-phenyl-N(Ts)-CH2-C(O)-NH-CH2-(4-CO2H-phenyl) |

TABLE 23-continued

| Ex | Str |
|---|---|
| 2 | (structure) |
| 3 | (structure) |
| 4 | (structure) |
| 5 | (structure) |
| 6 | (structure) |
| 7 | (structure) |
| 8 | (structure) |
| 9 | (structure) |
| 10 | (structure) |

TABLE 24

| Ex | Str |
|---|---|
| 11 | (structure) |

TABLE 24-continued

| Ex | Str |
|---|---|
| 12 | 3-chloro-2-methylphenyl-N-(tosyl)glycine-N-(3-carboxymethylbenzyl)amide |
| 13 | 3-chloro-2-methylphenyl-N-(tosyl)-β-alanine-N-(3-carboxybenzyl)amide |
| 14 | 3-chloro-2-methylphenyl-N-(tosyl)-γ-aminobutyric acid-N-(3-carboxybenzyl)amide |
| 15 | (3-chloro-2-methylbenzyl)-N-(tosyl)glycine-N-(3-carboxybenzyl)amide |
| 16 | 3-chloro-2-methylphenyl-N-(tosyl)glycine-N-(3-(carboxymethoxy)benzyl)amide |

TABLE 24-continued

| Ex | Str |
|---|---|
| 17 | 3-chloro-2-methylphenyl-N-(tosyl)glycine-N-(3-methoxycarbonylbenzyl)amide |
| 18 | 3-chloro-2-methylphenyl-N-(tosyl)glycine-N-(4-carboxy-3-methoxybenzyl)amide |
| 19 | 3-chloro-2-methylphenyl-N-(tosyl)-alanine-N-(3-carboxybenzyl)amide |
| 20 | 3-chloro-2-methylphenyl-N-(tosyl)glycine-N-(4-(methanesulfonylcarbamoyl)benzyl)amide |

TABLE 25

| Ex | Str |
|---|---|
| 21 | 3-chloro-2-methylphenyl-N-((4-cyanophenyl)sulfonyl)glycine-N-(3-carboxybenzyl)amide |

TABLE 25-continued
| Ex | Str |
|---|---|
| 22 | 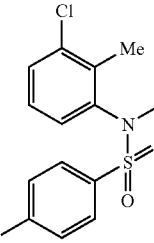 |
| 23 | |
| 24 | |
| 25 | |
| 26 | |
TABLE 25-continued
| Ex | Str |
|---|---|
| 27 | 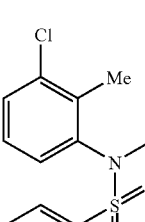 |
| 28 | |
| 29 | |
| 30 | |
TABLE 26
| Ex | Str |
|---|---|
| 31 | |

TABLE 26-continued

| Ex | Str |
|---|---|
| 32 | (structure) |
| 33 | (structure) |
| 34 | (structure) |
| 35 | (structure) |
| 36 | (structure) |「

TABLE 26-continued

| Ex | Str |
|---|---|
| 37 | (structure) |
| 38 | (structure) |
| 39 | (structure) |
| 40 | (structure) |

TABLE 27

| Ex | Str |
|---|---|
| 41 | (structure) |

TABLE 27-continued

| Ex | Str |
|---|---|
| 42 | (structure) |
| 43 | (structure) |
| 44 | (structure) |
| 45 | (structure) |
| 46 | (structure) |
| 47 | (structure) |
| 48 | (structure) |
| 49 | (structure) |
| 50 | (structure) |

TABLE 28

| Ex | Str |
|---|---|
| 51 | (3-chloro-2-methylphenyl)[(4-methylphenyl)sulfonyl]amino-acetamide linked to 3-(carboxyethyl)benzylamine |
| 52 | (3-chloro-2-methylphenyl)[(4-methylphenyl)sulfonyl]amino-acetamide linked to 4-((E)-2-carboxyvinyl)benzylamine |
| 53 | (3-chloro-2-methylphenyl)[(4-methylphenyl)sulfonyl]amino-acetamide linked to 4-(carboxyethyl)benzylamine |
| 54 | (3-chloro-2-methylphenyl)[(4-methylphenyl)sulfonyl]amino-acetamide linked to 4-[(3-hydroxypropylsulfonyl)aminocarbonyl]benzylamine |
| 55 | (3-chloro-2-methylphenyl)[(4-methylphenyl)sulfonyl]amino-acetamide linked to 3-[(2-hydroxyethyl)aminocarbonyl]benzylamine |

TABLE 28-continued
| Ex | Str |
|---|---|
| 56 | 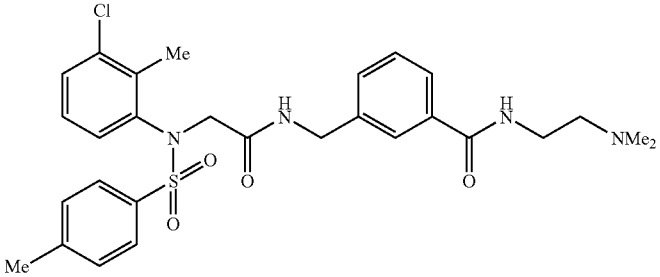 |
| 57 | 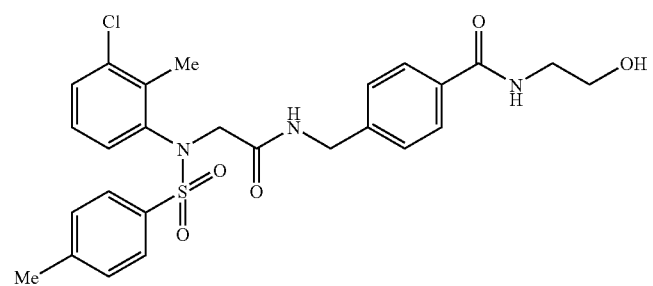 |
| 58 | 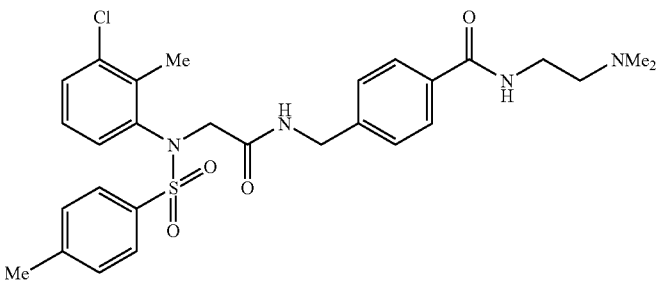 |
| 59 | 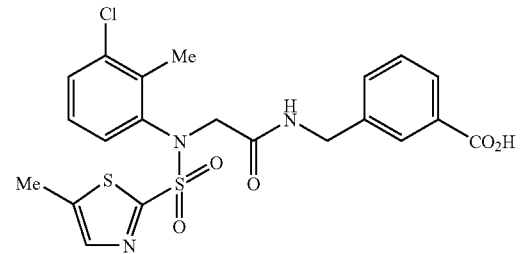 |
| 60 | 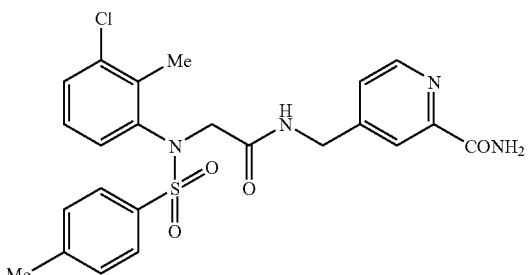 |

TABLE 29
| Ex | Str |
|---|---|
| 61 | 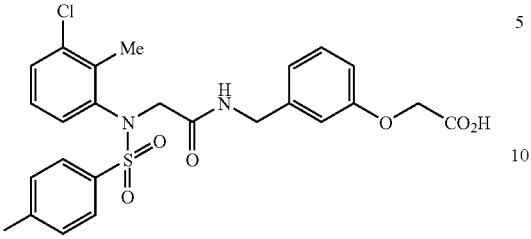 |
| 62 | 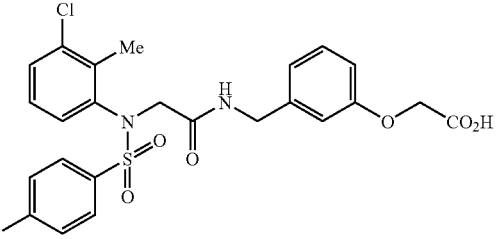 |
| 63 | 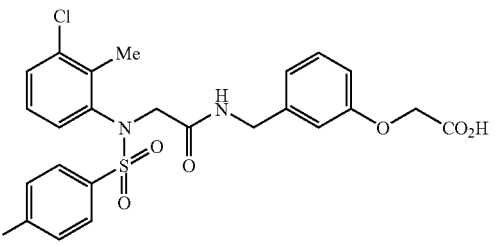 |
| 64 | 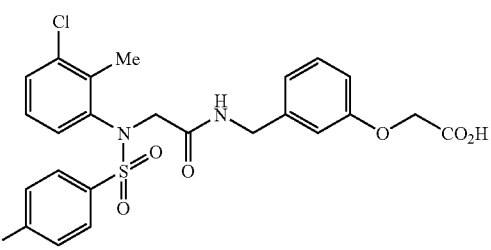 |
| 65 | 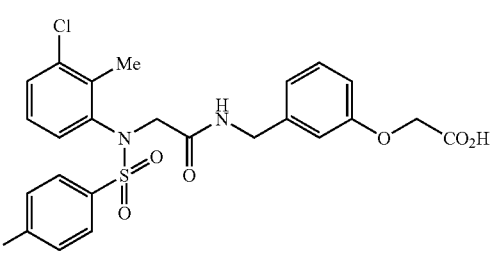 |
| 66 | 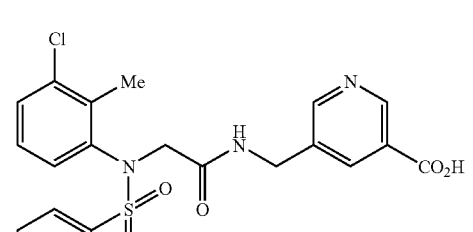 |
TABLE 29-continued
| Ex | Str |
|---|---|
| 67 | 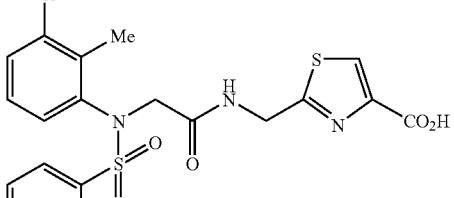 |
| 68 | 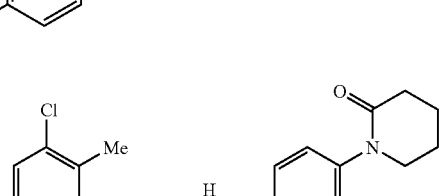 |
| 69 | 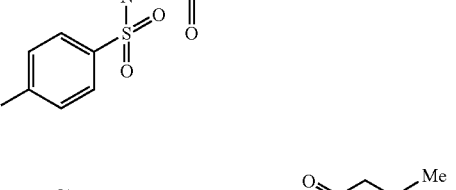 |
| 70 | 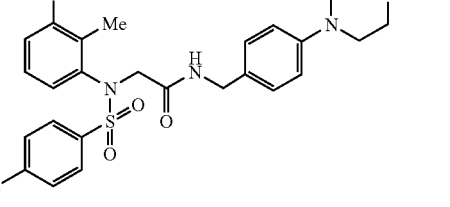 |
TABLE 30
| Ex | Str |
|---|---|
| 71 | 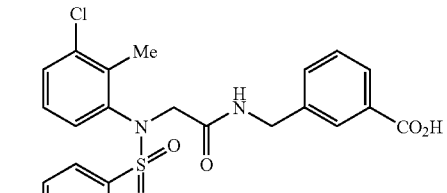 |

TABLE 30-continued
| Ex | Str |
|---|---|
| 72 | 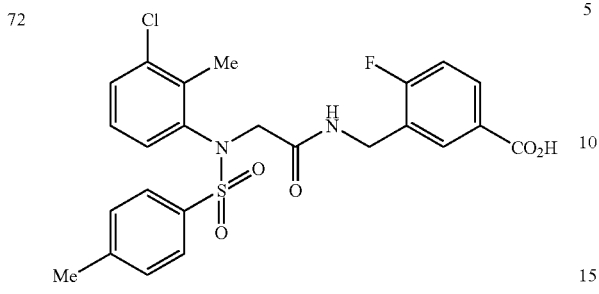 |
| 73 | 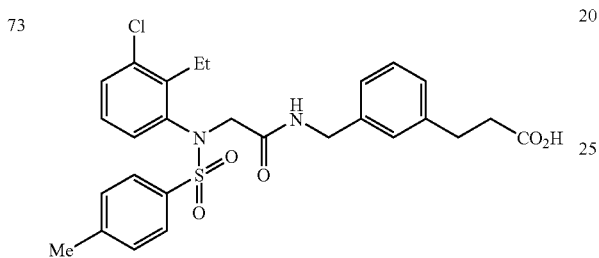 |
| 74 | 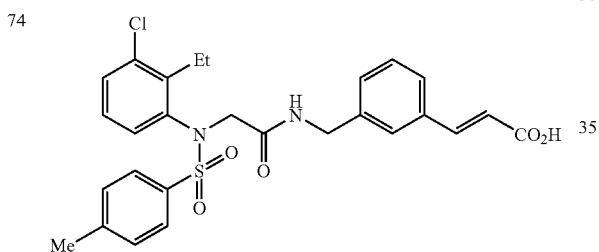 |
| 75 | 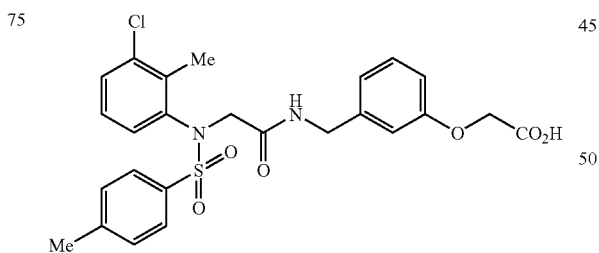 |
| 76 | 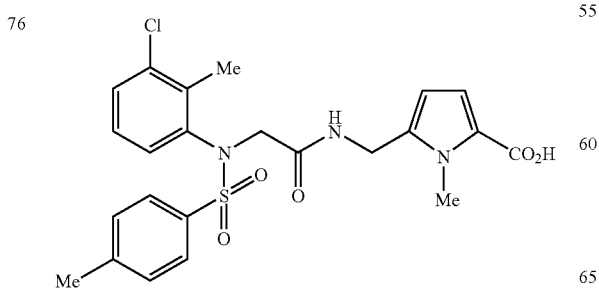 |
| 77 | 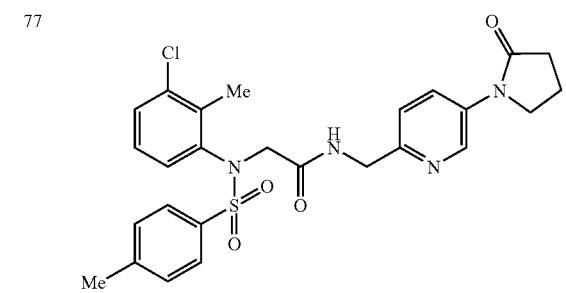 |
| 78 | 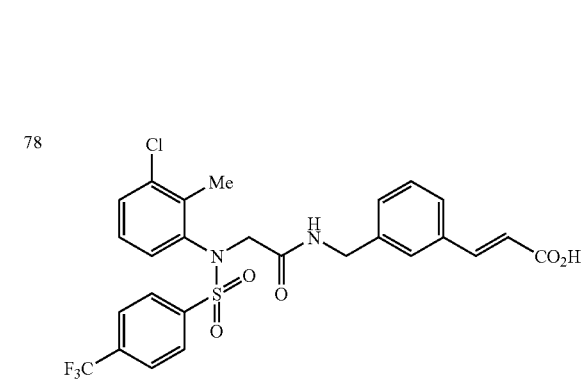 |
| 79 | 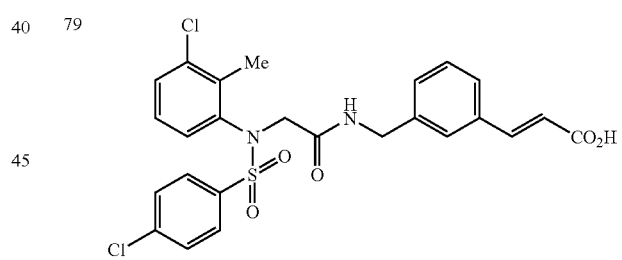 |
| 80 | 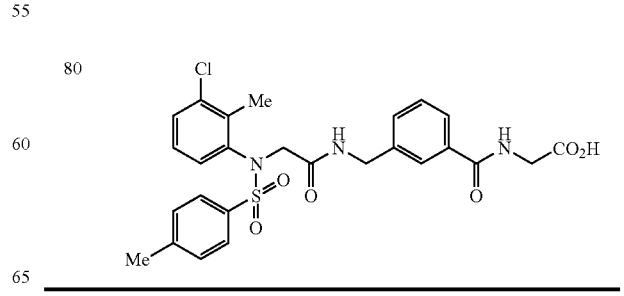 |

TABLE 31
| Ex | Str |
|---|---|
| 81 | 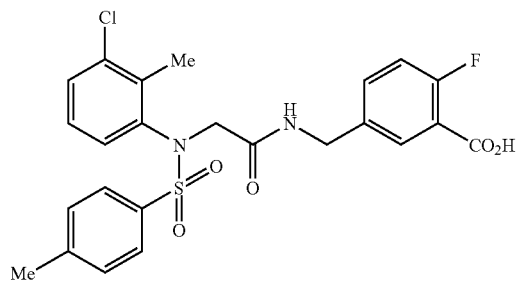 |
| 82 | 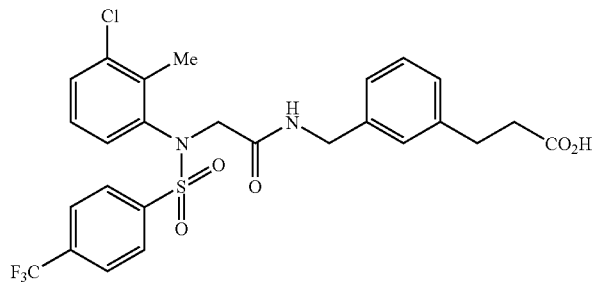 |
| 83 | 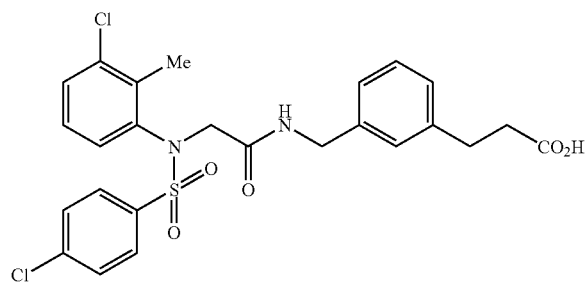 |
| 84 | 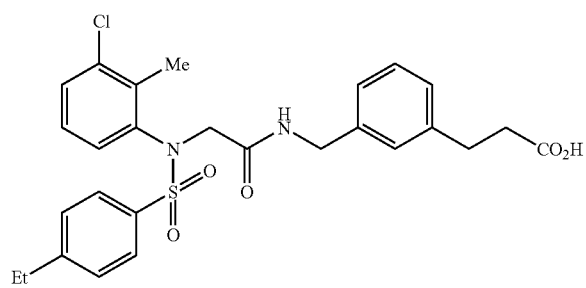 |
| 85 | 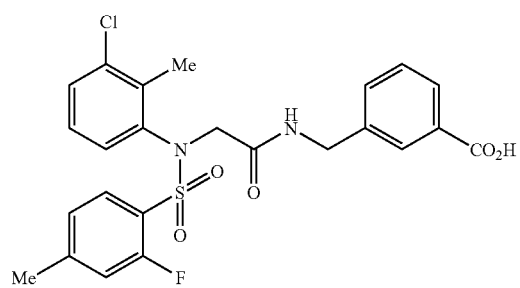 |

TABLE 31-continued

| Ex | Str |
|---|---|
| 86 | 3-chloro-2-methylphenyl group with N-sulfonyl(4-ethylphenyl) and N-CH2C(O)NH-CH2-(3-(CH=CH-CO2H)phenyl) |
| 87 | 3-chloro-2-methylphenyl group with N-sulfonyl(4-fluoro-2-methylphenyl) and N-CH2C(O)NH-CH2-(3-CO2H-phenyl) |
| 88 | 3-chloro-2-methylphenyl group with N-sulfonyl(3-fluoro-4-methylphenyl) and N-CH2C(O)NH-CH2-(3-CO2H-phenyl) |
| 89 | 3-chloro-2-methylphenyl group with N-tosyl and N-CH2C(O)NH-CH2-(3-C(O)NH-CH2CH(OH)CH2OH-phenyl) |
| 90 | 3-chloro-2-methylphenyl group with N-tosyl and N-CH2C(O)NH-CH2-(4-C(O)NH-CH2CH(OH)CH2OH-phenyl) |

TABLE 32

| Ex | Str |
|----|-----|
| 91 | |
| 92 | |
| 93 | |
| 94 | |
| 95 | |

TABLE 32-continued

| Ex | Str |
|---|---|
| 96 | (structure) |
| 97 | (structure) |
| 98 | (structure) |
| 99 | (structure) |
| 100 | (structure) |

TABLE 33
| Ex | Str |
|---|---|
| 101 | 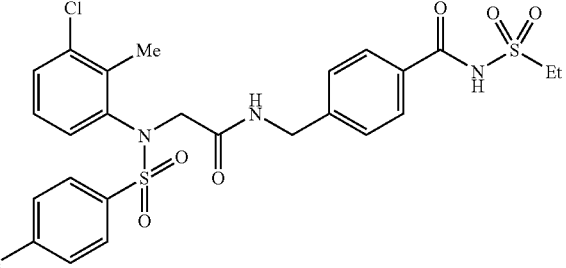 |
| 102 | 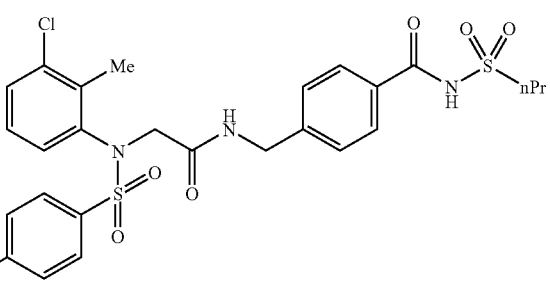 |
| 103 | 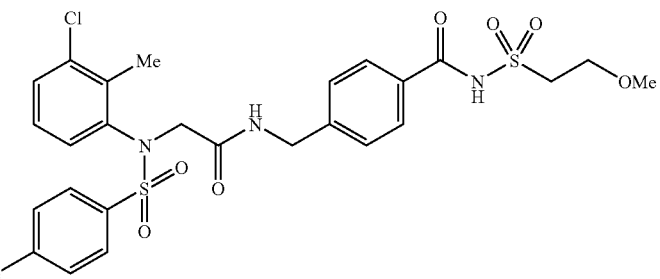 |
| 104 | 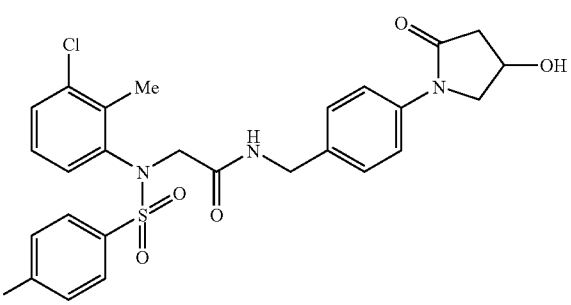 |
| 105 | 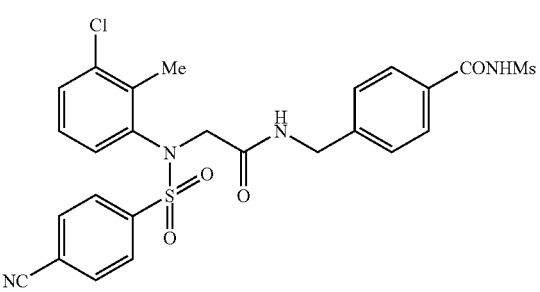 |

TABLE 33-continued

| Ex | Str |
|---|---|
| 106 | 3-Cl, 2-Me-phenyl-N(SO2-4-Et-C6H4)-CH2-C(O)-NH-CH2-(4-CONHMs-phenyl) |
| 107 | 3-Cl, 2-Me-phenyl-N(SO2-4-Cl-C6H4)-CH2-C(O)-NH-CH2-(4-CONHMs-phenyl) |
| 108 | 3-Cl, 2-Me-phenyl-N(SO2-4-CF3-C6H4)-CH2-C(O)-NH-CH2-(4-CONHMs-phenyl) |
| 109 | 3-Cl, 2-Me-phenyl-N(SO2-4-CN-C6H4)-CH2-C(O)-NH-CH2-[5-(2-oxopyrrolidin-1-yl)pyridin-2-yl] · HCl |
| 110 | 3-Cl, 2-Me-phenyl-N(SO2-4-CF3-C6H4)-CH2-C(O)-NH-CH2-[5-(2-oxopyrrolidin-1-yl)pyridin-2-yl] |

TABLE 34
| Ex | Str |
|---|---|
| 111 | 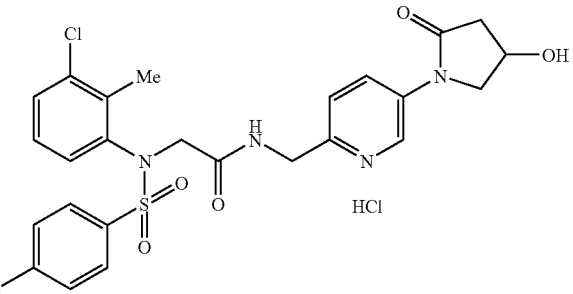 HCl |
| 112 | 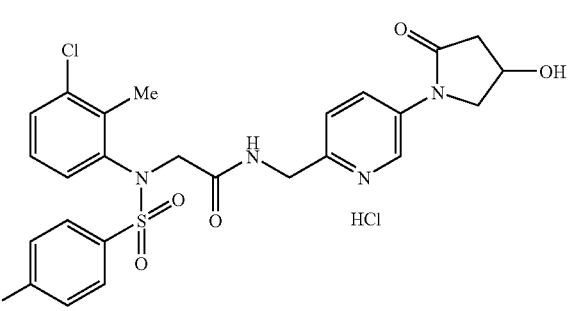 HCl |
| 113 | 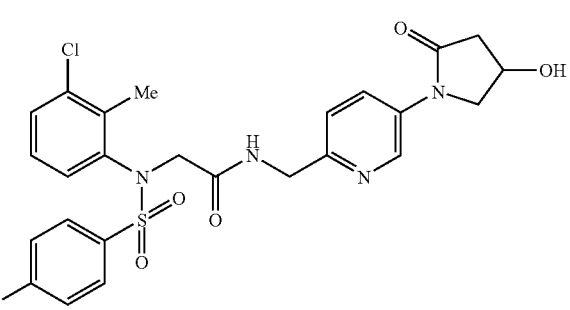 |
| 114 | 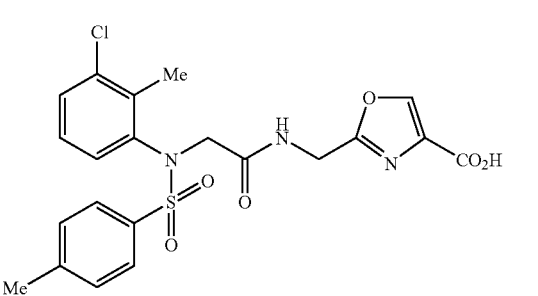 |
| 115 | 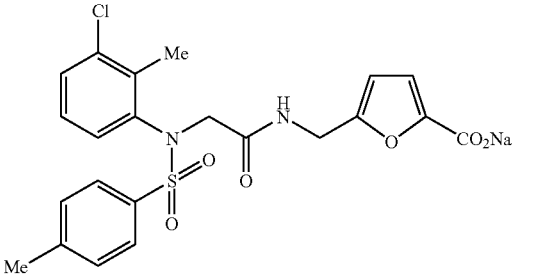 |

TABLE 34-continued
| Ex | Str |
|---|---|
| 116 | 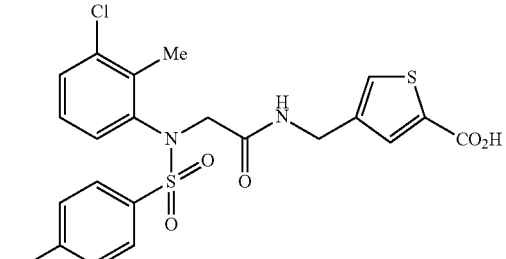 |
| 117 | 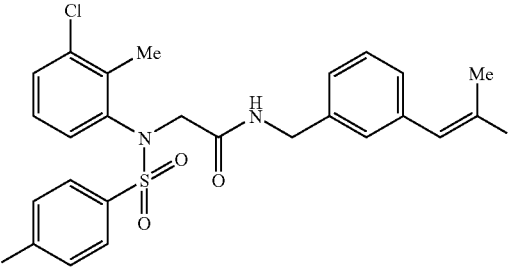 |
| 118 | 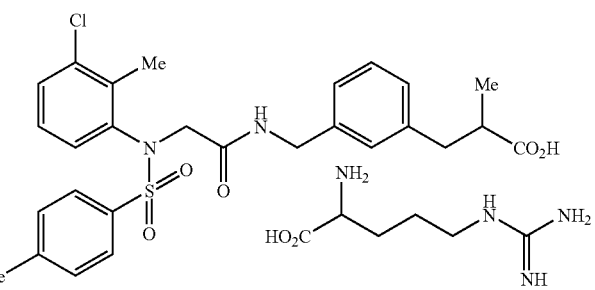 |
| 119 | 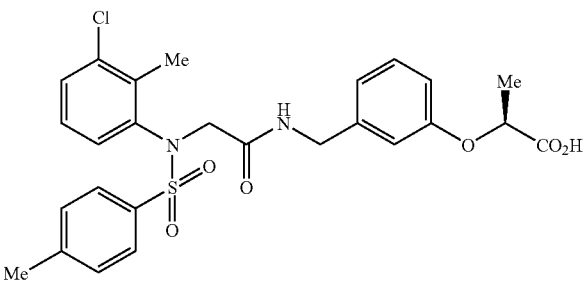 |
| 120 | 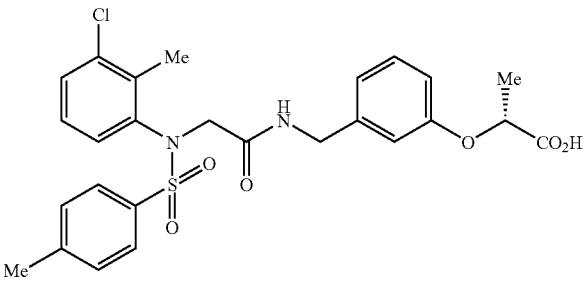 |

TABLE 35
| Ex | Str |
|---|---|
| 121 | 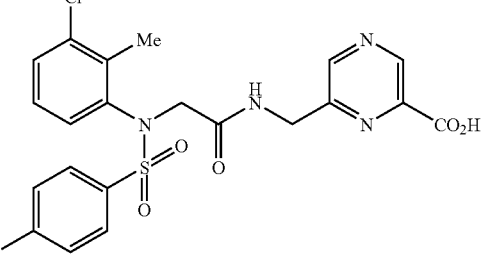 |
| 122 | 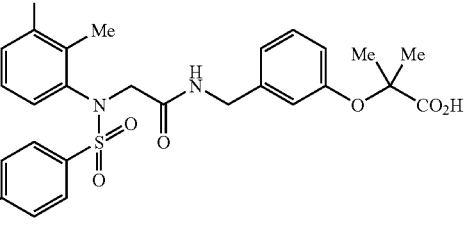 |
| 123 | 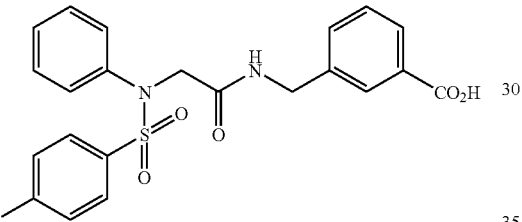 |
| 124 | 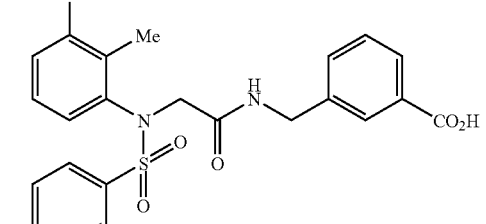 |
| 125 | 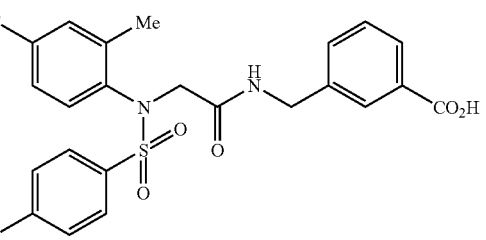 |
| 126 | 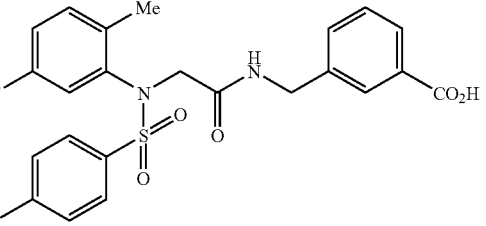 |
TABLE 35-continued
| Ex | Str |
|---|---|
| 127 | 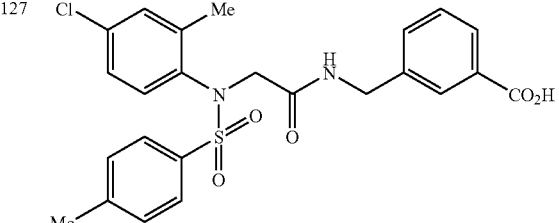 |
| 128 | 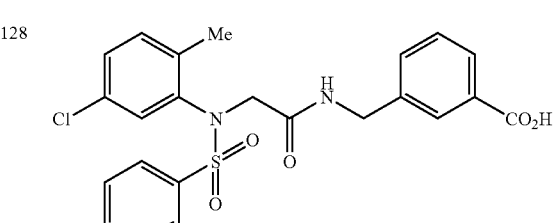 |
| 129 | 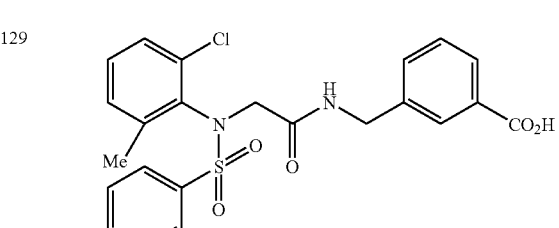 |
| 130 | |
TABLE 36
| Ex | Str |
|---|---|
| 131 | 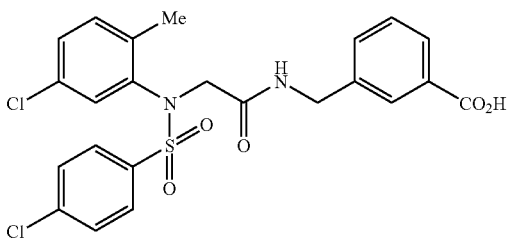 |

TABLE 36-continued

| Ex | Str |
|---|---|
| 132 | (4-bromo-2-methylphenyl, tosyl) |
| 133 | (5-bromo-2-methylphenyl, 4-chlorophenylsulfonyl) |
| 134 | (2-bromo-6-methylphenyl, tosyl) |
| 135 | (3-chloro-2-fluorophenyl, tosyl) |
| 136 | (3-chloro-2-(2-hydroxyethyl)phenyl, tosyl) |
| 137 | (2,3-dimethylphenyl, tosyl) |

TABLE 36-continued

| Ex | Str |
|---|---|
| 138 | (3-hydroxy-2-methylphenyl, tosyl) |
| 139 | (4-methoxy-2-methylphenyl, tosyl) |
| 140 | (5-methoxy-2-methylphenyl, tosyl) |

TABLE 37

| Ex | Str |
|---|---|
| 141 | (2-methoxy-6-methylphenyl, tosyl) |
| 142 | (3-trifluoromethyl-2-methylphenyl, tosyl) |

TABLE 37-continued

| Ex | Str |
|---|---|
| 143 | (structure) |
| 144 | (structure) |
| 145 | (structure) |
| 146 | (structure) |
| 147 | (structure) |
| 148 | (structure) |
| 149 | (structure) |
| 150 | (structure) |

TABLE 38

| Ex | Str |
|---|---|
| 151 | (structure) |
| 152 | (structure) |

TABLE 38-continued
| Ex | Str |
|---|---|
| 153 | 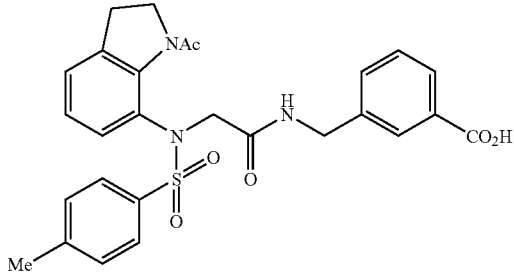 |
| 154 | 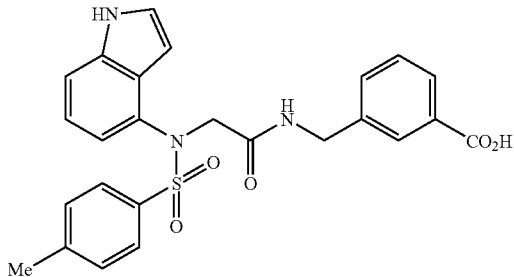 |
| 155 | 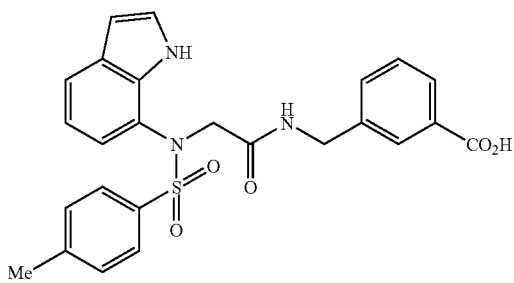 |
| 156 | 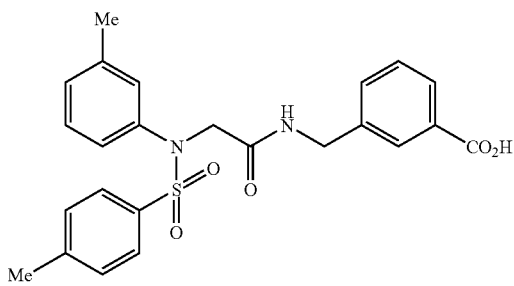 |
| 157 | 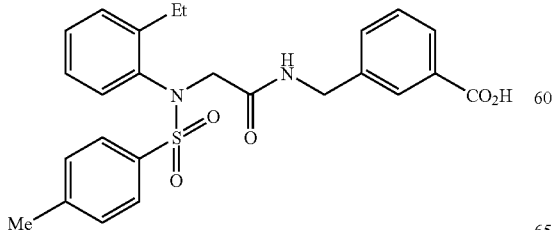 |
TABLE 38-continued
| Ex | Str |
|---|---|
| 158 | 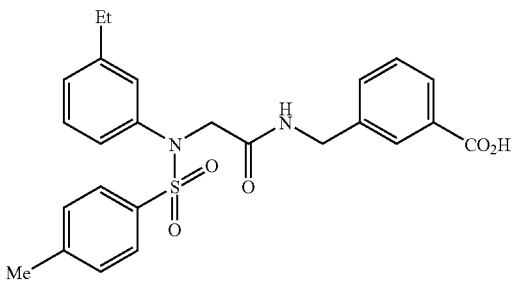 |
| 159 | 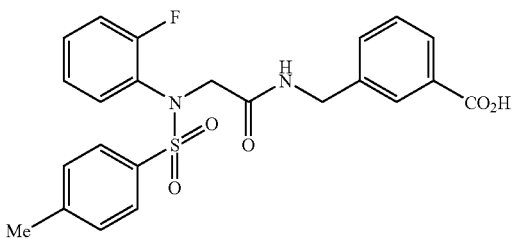 |
| 160 | 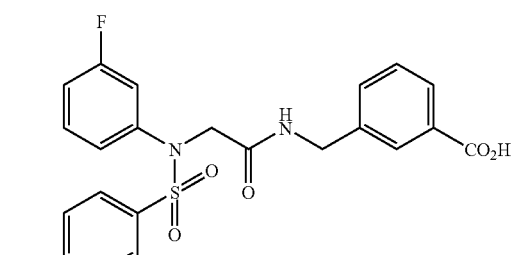 |
TABLE 39
| Ex | Str |
|---|---|
| 161 | 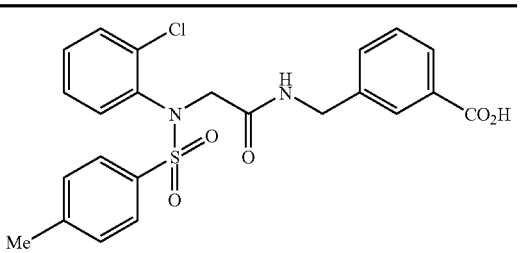 |
| 162 | 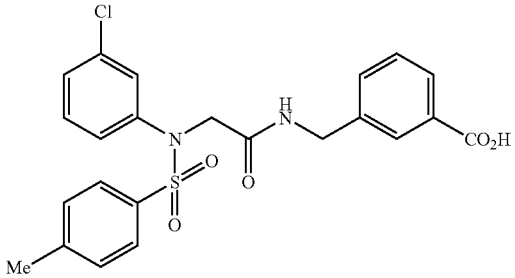 |

TABLE 39-continued
| Ex | Str |
|---|---|
| 163 | 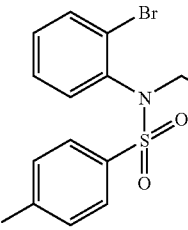 |
| 164 | 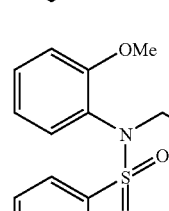 |
| 165 | 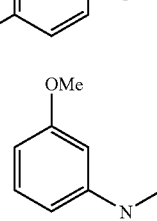 |
| 166 | 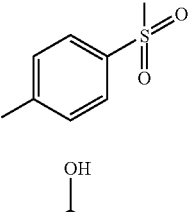 |
| 167 | 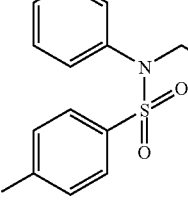 |
| 168 | 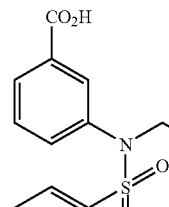 |
| 169 | |
| 170 | |
TABLE 40
| Ex | Str |
|---|---|
| 171 | |
| 172 | |
| 173 | |

TABLE 40-continued

| Ex | Str |
|---|---|
| 174 | (2-CONH2-phenyl)-N(Ts)-CH2-C(O)-NH-CH2-(3-CO2H-phenyl) |
| 175 | (2-NHAc-phenyl)-N(Ts)-CH2-C(O)-NH-CH2-(3-CO2H-phenyl) |
| 176 | (3-NHAc-phenyl)-N(Ts)-CH2-C(O)-NH-CH2-(3-CO2H-phenyl) |
| 177 | (3-CONH2-phenyl)-N(Ts)-CH2-C(O)-NH-CH2-(3-CO2H-phenyl) |
| 178 | (3-Ac-phenyl)-N(Ts)-CH2-C(O)-NH-CH2-(3-CO2H-phenyl) |

TABLE 40-continued

| Ex | Str |
|---|---|
| 179 | (2-piperidinyl-phenyl)-N(Ts)-CH2-C(O)-NH-CH2-(3-CO2H-phenyl) |
| 180 | (2-morpholinyl-phenyl)-N(Ts)-CH2-C(O)-NH-CH2-(3-CO2H-phenyl) |

TABLE 41

| Ex | Str |
|---|---|
| 181 | (3-Cl-2-Me-phenyl)-N(SO2-cyclopropyl)-CH2-C(O)-NH-CH2-(3-CO2H-phenyl) |
| 182 | (3-Cl-2-Me-phenyl)-N(SO2-cyclopentyl)-CH2-C(O)-NH-CH2-(3-CO2H-phenyl) |
| 183 | (3-Cl-2-Me-phenyl)-N(SO2-phenyl)-CH2-C(O)-NH-CH2-(3-CO2H-phenyl) |

TABLE 41-continued

| Ex | Str |
|---|---|
| 184 | 3-chloro-2-methyl-N-(1-methyl-1H-pyrazol-4-ylsulfonyl)phenyl-glycine 3-carboxybenzylamide |
| 185 | 3-chloro-2-methyl-N-(thiophen-2-ylsulfonyl)phenyl-glycine 3-carboxybenzylamide |
| 186 | 3-chloro-2-methyl-N-(thiophen-3-ylsulfonyl)phenyl-glycine 3-carboxybenzylamide |
| 187 | 3-chloro-2-methyl-N-(cyclohexylsulfonyl)phenyl-glycine 3-carboxybenzylamide |
| 188 | 3-chloro-2-methyl-N-(3-methylphenylsulfonyl)phenyl-glycine 3-carboxybenzylamide |

TABLE 41-continued

| Ex | Str |
|---|---|
| 189 | 3-chloro-2-methyl-N-(5-methylthiophen-2-ylsulfonyl)phenyl-glycine 3-carboxybenzylamide |
| 190 | 3-chloro-2-methyl-N-(3-methoxyphenylsulfonyl)phenyl-glycine 3-carboxybenzylamide |

TABLE 42

| Ex | Str |
|---|---|
| 191 | 3-chloro-2-methyl-N-(2-methoxyphenylsulfonyl)phenyl-glycine 3-carboxybenzylamide |
| 192 | 3-chloro-2-methyl-N-(pyridin-2-ylsulfonyl)phenyl-glycine 3-carboxybenzylamide |
| 193 | 3-chloro-2-methyl-N-(3-acetylphenylsulfonyl)phenyl-glycine 3-carboxybenzylamide |

TABLE 42-continued

| Ex | Str |
|---|---|
| 194 | (structure) |
| 195 | (structure) |
| 196 | (structure) |
| 197 | (structure) |

TABLE 42-continued

| Ex | Str |
|---|---|
| 198 | (structure) |
| 199 | (structure) |
| 200 | (structure) |

TABLE 43

| Ex | Str |
|---|---|
| 201 | (structure) |

TABLE 43-continued

| Ex | Str |
|---|---|
| 202 | 3-chloro-2-methylphenyl N-[(4-(3-methylureido)phenyl)sulfonyl]glycyl 3-carboxybenzylamide |
| 203 | 3-chloro-2-methylphenyl N-[(biphenyl-4-yl)sulfonyl]glycyl 3-carboxybenzylamide |
| 204 | 3-chloro-2-methylphenyl N-[(3-bromophenyl)sulfonyl]glycyl 3-carboxybenzylamide |
| 205 | 3-chloro-2-methylphenyl N-[(4-cyclohexylphenyl)sulfonyl]glycyl 3-carboxybenzylamide |
| 206 | 3-chloro-2-methylphenyl N-[(4-(2-methoxycarbonylethyl)phenyl)sulfonyl]glycyl 3-carboxybenzylamide |

TABLE 43-continued
| Ex | Str |
|---|---|
| 207 | 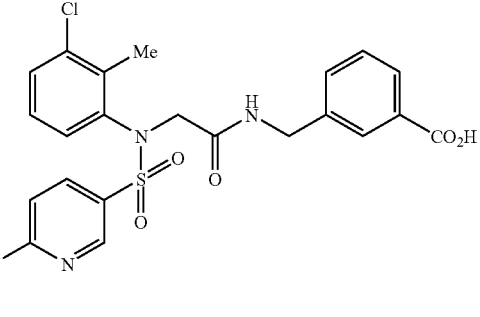 |
| 208 | 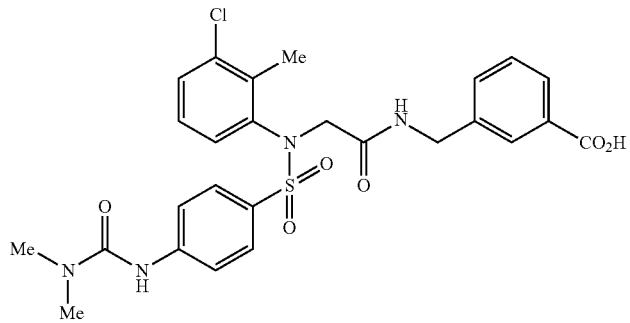 |
| 209 | 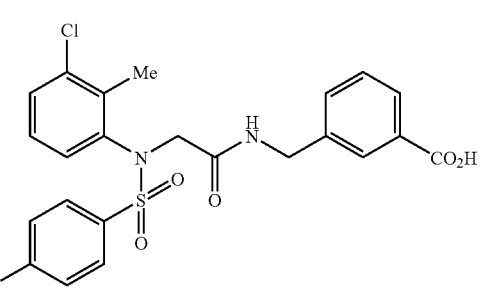 |
| 210 | 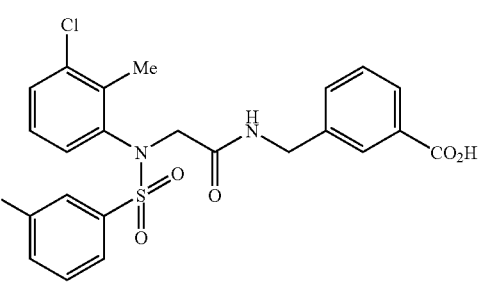 |

TABLE 44
| Ex | Str |
|---|---|
| 211 | 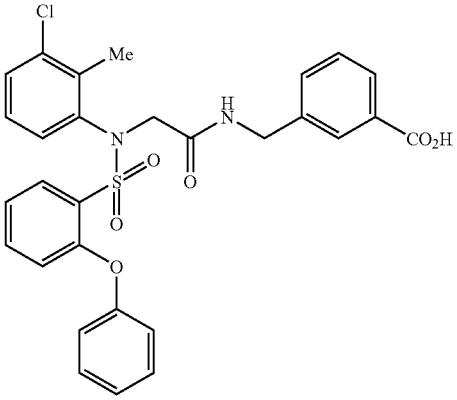 |
| 212 | 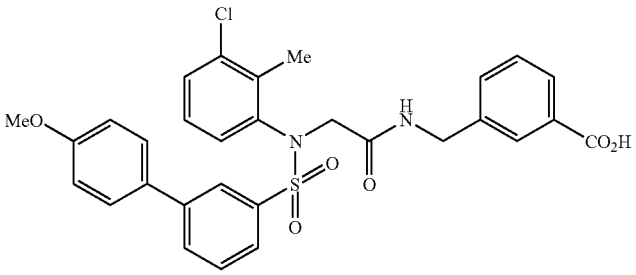 |
| 213 | 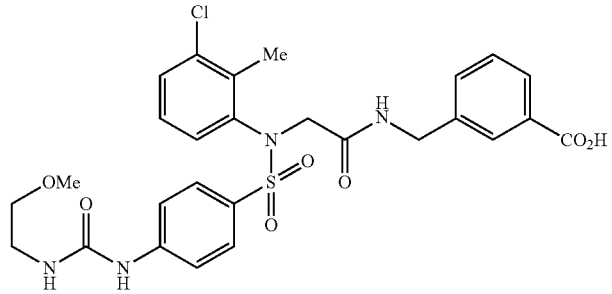 |
| 214 | 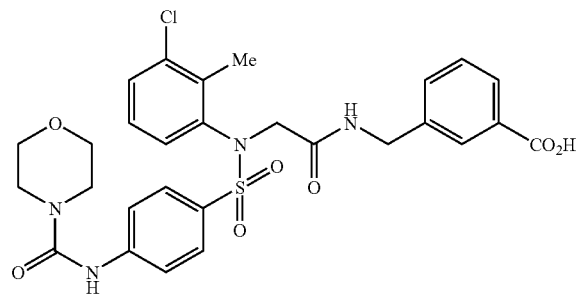 |
| 215 | 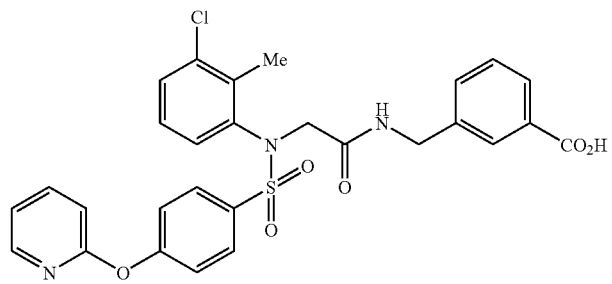 |

TABLE 44-continued
| Ex | Str |
|---|---|
| 216 | 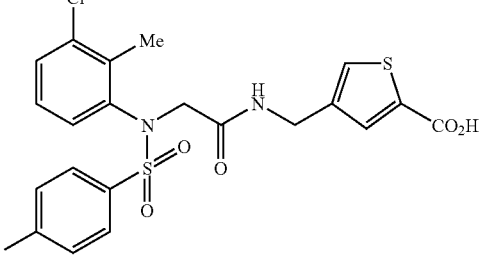 |
| 217 | 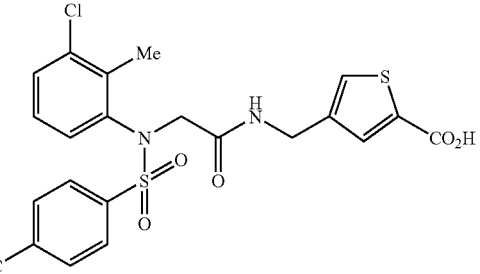 |
| 218 | 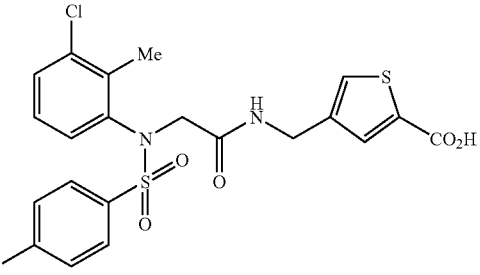 |
| 219 | 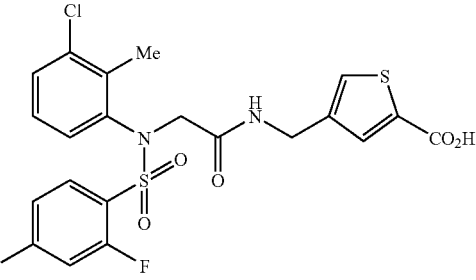 |
| 220 | 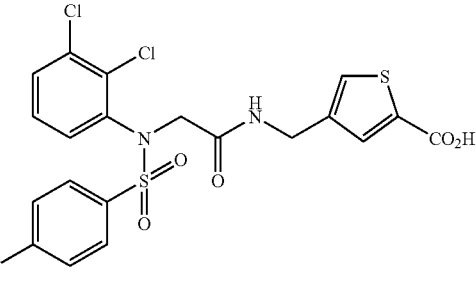 |

TABLE 45
| Ex | Str |
|---|---|
| 221 | 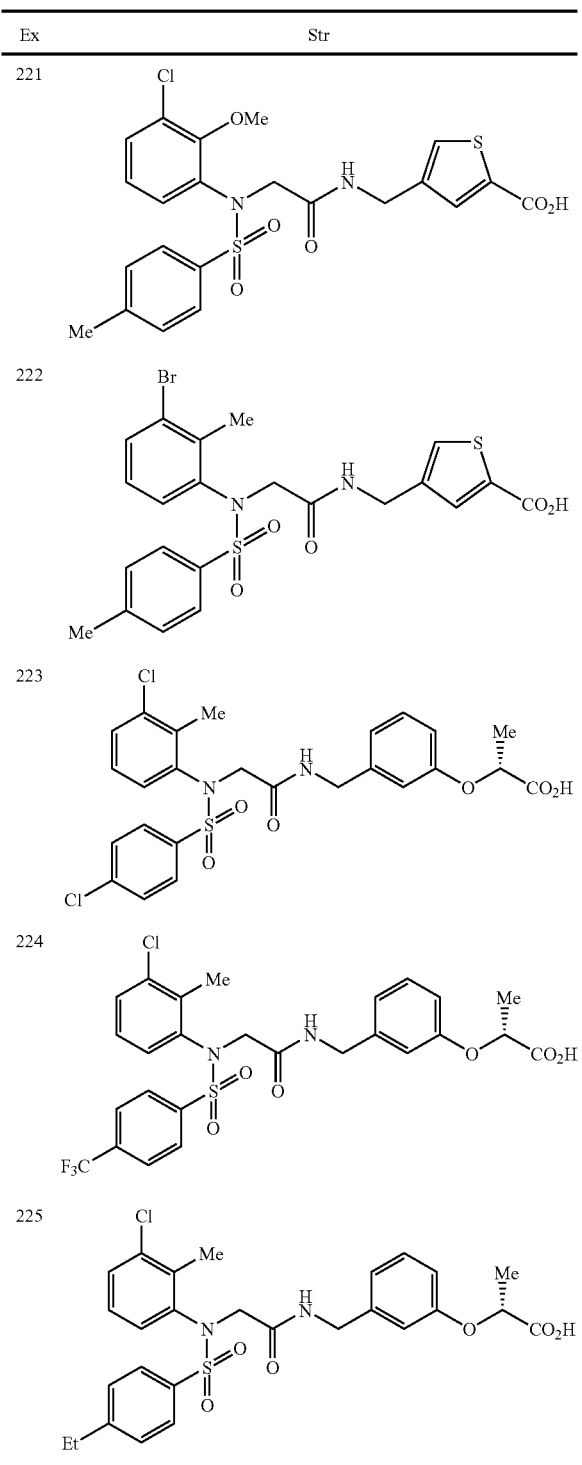 |
| 222 | |
| 223 | |
| 224 | |
| 225 | |
| 226 | |
TABLE 45-continued
| Ex | Str |
|---|---|
| 227 | 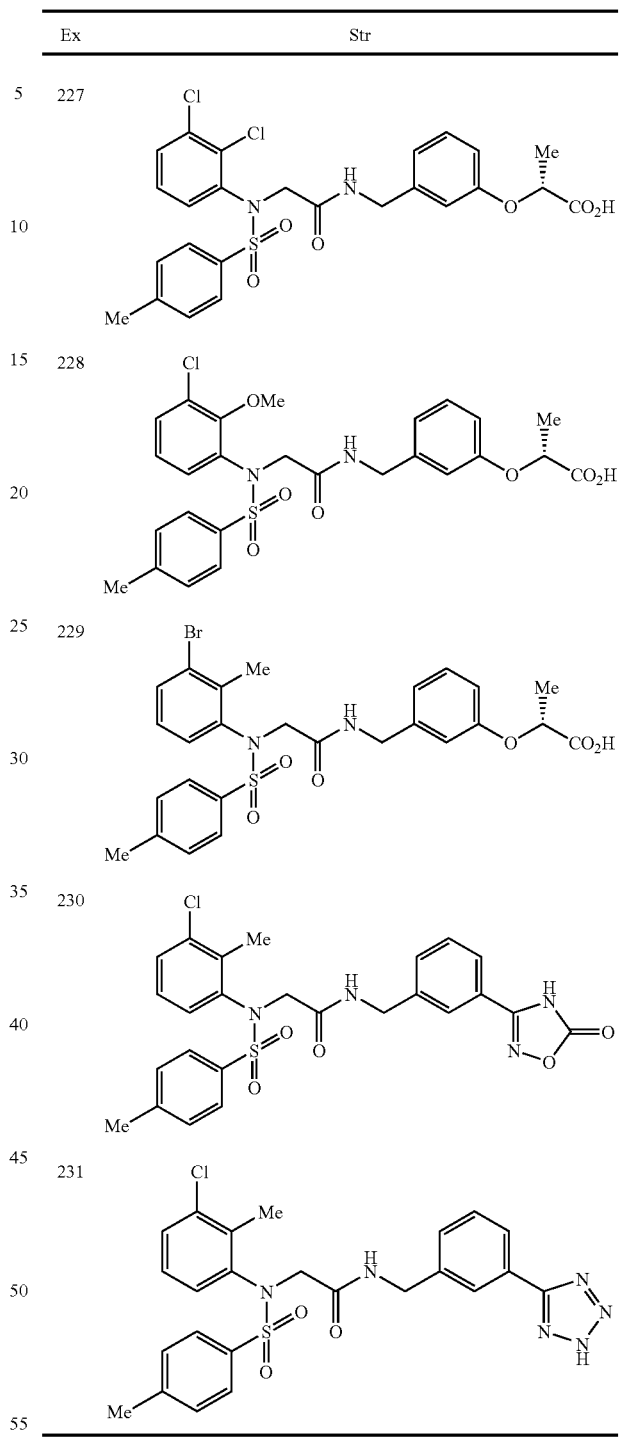 |
| 228 | |
| 229 | |
| 230 | |
| 231 | |
TABLE 46
| Pre | Syn | Dat |
|---|---|---|
| 1 | P1 | FP: 473 |
| 2 | P2 | FP: 477 |
| 3 | P3 | FP: 475 |
| 4 | P4 | FP: 459 [M]+ |
| 5 | P5 | FP: 489 |
| 6 | P6 | EP: 460 |
| 7 | P1 | FP: 444 |

TABLE 46-continued

| Pre | Syn | Dat |
|---|---|---|
| 8 | P1 | FP: 473 |
| 9 | P1 | FP: 473 |
| 10 | P1 | FP: 487 [M]+ |
| 11 | P1 | FP: 487 [M]+ |
| 12 | P1 | EP: 523 [M + Na]+ |
| 13 | P1 | FP: 480 [M]+ |
| 14 | P1 | FP: 445 |
| 15 | P1 | FP: 445 |
| 16 | P1 | EP: 549 [M]+ |
| 17 | P1 | FP: 353 |
| 18 | P1 | EP: 443 |
| 19 | P2 | FP: 487 [M]+ |
| 20 | P2 | FP: 453 |
| 21 | P1 | FP: 487 [M]+ |
| 22 | P1 | FP: 487 [M]+ |
| 23 | P1 | FP: 473 |
| 24 | P2 | FP: 539 [M + Na]+ |
| 25 | P25 | EN: 501 |
| 26 | P2 | FP: 493 [M]+ |
| 27 | P2 | FP: 484 |
| 28 | P2 | FP: 527 |
| 29 | R1*P2 | FP: 489 |
| 30 | P2 | FP: 487 [M]+ |
| 31 | P2 | FP: 501 |
| 32 | R1*P2 | FP: 545 [M]+ |
| 33 | P33 | FP: 473 |
| 34 | P1 | FP: 469 |
| 35 | P1 | EP: 444 [M]+ |
| 36 | P1 | EP: 445 |
| 37 | P1 | EP: 445 |
| 38 | P2 | EP: 517 |
| 39 | P25 | FP: 503 |
| 40 | P1 | FP: 549 |
| 41 | R1*P2 | FP: 457 |
| 42 | P2 | FP: 517, 519 |
| 43 | P2 | FP: 493 |
| 44 | P2 | FP: 453 |
| 45 | P2 | FP: 484 |
| 46 | P2 | FP: 517, 519 |
| 47 | R1*P2 | FP: 465 |
| 48 | P5 | FP: 489 |
| 49 | P4 | FP: 459 |
| 50 | P1 | FP: 501 |
| 51 | P1 | FP: 461 |
| 52 | P1 | FP: 433 |
| 53 | P1 | FP: 501 |
| 54 | P1 | FP: 500 |
| 55 | P2 | FP: 530 |
| 56 | P1 | EP: 468 |
| 57 | P1 | FP: 509 |
| 58 | P1 | FP: 527 |
| 59 | R1*P2 | EP: 459 |
| 60 | R1*P2 | EP: 465 |

TABLE 47

| Pre | Syn | Dat |
|---|---|---|
| 61 | R1*P2 | EP: 473 |
| 62 | R1*P2 | EP: 473 |
| 63 | R1*P2 | EP: 493 |
| 64 | R1*P2 | EP: 499 |
| 65 | R1*P2 | EP: 499 |
| 66 | R1*P2 | EP: 504 |
| 67 | R1*P2 | EP: 535 |
| 68 | R1*P2 | EP: 551 |
| 69 | R1*P2 | EP: 552 |

TABLE 47-continued

| Pre | Syn | Dat |
|---|---|---|
| 70 | R1*P2 | EP: 565 |
| 71 | R1*P2 | EP: 552 |
| 72 | P1 | EP: 457 |
| 73 | P1 | EP: 457 |
| 74 | P1 | EP: 457 |
| 75 | P1 | EP: 501 |
| 76 | P1 | EP: 459 |
| 77 | P1 | EP: 461 |
| 78 | P1 | EP: 461 |
| 79 | P1 | EP: 477 |
| 80 | P1 | EP: 477 |
| 81 | P1 | EP: 477 |
| 82 | P1 | EP: 521 |
| 83 | P1 | EP: 521 |
| 84 | P1 | EP: 458 |
| 85 | P1 | EP: 486 |
| 86 | P1 | EP: 488 |
| 87 | P1 | EP: 488 |
| 88 | P1 | EP: 488 |
| 89 | P1 | EP: 519 |
| 90 | P1 | EP: 521 |
| 91 | P1 | EP: 521 |
| 92 | P1 | EP: 536 |
| 93 | P1 | EP: 522 |
| 94 | P1 | EP: 489 |
| 95 | P1 | EP: 445 |
| 96 | P1 | EP: 433 |
| 97 | P1 | EP: 434 |
| 98 | P1 | EP: 450 |
| 99 | P1 | EP: 449 |
| 100 | P1 | EP: 449 |
| 101 | P1 | EP: 447 |
| 102 | P1 | EP: 483 |
| 103 | P1 | EP: 499 |
| 104 | P1 | EP: 494 |
| 105 | P1 | EP: 457 |
| 106 | P1 | EP: 471 |
| 107 | P1 | EP: 475 |
| 108 | P1 | EP: 535 |
| 109 | P1 | EP: 528 |
| 110 | P1 | EP: 535 |
| 111 | P1 | EP: 447 |
| 112 | P1 | EP: 463 |
| 113 | P1 | EP: 458 |
| 114 | R1*P2 | EP: 489 |
| 115 | R1*P2 | EP: 464 |
| 116 | R1*P2 | EP: 439 |
| 117 | P1 | EP: 423 |
| 118 | P1 | EP: 446 |
| 119 | P1 | FP: 522 |
| 120 | P1 | FP: 566 |
| 121 | P1 | FP: 593 |
| 122 | P1 | EP: 468 |

TABLE 48

| Pre | Dat |
|---|---|
| 1 | NMR1: 2.31(3H, s), 2.42(3H, s), 3.71(3H, s), 4.05-4.32(4H, m), 6.72(1H, d, J = 8.1 Hz), 6.78(2H, d, J = 8.2 Hz), 6.91(2H, d, J = 8.1 Hz), 7.13(1H, t, J = 8.1 Hz), 7.38-7.48 (3H, m), 7.54(2H, d, J = 7.7 Hz), 8.33(1H, brs) |
| 2 | NMR1: 2.31(3H, s), 3.71(3H, s), 4.1(2H, d, J = 4.0 Hz), 4.17(1H, d, J = 16 Hz), 4.27(1H, d, J = 16 Hz), 6.76-6.8(3H, m), 6.93(2H, d, J = 8.0 Hz), 7.15(1H, t, J = 8.0 Hz), 7.43-7.48(3H, m), 7.72-7.76(2H, m), 8.35(1H, t, J = 6.0 Hz) |
| 3 | NMR1: 2.32(3H, s), 3.70(3H, s), 4.02(1H, d, J = 15.4 Hz), 4.07-4.14(2H, m), 4.25(1H, d, J = 15.3 Hz), 6.72(1H, d, J = 7.9 Hz), 6.78(2H, d, J = 8.6 Hz), 6.89-6.92(4H, m), 7.13(1H, t, J = 8.0 Hz), 7.43(1H, d, J = 8.0 Hz), 7.47(2H, d, J = 8.7 Hz), 8.31(1H, t, J = 5.8 Hz), 10.58(1H, s) |
| 4 | NMR1: 2.28(3H, s), 2.42(3H, s), 4.02-4.04(2H, m), 4.08(1H, d, J = 15.5 Hz), 4.26(1H, d, J = 15.4 Hz), 6.61(2H, d, J = 8.5 Hz), 6.72(1H, d, J = 7.1 Hz), 6.78(2H, d, J = 8.6 Hz), 7.13(1H, t, J = 8.0 Hz), 7.40-7.42(3H, m), 7.54(2H, d, J = 8.3 Hz), 8.26(1H, t, J = 5.8 Hz), 9.25(1H, s) |
| 5 | NMR1: 2.31(3H, s), 3.71(3H, s), 4.08-4.12(3H, m), 4.28(1H, d, J = 15.4 Hz), 4.62(2H, d, J = 5.7 Hz), 5.47(1H, t, J = 5.7 Hz), 6.72(1H, d, J = 7.8 Hz), 6.78(2H, d, J = 8.7 Hz), 6.91(2H, d, J = 8.5 Hz), 7.13(1H, t, J = 8.0 Hz), 7.45(1H, d, J = 7.9 Hz), 7.53(2H, d, J = 8.4 Hz), 7.62(2H, d, J = 8.3 Hz), 8.34(1H, t, J = 5.8 Hz) |
| 6 | NMR1: 2.29(3H, s), 2.42(3H, s), 4.1-4.16(3H, m), 4.32(1H, d, J = 8.0 Hz), 6.74(1H, d, J = 4.0 Hz), 6.98(2H, d, J = 3.5 Hz), 7.15 (1H, t, J = 4.0 Hz), 7.41-7.46(3H, m), 7.54(2H, d, J = 4.1 Hz), 8.06(2H, d, J = 3.5 Hz), 8.54(1H, t, J = 3 Hz) |
| 15 | NMR1: 2.29(3H, s), 2.42(3H, s), 4.19(1H, d, J = 15.7 Hz), 4.25-4.27(2H, m), 4.37(1H, d, J = 15.7 Hz), 6.76(1H, d, J = 7.6 Hz), 6.96(1H, d, J = 5.2 Hz), 7.15(1H, t, J = 8.1 Hz), 7.42(1H, d, J = 8.1 Hz), 7.46(1H, d, J = 8.3 Hz), 7.56(2H, d, J = 8.3 Hz), 8.61-8.66(2H, m), 9.04(1H, d, J = 1.4 Hz) |
| 19 | NMR1: 2.28(3H, s), 2.41(3H, s), 3.7(2H, s), 3.73(3H, s), 4.01(2H, d, J = 5.7 Hz), 4.46(2H, s), 6.85(2H, d, J = 8.7 Hz), 7.03(2H, d, J = 8.7 Hz), 7.12-7.14(1H, m), 7.2(1H, d, J = 6.8 Hz), 7.36-7.37(3H, m), 7.73(2H, d, J = 8.2 Hz), 8.08(1H, t, J = 5.8 Hz) |

TABLE 49

| Ex | Syn | Dat |
|---|---|---|
| 1 | 1 | EP: 487 |
| 2 | 2 | EP: 486 |
| 3 | 3 | EP: 567 [M + Na]+ |
| 4 | 4 | FP: 564 |
| 5 | 1 | EP: 539 [M + Na]+ |
| 6 | 1 | EP: 501 |
| 7 | 1 | FP: 487 |
| 8 | P1*1 | FN: 488 |
| 9 | P1*1 | FN: 504 |
| 10 | 2 | FP: 486 |
| 11 | P1*1 | FP: 501 |
| 12 | P1*1 | FP: 501 |
| 13 | P1*1 | FP: 501 |
| 14 | P1*1 | FP: 515 |
| 15 | P2*1 | EP: 501 |
| 16 | 3*1 | EN: 514 |
| 17 | P1 | EN: 499 |
| 18 | P1*1 | EN: 515 |
| 19 | P1*1 | FP: 501 |
| 20 | 4 | FP: 564 |
| 21 | 1 | FP: 497 |
| 22 | 1 | EN: 539 |
| 23 | 1 | FP: 515 |
| 24 | P1 | FP: 501 |
| 25 | P1 | EP: 508 |
| 26 | P1 | FP: 509 |
| 27 | P1 | EP: 516 |
| 28 | 4 | FP: 594 |
| 29 | P2 | FP: 512 |
| 30 | P2 | FP: 555 |
| 31 | P1 | FP: 529 |
| 32 | P1 | EP: 520 |
| 33 | P1 | EP: 510 |
| 34 | P1 | FP: 528 |
| 35 | P1 | EP: 526 |
| 36 | P1 | EP: 517 |
| 37 | P2*1 | FP: 506 |
| 38 | R1*P2*1 | FP: 503 |
| 39 | P2*1 | FP: 533 |
| 40 | P2*1 | FP: 501 |
| 41 | P2*1 | FP: 487 |
| 42 | P2*1 | FP: 501 |
| 43 | R1*P2*1 | FP: 502 |
| 44 | P2*1 | EP: 557 |
| 45 | R1*P2*1 | FP: 513 |
| 46 | P2*1 | EN: 486 |
| 47 | P1*1 | EP: 488 |
| 48 | P1*1 | EP: 493 |
| 49 | P1*1 | EP: 493 |
| 50 | P1*1 | EP: 513 |
| 51 | P1*1 | EN: 513 |
| 52 | P1*1 | EP: 513 |
| 53 | P1*1 | EN: 513 |
| 54 | 4 | EP: 608 |
| 55 | 2 | FP: 530 |
| 56 | 2 | EP: 557 |
| 57 | 2 | EP: 530 |
| 58 | 2 | FP: 557 |
| 59 | P2*1 | FP: 494 |
| 60 | P1 | FP: 487 |

TABLE 50

| Ex | Syn | Dat |
|---|---|---|
| 61 | P1*1 | EP537 |
| 62 | P1*1 | EP: 531 |
| 63 | P1*1 | FP: 521 |
| 64 | P1*1 | EP: 528 |
| 65 | P1*1 | FP: 571 |
| 66 | P1*1 | EP: 488 |
| 67 | P1*1 | EP: 494 |
| 68 | P1 | EP: 540 |
| 69 | P1 | EP: 555 |
| 70 | P2*1 | EN: 501 [M]− |
| 71 | P2*1 | FP: 488 |
| 72 | P1*1 | FP: 505 |
| 73 | P1*1 | FP: 529 |
| 74 | P1*1 | FP: 527 |
| 75 | P1*1 | EN: 529 |
| 76 | P1*1 | EN: 488 |
| 77 | P1 | FP: 527 |
| 78 | P1*1 | EP: 567 |
| 79 | P1*1 | EN: 531 |
| 80 | 2*1 | EP: 544 |
| 81 | P1*1 | EP: 505 |
| 82 | P1*1 | EP: 569 |
| 83 | P1*1 | EP: 535 |
| 84 | P1*1 | FP: 529 |
| 85 | P2*1 | FP: 505 |

TABLE 50-continued

| Ex | Syn | Dat |
|---|---|---|
| 86 | P1*1 | EP: 527 |
| 87 | P2*1 | FP: 505 |
| 88 | P1*1 | EP: 505 |
| 89 | 2 | FP: 560 |
| 90 | 2 | EP: 560 |
| 91 | 2 | EP: 560 |
| 92 | 2 | EP: 560 |
| 93 | P1*1 | EP: 505 |
| 94 | P1*1 | EP: 505 |
| 95 | P1*1 | FP: 547 |
| 96 | P1*1 | FP: 513 |
| 97 | P1 | FP: 542 |
| 98 | P1 | EP: 553 |
| 99 | P1 | FP: 542 |
| 100 | P1 | FP: 556 |
| 101 | 4 | FP: 578 |
| 102 | 4 | FP: 592 |
| 103 | 4 | FP: 608 |
| 104 | P1 | FN: 552 [M]− |
| 105 | P1*1*4 | FP: 575 |
| 106 | P1*1*4 | FP: 578 |
| 107 | P1*1*4 | FP: 584 |
| 108 | P1*1*4 | FP: 618 |
| 109 | P1 | EP: 538 |
| 110 | P1 | FP: 581 |
| 111 | P1 | FP: 543 |
| 112 | P1 | EP: 554 |
| 113 | P1 | FP: 596 |
| 114 | P1*1 | EP: 478 |
| 115 | P1*1 | EP: 477 |
| 116 | P1*1 | EP: 493 |
| 117 | P1*1 | EP: 527 |
| 118 | P1*1 | EP: 529 |
| 119 | 3*1 | EP: 531 |
| 120 | 3*1 | EP: 531 |

TABLE 51

| Ex | Syn | Dat |
|---|---|---|
| 121 | P1*1 | EP: 489 |
| 122 | P1*1 | EP: 545 |
| 123 | R1*P2*1 | EP: 439 |
| 124 | R1*P2*1 | EP: 471 |
| 125 | R1*P2*1 | EP: 471 |
| 126 | R1*P2*1 | EP: 471 |
| 127 | R1*P2*1 | EP: 487 |
| 128 | R1*P2*1 | EP: 487 |
| 129 | R1*P2*1 | EP: 487 |
| 130 | R1*P2*1 | EP: 487 |
| 131 | R1*P2*1 | EP: 487 |
| 132 | R1*P2*1 | EP: 531 |
| 133 | R1*P2*1 | EP: 531 |
| 134 | R1*P2*1 | EP: 531 |
| 135 | R1*P2*1 | EP: 491 |
| 136 | R1*P2*1 | EP: 517 |
| 137 | R1*P2*1 | EP: 467 |
| 138 | R1*P2*1 | EP: 469 |
| 139 | R1*P2*1 | EP: 483 |
| 140 | R1*P2*1 | EP: 483 |
| 141 | R1*P2*1 | EP: 483 |
| 142 | R1*P2*1 | EP: 521 |
| 143 | R1*P2*1 | EP: 497 |
| 144 | R1*P2*1 | EP: 483 |
| 145 | R1*P2*1 | EP: 498 |
| 146 | R1*P2*1 | EP: 518 |
| 147 | R1*P2*1 | EP: 475 |
| 148 | R1*P2*1 | EP: 531 |
| 149 | R1*P2*1 | EP: 499 |
| 150 | R1*P2*1 | EP: 496 |
| 151 | R1*P2*1 | EP: 479 |
| 152 | R1*P2*1 | EP: 493 |
| 153 | R1*P2*1 | EP: 522 |
| 154 | R1*P2*1 | EP: 478 |
| 155 | R1*P2*1 | EP: 478 |

TABLE 51-continued

| Ex | Syn | Dat |
|---|---|---|
| 156 | R1*P2*1 | EP: 453 |
| 157 | R1*P2*1 | EP: 467 |
| 158 | R1*P2*1 | EP: 467 |
| 159 | R1*P2*1 | EP: 457 |
| 160 | R1*P2*1 | EP: 457 |
| 161 | R1*P2*1 | EP: 473 |
| 162 | R1*P2*1 | EP: 473 |
| 163 | R1*P2*1 | EP: 517 |
| 164 | R1*P2*1 | EP: 469 |
| 165 | R1*P2*1 | EP: 469 |
| 166 | R1*P2*1 | EP: 455 |
| 167 | R1*P2*1 | EP: 483 |
| 168 | R1*P2*1 | EP: 469 |
| 169 | R1*P2*1 | EP: 469 |
| 170 | R1*P2*1 | EP: 497 |
| 171 | R1*P2*1 | EP: 464 |
| 172 | R1*P2*1 | EP: 485 |
| 173 | R1*P2*1 | EP: 485 |
| 174 | R1*P2*1 | EP: 482 |
| 175 | R1*P2*1 | EP: 496 |
| 176 | R1*P2*1 | EP: 496 |
| 177 | R1*P2*1 | EP: 482 |
| 178 | R1*P2*1 | EP: 481 |
| 179 | R1*P2*1 | EP: 522 |
| 180 | R1*P2*1 | EP: 524 |

TABLE 52

| Ex | Syn | Dat |
|---|---|---|
| 181 | R1*P2*1 | EP: 437 |
| 182 | R1*P2*1 | EP: 465 |
| 183 | R1*P2*1 | EP;: 473 |
| 184 | R1*P2*1 | EP: 477 |
| 185 | R1*P2*1 | EP: 479 |
| 186 | R1*P2*1 | EP: 479 |
| 187 | R1*P2*1 | EP: 479 |
| 188 | R1*P2*1 | EP: 487 |
| 189 | R1*P2*1 | EP: 493 |
| 190 | R1*P2*1 | EP: 503 |
| 191 | R1*P2*1 | EP: 503 |
| 192 | R1*P2*1 | EP: 474 |
| 193 | R1*P2*1 | EP: 515 |
| 194 | R1*P2*1 | EP: 517 |
| 195 | R1*P2*1 | EP: 517 |
| 196 | R1*P2*1 | EP: 523 |
| 197 | R1*P2*1 | EP: 527 |
| 198 | R1*P2*1 | EP: 529 |
| 199 | R1*P2*1 | EP: 541 |
| 200 | R1*P2*1 | EP: 544 |
| 201 | R1*P2*1 | EP: 545 |
| 202 | R1*P2*1 | EP: 545 |
| 203 | R1*P2*1 | EP: 549 |
| 204 | R1*P2*1 | EP: 551 |
| 205 | R1*P2*1 | EP: 555 |
| 206 | R1*P2*1 | EP: 559 |
| 207 | R1*P2*1 | EP: 559 |
| 208 | R1*P2*1 | EP: 559 |
| 209 | R1*P2*1 | EP: 565 |
| 210 | R1*P2*1 | EP: 565 |
| 211 | R1*P2*1 | EP: 565 |
| 212 | R1*P2*1 | EP: 579 |
| 213 | R1*P2*1 | EP: 589 |
| 214 | R1*P2*1 | EP: 601 |
| 215 | R1*P2*1 | EP: 566 |
| 216 | P1*1 | EP: 513 |
| 217 | P1*1 | EP: 547 |
| 218 | P1*1 | EP: 507 |
| 219 | P1*1 | EP: 511 |
| 220 | P1*1 | EP: 513 |
| 221 | P1*1 | EP: 509 |
| 222 | P1*1 | EP: 539 |
| 223 | P1*1 | EP: 551 |
| 224 | P1*1 | EP: 585 |
| 225 | P1*1 | EP: 545 |

TABLE 52-continued

| Ex | Syn | Dat |
|---|---|---|
| 226 | P1*1 | EP: 549 |
| 227 | P1*1 | EP: 551 |
| 228 | P1*1 | EP: 547 |
| 229 | P1*1 | EP: 575 |

TABLE 52-continued

| Ex | Syn | Dat |
|---|---|---|
| 230 | 230 | EP: 527 |
| 231 | 231 | EP: 511 |

TABLE 53

| Ex | Dat |
|---|---|
| 1 | NMR1: 2.31(3H, s), 2.42(3H, s), 4.12(1H, d, J = 15.4 Hz), 4.18-4.19(2H, m), 4.33(1H, d, J = 15.4 Hz), 6.73(1H, d, J = 7.8 Hz), 7.06(2H, d, J = 8.2 Hz), 7.15(1H, t, J = 8.0 Hz), 7.42(2H, d, J = 8.2 Hz), 7.45(1H, d, J = 8.2 Hz), 7.55(2H, d, J = 8.3 Hz), 7.79(2H, d, J = 8.2 Hz), 8.50(1H, t, J = 6.0 Hz), 12.74(1H, brs) |
| 2 | NMR1: 2.31(3H, s), 2.42(3H, s), 4.12-4.15(4H, m), 6.75(1H, d, J = 7.7 Hz), 7.05(2H, d, J = 8.2 Hz), 7.14(1H, t, J = 8.0 Hz), 7.3(1H, brs), 7.41(2H, d, J = 8.2 Hz), 7.46(1H, d, J = 7.8 Hz), 7.55(2H, d, J = 8.3 Hz), 7.73(2H, d, J = 8.2 Hz), 7.9(1H, brs), 8.47(1H, t, J = 5.9 Hz) |
| 4 | NMR1: 2.30(3H, s), 2.42(3H, s), 3.36(3H, s), 4.13(1H, d, J = 15.6 Hz), 4.23(2H, d, J = 5.9 Hz), 4.30(1H, d, J = 15.6 Hz), 6.74(1H, d, J = 8.0 Hz), 7.12(1H, t, J = 8.0 Hz), 7.2(1H, d, J = 7.7 Hz), 7.36(1H, d, J = 7.6 Hz), 7.39-7.44(3H, m), 7.54(2H, d, J = 8.3 Hz), 7.72(1H, s), 7.77(1H, d, J = 7.8 Hz), 8.5(1H, t, J = 5.9 Hz), 12.11(1H, brs) |
| 5 | NMR1: 2.32(3H, s), 2.41(3H, s), 4.03-4.04(4H, m), 4.26(1H, d, J = 15.4 Hz), 4.37(1H, d, J = 3.8 Hz), 6.65(2H, d, J = 8.7 Hz), 6.72(1H, d, J = 7.8 Hz), 6.83(2H, d, J = 8.5 Hz), 7.12(1H, t, J = 8.0 Hz), 7.40-7.42(3H, m), 7.54(2H, d, J = 8.3 Hz), 8.36(1H, t, J = 5.7 Hz) |
| 7 | NMR1: 2.30(3H, s), 2.41(3H, s), 4.13(1H, d, J = 15.6 Hz), 4.23(2H, d, J = 5.9 Hz), 4.29(1H, d, J = 15.6 Hz), 6.74(1H, d, J = 7.2 Hz), 7.11(1H, t, J = 8.0 Hz), 7.20(1H, d, J = 7.8 Hz), 7.35(1H, t, J = 7.7 Hz), 7.39-7.40(3H, m), 7.54(2H, d, J = 8.4 Hz), 7.75(1H, s), 7.78(1H, d, J = 7.8 Hz), 8.49(1H, t, J = 5.9 Hz), 12.93(1H, brs) |
| 9 | NMR1: 2.30(1H, s), 4.23-4.31(4H, m), 6.82(2H, d, J = 7.8 Hz), 7.14(1H, t, J = 8.0 Hz), 7.22(1H, d, J = 7.7 Hz), 7.36(1H, t, J = 7.6 Hz), 7.44(1H, d, J = 7.8 Hz), 7.67(4H, brs), 7.75(1H, s), 7.79(1H, d, J = 7.8 Hz), 8.51(1H, t, J = 5.9 Hz), 12.94(1H, brs) |
| 16 | NMR1: 2.31(3H, s), 2.42(3H, s), 4.11-4.15(3H, m), 4.29(1H, d, J = 15.6 Hz), 4.61(2H, s), 6.55(1H, d, J = 7.6 Hz), 6.68(1H, s), 6.72-6.75(2H, m), 7.11-7.15(2H, m), 7.4-7.44(3H, m), 7.55(2H, d, J = 8.2 Hz), 8.4(1H, t, J = 5.9 Hz), 12.97(1H, brs) |

TABLE 54

| Ex | Dat |
|---|---|
| 20 | NMR1: 2.30(3H, s), 2.42(3H, s), 3.37(3H, s), 4.14(1H, d, J = 15.6 Hz), 4.25(2H, t, J = 5.7 Hz), 4.32(1H, d, J = 15.6 Hz), 6.75(1H, d, J = 7.2 Hz), 7.11(2H, d, J = 8.3 Hz), 7.16(1H, d, J = 8.1 Hz), 7.42(2H, d, J = 8.3 Hz), 7.46(1H, d, J = 7.2 Hz), 7.55(2H, d, J = 8.3 Hz), 7.81(2H, d, J = 8.3 Hz), 8.52(1H, t, J = 6.0 Hz), 12.07(1H, brs) |
| 21 | NMR1: 2.29(3H, s), 4.24(2H, d, J = 5.6 Hz), 4.30(2H, d, J = 6.8 Hz), 6.83(1H, d, J = 8.0 Hz), 7.14(1H, t, J = 8.0 Hz), 7.19-7.29(1H, m), 7.37(1H, t, J = 8.0 Hz), 7.46(1H, d, J = 8.0 Hz), 7.70-7.90(4H, m), 8.03-8.15(2H, m), 8.46-8.58(1H, m), 12.94(1H, brs) |
| 22 | NMR1: 2.29(3H, s), 4.23(2H, d, J = 5.6 Hz), 4.30(2H, d, J = 4.0 Hz), 6.84(1H, d, J = 8.0 Hz), 7.15(1H, t, J = 8.0 Hz), 7.22(1H, d, J = 7.6 Hz), 7.36(1H, t, J = 8.0 Hz), 7.46(1H, d, J = 8.0 Hz), 7.71-7.82(2H, m), 7.88(2H, d, J = 8.4 Hz), 7.98(2H, d, J = 8.4 Hz), 8.47-8.58(1H, m) |
| 24 | NMR1: 2.30(3H, s), 2.42(3H, s), 3.83(3H, s), 4.09-4.35(4H, m), 6.73(1H, d, J = 8.0 Hz), 7.1(2H, d, J = 8.0 Hz), 7.15(1H, t, J = 8.2 Hz), 7.41-7.46(3H, m), 7.55(2H, d, J = 8.0 Hz), 7.81(2H, d, J = 8.0 Hz), 8.53(1H, t, J = 5.9 Hz) |
| 26 | NMR1: 2.31(3H, s), 2.42(3H, s), 4.11-4.33(4H, m), 6.53(1H, t, J = 2.0 Hz), 6.75(1H, d, J = 7.8 Hz), 7.11(2H, d, J = 8.5 Hz), 7.16(1H, d, J = 8.0 Hz), 7.41-7.46(3H, m), 7.56(2H, d, J = 8.2 Hz), 7.68-7.72(3H, m), 8.44-8.46(2H, m) |
| 28 | NMR1: 2.30(3H, s), 2.42(3H, s), 3.33(3H, s), 4.15(1H, d, J = 15.8 Hz), 4.25(2H, d, J = 5.8 Hz), 4.32(1H, d, J = 15.7 Hz), 6.64(1H, d, J = 8.0 Hz), 6.76(1H, d, J = 8.0 Hz), 6.95(1H, s), 7.14(1H, t, J = 8.0 Hz), 7.41-7.47(4H, m), 7.55(2H, d, J = 8.2 Hz), 8.52(1H, t, J = 6.0 Hz), 11.29(1H, brs) |
| 37 | NMR1: 2.40(3H, s), 4.14(1H, brs), 4.25(2H, d, J = 6.0 Hz), 4.50(1H, brs), 7.22-7.43(6H, m), 7.54-7.68(3H, m), 7.73-7.83(2H, m), 8.48-8.58(1H, m), 12.95(1H, brs) |
| 38 | NMR1: 2.39(3H, s), 3.71(3H, s), 4.23(2H, d, J = 6.0 Hz), 4.32(2H, s), 7.05(1H, t, J = 8.0 Hz), 7.11(1H, dd, J = 8.0 Hz, 2.0 Hz), 7.26(1H, d, J = 7.6 Hz), 7.32-7.41(3H, m), 7.46(1H, dd, J = 8.0 Hz, 2.0 Hz), 7.66(2H, d, J = 8.4 Hz), 7.75(1H, brs), 7.79(1H, d, J = 8.0 Hz), 8.45-8.58(1H, m), 12.93(1H, brs) |

TABLE 55

| Ex | Dat |
|---|---|
| 39 | NMR1: 2.33(3H, s), 2.41(3H, s), 4.07-4.35(4H, m), 6.77(1H, d, J = 7.6 Hz), 7.04(1H, t, J = 8.0 Hz), 7.19(1H, d, J = 8.0 Hz), 7.35(1H, t, J = 8.0 Hz), 7.40(2H, d, J = 8.0 Hz), 7.53(2H, d, J = 8.0 Hz), 7.58(1H, d, J = 8.0 Hz), 7.74(1H, brs), 7.78(1H, d, J = 8.0 Hz), 8.41-8.56(1H, m), 12.93(1H, brs) |
| 40 | NMR1: 1.16(3H, t, J = 8.0 Hz), 2.41(3H, s), 2.82(2H, d, J = 8.0 Hz), 4.14-4.29(4H, m), 6.76(1H, dd, J = 8.0 Hz, 0.8 Hz), 7.11(1H, t, J = 8.0 Hz), 7.21(1H, d, J = 8.0 Hz), 7.33-7.44(4H, m), 7.56(2H, d, J = 8.0 Hz), 7.72-7.82(2H, m), 8.46-8.55(1H, m), 12.93(1H, brs) |
| 42 | NMR1: 1.21(3H, t, J = 7.6 Hz), 2.28(3H, s), 2.71(2H, q, J = 7.6 Hz), 4.07-4.35(4H, m), 6.75(1H, d, J = 8.0 Hz), 7.11(1H, t, J = 8.0 Hz), 7.19(1H, d, J = 8.0 Hz), 7.35(1H, t, J = 8.0 Hz), 7.39-7.47(3H, m), 7.56(2H, d, J = 8.0 Hz), 7.74(1H, brs), 7.78(1H, d, J = 8.0 Hz), 8.44-8.55(1H, m), 12.93(1H, brs) |
| 49 | NMR1: 2.30(3H, s), 2.41(3H, s), 4.11(1H, d, J = 15.9 Hz), 4.26(1H, d, J = 15.9 Hz), 4.32 (2H, d, J = 5.8 Hz), 6.75(1H, d, J = 7.1 Hz), 7.10(1H, t, J = 7.9 Hz), 7.17(1H, d, J = 1.0 Hz), 7.38-7.42(3H, m), 7.54(2H, d, J = 8.3 Hz), 8.05(1H, d, J = 1.4 Hz), 8.57(1H, t, J = 5.8 Hz), 12.50-12.70(1H, br) |
| 50 | NMR1: 2.30(3H, s), 2.42(3H, s), 4.07-4.37(4H, m), 6.47(1H, d, J = 16.0 Hz), 6.75(1H, d, J = 8.0 Hz), 7.01(1H, d, J = 8.0 Hz), 7.13(1H, t, J = 8.0 Hz), 7.27(1H, t, J = 8.0 Hz), 7.34-7.59(8H, m), 8.39-8.49(1H, m), 12.42(1H, brs) |
| 51 | NMR1: 2.31(3H, s), 2.41(3H, s), 2.47(2H, t, J = 8.0 Hz), 2.74(2H, t, J = 8.0 Hz), 4.05-4.34(4H, m), 6.74(1H, d, J = 8.0 Hz), 6.78(1H, d, J = 8.0 Hz), 6.92(1H, s), 7.05(1H, d, J = 8.0 Hz), 7.13(2H, t, J = 8.0 Hz), 7.36-7.47(3H, m), 7.55(2H, d, J = 8.0 Hz), 8.33-8.43(1H, m), 12.12(1H, s) |
| 74 | NMR1: 1.16(3H, t, J = 7.6 Hz), 2.41(3H, s), 2.84(2H, q, J = 7.6 Hz), 4.11-4.31(4H, m), 6.47(1H, d, J = 16.0 Hz), 6.76(1H, d, J = 8.0 Hz), 7.02(1H, d, J = 8.0 Hz), 7.12(1H, t, J = 8.0 Hz), 7.28(1H, t, J = 8.0 Hz), 7.36-7.46(4H, m), 7.51(1H, d, J = 16.0 Hz), 7.52(1H, d, J = 8.0 Hz), 7.57(2H, d, J = 8.0 Hz), 8.38-8.52(1H, m), 12.40(1H, brs) |

TABLE 56

| Ex | Dat |
|---|---|
| 78 | NMR1: 2.30(3H, s), 4.21(2H, d, J = 5.6 Hz), 4.31(2H, s), 6.46(1H, d, J = 16.0 Hz), 6.84(1H, d, J = 8.0 Hz), 7.04(1H, d, J = 8.0 Hz), 7.17(1H, t, J = 8.0 Hz), 7.29(1H, t, J = 8.0 Hz), 7.38(1H, s), 7.43-7.57(3H, m), 7.89(2H, d, J = 8.4 Hz), 7.99(2H, d, J = 8.4 Hz), 8.44-8.50(1H, m) |
| 79 | NMR1: 2.31(3H, s), 4.17-4.35(4H, m), 6.46(1H, d, J = 16.0 Hz), 6.82(1H, d, J = 8.0 Hz), 7.03(1H, d, J = 8.0 Hz), 7.16(1H, t, J = 8.0 Hz), 7.28(1H, t, J = 8.0 Hz), 7.38(1H, s), 7.43-7.56(3H, m), 7.68(4H, s), 8.41-8.51(1H, m) |
| 82 | NMR1: 2.32(3H, s), 2.47(2H, t, J = 8.0 Hz), 2.74(2H, t, J = 8.0 Hz), 4.15(2H, d, J = 5.6 Hz), 4.24-4.36(2H, m), 6.77-6.87(2H, m), 6.93(1H, s), 7.06(1H, d, J = 8.0 Hz), 7.11-7.21(2H, m), 7.47(2H, d, J = 8.0 Hz), 7.90(2H, d, J = 8.0 Hz), 7.99(2H, d, J = 8.0 Hz), 8.36-8.45(1H, m), 12.12(1H, s) |
| 85 | NMR1: 2.25(3H, s), 2.40(3H, s), 4.17-4.44(4H, m), 7.05(1H, d, J = 8.0 Hz), 7.11-7.18(2H, m), 7.23(1H, d, J = 8.0 Hz), 7.31(1H, d, J = 12.0 Hz), 7.36(1H, t, J = 8.0 Hz), 7.42(1H, d, J = 8.0 Hz), 7.49(1H, t, J = 8.0 Hz), 7.74(1H, brs), 7.75(1H, s), 7.79(1H, d, J = 8.0 Hz), 8.46-8.55(1H, m), 12.93(1H, brs) |
| 114 | NMR1: 2.29(3H, s), 2.41(3H, s), 4.16-4.34(4H, m), 6.77(1H, d, J = 7.6 Hz), 7.12(1H, t, J = 8.0 Hz), 7.39-7.42(3H, m), 7.53(2H, d, J = 8.4 Hz), 8.63(1H, s), 8.67(1H, t, J = 6.0 Hz) |
| 116 | NMR1: 2.29(3H, s), 2.45(3H, s), 4.09-4.29(4H, m), 6.77(1H, d, J = 8.0 Hz), 7.12(1H, t, J = 7.6 Hz), 7.31(1H, s), 7.34-7.49(3H, m), 7.50(1H, s), 7.56(2H, d, J = 7.6 Hz), 8.42(1H, t, J = 6.0 Hz) |
| 119 | NMR1: 1.44(3H, d, J = 6.8 Hz), 2.31(3H, s), 2.42(3H, s), 4.10-4.30(4H, m), 4.65-4.67(1H, m), 6.51(1H, d, J = 7.6 Hz), 6.61-6.67(2H, m), 6.74(1H, d, J = 8.0 Hz), 7.08-7.15(2H, m), 7.39-7.44(3H, m), 7.55(2H, d, J = 8.0 Hz), 8.38(1H, t, J = 5.2 Hz) |
| 120 | NMR1: 1.45(3H, d, J = 6.8 Hz), 2.31(3H, s), 2.42(3H, s), 4.11-4.30(4H, m), 4.66-4.68(1H, m), 6.52(1H, d, J = 7.2 Hz), 6.61-6.68(2H, m), 6.75(1H, d, J = 8.0 Hz), 7.08-7.15(2H, m), 7.39-7.44(3H, m), 7.55(1H, d, J = 8.0 Hz), 8.38(1H, t, J = 5.6 Hz) |

Industrial Applicability

The sulfonamide compound of the present invention or a pharmaceutically acceptable salt thereof has a potent EP1 receptor antagonistic activity, and thus it is useful as a remedy for diseases associated with an EP1 receptor, in particular for a lower urinary tract symptom.

SEQUENCE LISTING FREE TEXT

Under the number title <223> in the following sequence listing, description on "Artificial Sequence" is given. Specifically, the amino acid sequence of SEQ ID NO. 1 in the sequence listing is an artificially synthesized signal peptide sequence. Furthermore, the amino acid sequence of SEQ ID NO. 2 in the sequence listing is an artificially synthesized FLAG sequence.

$N^2$-(3-chloro-2-methylphenyl)-$N^2$-[(4-methylphenyl)sulfonyl]-N-[4-(1H-pyrazol-1-yl)benzyl]glycinamide, 4-[({N-(3-chloro-2-methylphenyl)-N-[(4-methylphenyl)sulfonyl]glycyl}amino)-methyl]-2-methoxy-N-(methylsulfonyl)benzamide, $N^2$-(3-chloro-2-methylphenyl)-$N^2$-[(4-methylphenyl)sulfonyl]-N-[4-(2-oxopyrrolidin-1-yl)benzyl]glycinamide, 3-[({N-(2,3-dichlorophenyl)-N-[(4-methylphenyl)sulfonyl]glycyl}amino)-methyl]benzoic acid, 3-[({N-(3-chloro-2-methoxyphenyl)-N-[(4-methylphenyl)sulfonyl]glycyl}amino)-methyl]benzoic acid, 3-[({N-(3-bromo-2-methylphenyl)-N-[(4-methylphenyl)sulfonyl]glycyl}amino)-methyl]benzoic acid, 3-[({N-(3-chloro-2-ethylphenyl)-N-[(4-methylphenyl)sulfonyl]glycyl}amino)-methyl]benzoic acid,

The invention claimed is:

1. A compound or pharmaceutically acceptable salt thereof, which is selected from the group consisting of:

3-[({N-(3-chloro-2-methylphenyl)-N-[(4-methylphenyl)sulfonyl]glycyl}amino)-methyl]-N-(methylsulfonyl)benzamide, 3-[({N-(3-chloro-2-methylphenyl)-N-[(4-methylphenyl)sulfonyl]glycyl}amino)-methyl]benzoic acid, 3-[({N-(3-chloro-2-methylphenyl)-N-[(4-chlorophenyl)sulfonyl]glycyl}amino)-methyl]benzoic acid, 3-[({N-(3-chloro-2-methylphenyl)-N-[(4-methylphenyl)sulfonyl]glycyl}amino)-methyl]phenoxyacetic acid, 4-[({N-(3-chloro-2-methylphenyl)-N-[(4-methylphenyl)sulfonyl]glycyl}amino)-methyl]-N-(methylsulfonyl)benzamide, 3-[({N-(3-chloro-2-methylphenyl)-N-[(4-cyanophenyl)sulfonyl]glycyl}amino)-methyl]benzoic acid, 3-{[(N-(3-chloro-2-methylphenyl)-N-{[4-(trifluoromethyl)phenyl]sulfonyl}glycyl)-amino]methyl}benzoic acid, methyl 4-[({N-(3-chloro-2-methylphenyl)-N-[(4-methylphenyl)sulfonyl]glycyl}-amino)methyl]benzoate, 3-[({N-(3-chloro-2-methylphenyl)-N-[(4-ethylphenyl)sulfonyl]glycyl}amino)-methyl]benzoic acid, 5-[({N-(3-chloro-2-methylphenyl)-N-[(4-methylphenyl)sulfonyl]glycyl}amino)-methyl]thiophene-3-carboxylic acid, 3-[({N-(3-chloro-2-methylphenyl)-N-[(4-methylphenyl)sulfonyl]glycyl}amino)-methyl]cinnamic acid, 3-{3-[({N-(3-chloro-2-methylphenyl)-N-[(4-methylphenyl)sulfonyl]glycyl}amino)-methyl]phenyl}propionic acid, 4-[({N-(3-chloro-2-methylphenyl)-N-[(4-methylphenyl)sulfonyl]glycyl}amino)-methyl]-N-[(3-hydroxypropyl)sulfonyl]benzamide, 3-[({N-(3-chloro-2-methylphenyl)-N-[(4-methylphenyl)sulfonyl]glycyl}amino)-methyl]-N-(2-hydroxyethyl)benzamide, 4-[({N-(3-chloro-2-methylphenyl)-N-[(4-methylphenyl)sulfonyl]glycyl}amino)-methyl]-N-(2-hydroxyethyl)benzamide, 4-[({N-(3-chloro-2-methylphenyl)-N-[(4-methylphenyl)sulfonyl]glycyl}amino)-methyl]-N-[2-(dimethylamino)ethyl]benzamide, {3-[({N-(3-chloro-2-methylphenyl)-N-[(4-chlorophenyl)sulfonyl]glycyl}amino)-methyl]phenoxy}acetic acid,
[3-({[N-(3-chloro-2-methylphenyl)-N-{[4-(trifluoromethyl)phenyl]sulfonyl}glycyl]-amino}methyl)phenoxy]acetic acid,
$N^2$-(3-chloro-2-methylphenyl)-$N^2$-[(4-methylphenyl)sulfonyl]-N-[4-(2-oxopiperidin-1-yl)benzyl]glycinamide,
3-[({N-(3-chloro-2-methylphenyl)-N-[(4-methylphenyl)sulfonyl]glycyl}amino)-methyl]-4-fluorobenzoic acid,
3-{3-[({N-(3-chloro-2-ethylphenyl)-N-[(4-methylphenyl)sulfonyl]glycyl}amino)-methyl]phenyl}propanoic acid,
3-[({N-(3-chloro-2-ethylphenyl)-N-[(4-methylphenyl)sulfonyl]glycyl}amino)-methyl]cinnamic acid,
{3-[({N-(3-chloro-2-ethylphenyl)-N-[(4-methylphenyl)sulfonyl]glycyl}amino)-methyl]phenoxy}acetic acid,
$N^2$-(3-chloro-2-methylphenyl)-$N^2$-[(4-methylphenyl)sulfonyl]-N-{[5-(2-oxopyrrolidin-1-yl)pyridin-2-yl]methyl}glycinamide,
3-{[(N-(3-chloro-2-methylphenyl)-N-{[4-(trifluoromethyl)phenyl]sulfonyl}glycyl)-amino]methyl}cinnamic acid,
3-[({N-(3-chloro-2-methylphenyl)-N-[(4-chlorophenyl)sulfonyl]glycyl}amino)-methyl]cinnamic acid,
5-[({N-(3-chloro-2-methylphenyl)-N-[(4-methylphenyl)sulfonyl]glycyl}amino)-methyl]-2-fluorobenzoic acid,
3-(3-{[(N-(3-chloro-2-methylphenyl)-N-{[4-(trifluoromethyl)phenyl]sulfonyl}-glycyl)amino]methyl}phenyl)propionic acid,
3-{3-[({N-(3-chloro-2-methylphenyl)-N-[(4-chlorophenyl)sulfonyl]glycyl}amino)-methyl]phenyl}propanoic acid,
3-{3-[({N-(3-chloro-2-methylphenyl)-N-[(4-ethylphenyl)sulfonyl]glycyl}amino)methyl]phenyl}propanoic acid,
3-[({N-(3-chloro-2-methylphenyl)-N-[(2-fluoro-4-methylphenyl)sulfonyl]glycyl}-amino)methyl]benzoic acid,
(2E)-3-{3-[({N-(3-chloro-2-methylphenyl)-N-[(4-ethylphenyl)sulfonyl]glycyl}-amino)methyl]phenyl}acrylic acid,
4-[({N-(3-chloro-2-methylphenyl)-N-[(4-methylphenyl)sulfonyl]glycyl}amino)-methyl]-N-(2,3-dihydroxypropyl)benzamide,
4-[({N-(3-chloro-2-methylphenyl)-N-[(4-methylphenyl)sulfonyl]glycyl}amino)-methyl]-N-(1,3-dihydroxypropan-2-yl)benzamide,
3-[({N-(3-chloro-2-methylphenyl)-N-[(4-methylphenyl)sulfonyl]glycyl}amino)-methyl]-5-fluorobenzoic acid,
5-({[N-(3-chloro-2-methylphenyl)-N-{[4-(trifluoromethyl)phenyl]sulfonyl}glycyl]-amino}methyl)thiophene-3-carboxylic acid,
$N^2$-(3-chloro-2-methylphenyl)-N-[4-(4-hydroxy-2-oxopyrrolidin-1-yl)benzyl]-$N^2$-[(4-methylphenyl)sulfonyl]glycinamide,
4-[({N-(3-chloro-2-methylphenyl)-N-[(4-methylphenyl)sulfonyl]glycyl}amino)-methyl]-N-(ethylsulfonyl)benzamide,
4-[({N-(3-chloro-2-methylphenyl)-N-[(4-methylphenyl)sulfonyl]glycyl}amino)-methyl]-N-[(2-methoxyethyl)sulfonyl]benzamide,
$N^2$-(3-chloro-2-methylphenyl)-$N^2$-[(4-cyanophenyl)sulfonyl]-N-[4-(4-hydroxy-2-oxopyrrolidin-1-yl)benzyl]glycinamide,
4-[({N-(3-chloro-2-methylphenyl)-N-[(4-cyanophenyl)sulfonyl]glycyl}amino)-methyl]-N-(methylsulfonyl)benzamide,
4-[({N-(3-chloro-2-methylphenyl)-N-[(4-ethylphenyl)sulfonyl]glycyl}amino)methyl]-N-(methylsulfonyl)benzamide,
4-[({N-(3-chloro-2-methylphenyl)-N-[(4-chlorophenyl)sulfonyl]glycyl}amino)-methyl]-N-(methylsulfonyl)benzamide,
4-({[N-(3-chloro-2-methylphenyl)-N-{[4-(trifluoromethyl)phenyl]sulfonyl}glycyl]-amino}methyl)-N-(methylsulfonyl)benzamide,
$N^2$-(3-chloro-2-methylphenyl)-N-{[5-(2-oxopyrrolidin-1-yl)pyridin-2-yl]methyl}-$N^2$-{[4-(trifluoromethyl)phenyl]sulfonyl}glycinamide,
$N^2$-(3-chloro-2-methylphenyl)-N-[4-(4-hydroxy-2-oxopyrrolidin-1-yl)benzyl]-$N^2$-{[4-(trifluoromethyl)phenyl]sulfonyl}glycinamide,
2-[({N-(3-chloro-2-methylphenyl)-N-[(4-methylphenyl)sulfonyl]glycyl}amino)-methyl]-1,3-oxazole-4-carboxylic acid,
4-[({N-(3-chloro-2-methylphenyl)-N-[(4-methylphenyl)sulfonyl]glycyl}amino)-methyl]thiophene-2-carboxylic acid,
(2E)-3-{3-[({N-(3-chloro-2-methylphenyl)-N-[(4-methylphenyl)sulfonyl]glycyl}-amino)methyl]phenyl}-2-methylacrylic acid,
3-{3-[({N-(3-chloro-2-methylphenyl)-N-[(4-methylphenyl)sulfonyl]glycyl}amino)-methyl]phenyl}-2-methylpropanoic acid,
(2S)-2-{3-[({N-(3-chloro-2-methylphenyl)-N-[(4-methylphenyl)sulfonyl]glycyl}-amino)methyl]phenoxy}propionic acid,
(2R)-2-{3-[({N-(3-chloro-2-methylphenyl)-N-[(4-methylphenyl)sulfonyl]glycyl}-amino)methyl]phenoxy}propionic acid,
2-{3-[({N-(3-chloro-2-methylphenyl)-N-[(4-methylphenyl)sulfonyl]glycyl}amino)methyl]phenoxy}-2-methylpropanoic acid,
4-[({N-(3-chloro-2-methylphenyl)-N-[(4-chlorophenyl)sulfonyl]glycyl}amino)-methyl]thiophene-2-carboxylic acid,
4-({[N-(3-chloro-2-methylphenyl)-N-{[4-(trifluoromethyl)phenyl]sulfonyl}glycyl]-amino}methyl)thiophene-2-carboxylic acid,
4-[({N-(3-chloro-2-methylphenyl)-N-[(4-ethylphenyl)sulfonyl]glycyl}amino)-methyl]thiophene-2-carboxylic acid,
4-[({N-(3-chloro-2-methylphenyl)-N-[(2-fluoro-4-methylphenyl)sulfonyl]glycyl}-amino)methyl]thiophene-2-carboxylic acid,
4-[({N-(2,3-dichlorophenyl)-N-[(4-methylphenyl)sulfonyl]glycyl}amino)-methyl]thiophene-2-carboxylic acid,
4-[({N-(3-chloro-2-methoxyphenyl)-N-[(4-methylphenyl)sulfonyl]glycyl}amino)-methyl]thiophene-2-carboxylic acid,
4-[({N-(3-bromo-2-methylphenyl)-N-[(4-methylphenyl)sulfonyl]glycyl}amino)-methyl]thiophene-2-carboxylic acid,
(2R)-2-{3-[({N-(3-chloro-2-methylphenyl)-N-[(4-chlorophenyl)sulfonyl]glycyl]-amino)methyl]phenoxy}propanoic acid,
(2R)-2-[3-({[N-(3-chloro-2-methylphenyl)-N-{[4-(trifluoromethyl)phenyl]sulfonyl}-glycyl]amino}methyl)phenoxy]propanoic acid,
(2R)-2-{3-[({N-(3-chloro-2-methylphenyl)-N-[(4-ethylphenyl)sulfonyl]glycyl]-amino)methyl]phenoxy}propanoic acid, (2R)-2-{3-[({N-(3-chloro-2-methylphenyl)-N-[(2-fluoro-4-methylphenyl)sulfonyl]-glycyl}amino)methyl]phenoxy}propanoic acid, (2R)-2-{3-[({N-(2,3-dichlorophenyl)-N-[(4-methylphenyl)sulfonyl]glycyl}amino)methyl]phenoxy}propanoic acid, (2R)-2-{3-[({N-(3-chloro-2-methoxyphenyl)-N-[(4-methylphenyl)sulfonyl]glycyl}-amino)methyl]phenoxy}propanoic acid, (2R)-2-{3-[({N-(3-bromo-2-methylphenyl)-N-[(4-methylphenyl)sulfonyl]glycyl}-amino)methyl]phenoxy}propanoic acid, $N^2$-(3-chloro-2-methylphenyl)-$N^2$-[(4-methylphenyl)sulfonyl]-N-[3-(5-oxo-4,5-dihydro-1,2,4-oxadiazol-3-yl)benzyl]glycinamide, and $N^2$-(3-chloro-2-methylphenyl)-$N^2$-[(4-methylphenyl)sulfonyl]-N-[3-(2H-tetrazol-5-yl)benzyl]glycinamide, or a pharmaceutically acceptable salt thereof.

2. The compound or pharmaceutically acceptable salt thereof according to claim 1, which is selected from the group consisting of:

3-[({N-(3-chloro-2-methylphenyl)-N-[(4-methylphenyl)sulfonyl]glycyl}amino)-methyl]benzoic acid, 3-[({N-(3-chloro-2-methylphenyl)-N-[(4-chlorophenyl)sulfonyl]glycyl}amino)-methyl]benzoic acid, 3-[({N-(3-chloro-2-methylphenyl)-N-[(4-methylphenyl)sulfonyl]glycyl}amino)-methylphenoxyacetic acid, 4-[({N-(3-chloro-2-methylphenyl)-N-[(4-methylphenyl)sulfonyl]glycyl}amino)-methyl]-N-(methylsulfonyl)benzamide, 3-[({N-(3-chloro-2-methylphenyl)-N-[(4-cyanophenyl)sulfonyl]glycyl}amino)-methyl]benzoic acid, 3-{[(N-(3-chloro-2-methylphenyl)-N-{[4-(trifluoromethyl)phenyl]sulfonyl}glycyl)-amino]methyl}benzoic acid, 4-[({N-(3-chloro-2-methylphenyl)-N-[(4-methylphenyl)sulfonyl]glycyl}amino)-methyl]-2-methoxy-N-(methylsulfonyl)benzamide, 3-[({N-(2,3-dichlorophenyl)-N-[(4-methylphenyl)sulfonyl]glycyl}amino)methyl]benzoic acid, 3-[({N-(3-chloro-2-methoxyphenyl)-N-[(4-methylphenyl)sulfonyl]glycyl}amino)-methyl]benzoic acid, 3-[({N-(3-bromo-2-methylphenyl)-N-[(4-methylphenyl)sulfonyl]glycyl}amino)-methyl]benzoic acid, 3-[({N-(3-chloro-2-methylphenyl)-N-[(4-ethylphenyl)sulfonyl]glycyl}amino)-methyl]benzoic acid, 3-[({N-(3-chloro-2-ethylphenyl)-N-[(4-methylphenyl)sulfonyl]glycyl}amino)-methyl]benzoic acid, 3-[({N-(3-chloro-2-methylphenyl)-N-[(4-methylphenyl)sulfonyl]glycyl}amino)-methyl]cinnamic acid, 3-{3-[({N-(3-chloro-2-methylphenyl)-N-[(4-methylphenyl)sulfonyl]glycyl}amino)-methyl]phenyl}propionic acid, 5-[({N-(3-chloro-2-methylphenyl)-N-[(4-methylphenyl)sulfonyl]glycyl}amino)-methyl]thiophene-3-carboxylic acid, 3-[({N-(3-chloro-2-ethylphenyl)-N-[(4-methylphenyl)sulfonyl]glycyl}amino)-methyl]cinnamic acid, 3-{[(N-(3-chloro-2-methylphenyl)-N-{[4-(trifluoromethyl)phenyl]sulfonyl}glycyl)-amino]methyl}cinnamic acid, 3-[({N-(3-chloro-2-methylphenyl)-N-[(4-chlorophenyl)sulfonyl]glycyl}amino)-methyl]cinnamic acid, 3-(3-{[(N-(3-chloro-2-methylphenyl)-N-{[4-(trifluoromethyl)phenyl]sulfonyl}-glycyl)amino]methyl}phenyl)propionic acid, 3-[({N-(3-chloro-2-methylphenyl)-N-[(2-fluoro-4-methylphenyl)sulfonyl]glycyl}amino)-methyl]benzoic acid, 2-[({N-(3-chloro-2-methylphenyl)-N-[(4-methylphenyl)sulfonyl]glycyl}amino)-methyl]-1,3-oxazole-4-carboxylic acid, 4-[({N-(3-chloro-2-methylphenyl)-N-[(4-methylphenyl)sulfonyl]glycyl}amino)-methyl]thiophene-2-carboxylic acid, (2S)-2-{3-[({N-(3-chloro-2-methylphenyl)-N-[(4-methylphenyl)sulfonyl]glycyl}-amino)methyl]phenoxy}propionic acid, and (2R)-2-{3-[({N-(3-chloro-2-methylphenyl)-N-[(4-methylphenyl)sulfonyl]glycyl}-amino)methyl]phenoxy}propionic acid, or a pharmaceutically acceptable salt thereof.

3. The compound or pharmaceutically acceptable salt thereof according to claim 2, which is 3-[({N-(3-chloro-2-methylphenyl)-N-[(4-methylphenyl)sulfonyl]glycyl}amino)methyl]benzoic acid or a pharmaceutically acceptable salt thereof.

4. The compound or pharmaceutically acceptable salt thereof according to claim 2, which is 3-[({N-(3-chloro-2-methylphenyl)-N-[(4-methylphenyl)sulfonyl]glycyl}amino)methyl]phenoxyacetic acid or a pharmaceutically acceptable salt thereof.

5. The compound or pharmaceutically acceptable salt thereof according to claim 2, which is 4-[({N-(3-chloro-2-methylphenyl)-N-[(4-methylphenyl)sulfonyl]glycyl}amino)methyl]-N-(methylsulfonyl)benzamide or a pharmaceutically acceptable salt thereof.

6. The compound or pharmaceutically acceptable salt thereof according to claim 2, which is 3-[({N-(3-chloro-2-ethylphenyl)-N-[(4-methylphenyl)sulfonyl]glycyl}amino)methyl]benzoic acid or a pharmaceutically acceptable salt thereof.

7. The compound or pharmaceutically acceptable salt thereof according to claim 2, which is 3-[({N-(3-chloro-2-ethylphenyl)-N-[(4-methylphenyl)sulfonyl]glycyl}amino)methyl]cinnamic acid or a pharmaceutically acceptable salt thereof.

8. The compound or pharmaceutically acceptable salt thereof according to claim 2, which is 4-[({N-(3-chloro-2-methylphenyl)-N-[(4-methylphenyl)sulfonyl]glycyl}amino)methyl]thiophene-2-carboxylic acid or a pharmaceutically acceptable salt thereof.

9. The compound or pharmaceutically acceptable salt thereof according to claim 2, which is (2R)-2-{3-[({N-(3-chloro-2-methylphenyl)-N-[(4-methylphenyl)sulfonyl]glycyl}amino)methyl]phenoxy}propionic acid or a pharmaceutically acceptable salt thereof.

10. A pharmaceutical composition, comprising a compound or pharmaceutically acceptable salt thereof according to claim 1 and a pharmaceutically acceptable carrier.

11. A pharmaceutical composition, comprising a compound or pharmaceutically acceptable salt thereof according to claim 2 and a pharmaceutically acceptable carrier.

12. A pharmaceutical composition, comprising a compound or pharmaceutically acceptable salt thereof according to claim 3 and a pharmaceutically acceptable carrier.

13. A pharmaceutical composition, comprising a compound or pharmaceutically acceptable salt thereof according to claim 4 and a pharmaceutically acceptable carrier.

14. A pharmaceutical composition, comprising a compound or pharmaceutically acceptable salt thereof according to claim 5 and a pharmaceutically acceptable carrier.

15. A pharmaceutical composition, comprising a compound or pharmaceutically acceptable salt thereof according to claim 6 and a pharmaceutically acceptable carrier.

16. A pharmaceutical composition, comprising a compound or pharmaceutically acceptable salt thereof according to claim 7 and a pharmaceutically acceptable carrier.

17. A pharmaceutical composition, comprising a compound or pharmaceutically acceptable salt thereof according to claim 8 and a pharmaceutically acceptable carrier.

18. A pharmaceutical composition, comprising a compound or pharmaceutically acceptable salt thereof according to claim 9 and a pharmaceutically acceptable carrier.

19. A method for treating urinary frequency, comprising administering a therapeutically effective amount of a compound or pharmaceutically acceptable salt thereof according to claim 1 to a patient in need thereof.

20. The method according to claim 19, wherein said urinay frequency is caused by overactive bladder, benign prostatic hyperplasia, bladder neck contracture, cystitis, or prostatitis.

* * * * *